(12) United States Patent
Ishii et al.

(10) Patent No.: US 7,847,089 B2
(45) Date of Patent: Dec. 7, 2010

(54) RNA INTERFERENCE INDUCTION ELEMENT AND USE THEREOF

(75) Inventors: Kojiro Ishii, Fukuoka (JP); Kohta Takahashi, Fukuoka (JP)

(73) Assignees: Kurume University, Fukuoka (JP); Japan Science and Technology Agency, Saitama (JP)

( * ) Notice: Subject to any disclaimer, the term of this patent is extended or adjusted under 35 U.S.C. 154(b) by 278 days.

(21) Appl. No.: 11/920,508

(22) PCT Filed: May 15, 2006

(86) PCT No.: PCT/JP2006/310079

§ 371 (c)(1), (2), (4) Date: Jan. 3, 2008

(87) PCT Pub. No.: WO2006/123800

PCT Pub. Date: Nov. 23, 2006

(65) Prior Publication Data

US 2009/0215644 A1    Aug. 27, 2009

(30) Foreign Application Priority Data

May 18, 2005   (JP)   .............................. 2005-145876

(51) Int. Cl.
   *C07H 21/04*   (2006.01)
   *A01N 43/04*   (2006.01)
   *A61K 31/70*   (2006.01)

(52) U.S. Cl. ........................................ 536/24.5; 514/44

(58) Field of Classification Search ................. 536/24.5
   See application file for complete search history.

(56) References Cited

PUBLICATIONS

V. Wood et al., "The Genome Sequence of *Schizosaccharomyces pombe*", Nature, vol. 415, No. 6874, pp. 871-880, Feb. 2002.

K. Takahashi et al., "A Low Copy Number Central Sequence with Strict Symmetry and Unusual Chromatin Structure in Fission Yeast Centromere", Molecular Biology of the Cell, vol. 3, No. 7, pp. 819-835, Jul. 1992.

Y. Nakaseko et al., "A Novel Sequence Common to the Centromere Regions of *Schizosaccharomyces pombe* Chromosomes", Nucleic Acids Research, vol. 15, No. 12, pp. 4705-4715, 1987.

T. A. Volpe et al., "Regulation of Heterochromatic Silencing and Histone H3 Lysine-9 Methylation by RNAi", Science, vol. 297, No. 5588, pp. 1833-1837, Sep. 13, 2002.

A. M. Denli et al., "RNAi: An Ever-Growing Puzzle", TRENDS in Biochemical Sciences, vol. 28, No. 4, pp. 196-201, Apr. 2003.

R. A. Martienssen et al., "RNA Interference and Heterochromatin in the Fission Yeast *Schizosaccharomyces pombe*", TRENDS in Genetics, vol. 21, No. 8, pp. 450-456, Aug. 2005.

T. Volpe et al., "RNA Interference is Required for Normal Centromere Function in Fission Yeast", Chromosome Research, vol. 11, pp. 137-146, 2003.

B. J. Reinhart et al., "Small RNAs Correspond to Centromere Heterochromatic Repeats", Science, vol. 297, No. 5588, p. 1831, Sep. 13, 2002.

*Primary Examiner*—Brian Whiteman
(74) *Attorney, Agent, or Firm*—Wenderoth, Lind & Ponack, L.L.P.

(57) ABSTRACT

The present invention provides an RNA interference induction element containing a nucleotide sequence selected from among the nucleotide sequences (a) to (c) below: (a) a nucleotide sequence containing SEQ ID NO:1 or a sequence complementary thereto; (b) a nucleotide sequence containing at least 15 continuous nucleotides present in the nucleotide sequence (a) above, and possessing RNA interference induction potential; (c) a nucleotide sequence having a homology of at least 70% to any one of the nucleotide sequences (a) and (b) above, and possessing RNA interference induction potential. Using the RNA interference induction element of the present invention, it is easily possible to knock down a desired target gene, and to produce a siRNA for a desired target gene.

32 Claims, 11 Drawing Sheets

RNA INTERFERENCE INDUCTION ELEMENT AND USE THEREOF

This application is a U.S. national stage of International Application No. PCT/JP2006/310079 filed May 15, 2006.

TECHNICAL FIELD OF THE INVENTION

The present invention relates to an RNA interference induction element and a use thereof. More specifically, the present invention relates to an RNA interference induction element comprising a nucleotide sequence comprising SEQ ID NO:1 or a sequence complementary thereto or the like, a vector harboring the element, cells containing the vector, a method of producing cells wherein the expression of a target gene is suppressed or a siRNA for the target gene using the element, and the like.

BACKGROUND OF THE INVENTION

RNA interference (RNAi) is a phenomenon in which mRNA is degraded by double-stranded RNA (dsRNA) and the like with specificity for the sequence thereof, resulting in suppression of gene expression. RNA interference has been shown to be conserved across various organisms, including nematodes, yeast and other fungi, insects, plants, and mammals, suggesting that it is a biological system common to all organisms.

Known biological roles of RNA interference include heterochromatin control in fission yeast and the like, control of DNA deletion in *Tetrahymena* and the like, and the like. It has been reported that deletion of Dicer (dcr1), Argonaute (ago1), or RdRp (rdp1) (these are genes playing important roles in the RNAi pathway) in fission yeast (mutants dcr1⁻, ago1⁻, and rdp1⁻, respectively) resulted in the aberrant accumulation of complementary transcripts from outer centromeric heterochromatic repeats, and this was accompanied by transcriptional de-repression of transgenes integrated at the centromere, loss of histone H3 lysine-9 methylation, and impairment of centromere function (Science, Vol. 297, pp. 1833-1837, 2002). Additionally, it was suggested that a short RNA derived from centromeric repeats is present in fission yeasts (Science, Vol. 297, p. 1831, 2002).

Because RNA interference enables the selective knockdown of a desired gene, it is highly expected to find new applications in biotechnological areas such as breed improvement of crop and medical areas such as gene therapy, as well as in basic sciences such as biochemistry.

There are two major methods of knocking down a gene by RNA interference: direct transfer of siRNA (short interfering RNA) into cells and transfer of siRNA expression vector into cells. Although the former method is quite simple, it is faulty in that the effect of the siRNA introduced does not persist for a long time when it is degraded. The latter siRNA expression vector method, on the other hand, is advantageous in that it enables the preparation of knockdown cell lines or knockdown animals thanks to the long persisting effect thereof. Because RNA interference in cells is triggered by the formation of double-stranded RNA, however, many siRNA expression vectors produce double-stranded RNAs such as hairpin RNAs, which in turn can cause the vector DNA itself to have a stem loop structure and hence become unstable in *Escherichia coli*; it has been difficult to construct a siRNA expression vector.

SUMMARY OF THE INVENTION

In view of the above-described circumstances, the present invention is directed to provide a method of easily inducing RNA interference for a desired gene.

The present inventors diligently investigated to solve the problem described above, mapped centromeric siRNAs of fission yeast in centromeric repeats by Northern blotting, and found that the siRNAs are abundant in the vicinity of a particular shared nucleotide sequence. When a polynucleotide incorporating a desired gene connected with the nucleotide sequence was transferred to cells, RNA interference for the gene was induced. The inventors thus found that the nucleotide sequence serves as an RNA interference induction element, and developed the present invention. Accordingly, the present invention relates to the following:

[1] An RNA interference induction element comprising a nucleotide sequence selected from among the nucleotide sequences (a) to (c) below:

(a) a nucleotide sequence comprising SEQ ID NO:1 or a sequence complementary thereto;

(b) a nucleotide sequence comprising at least 15 continuous nucleotides present in the nucleotide sequence (a) above, and possessing RNA interference induction potential;

(c) a nucleotide sequence having a homology of at least 70% to any one of the nucleotide sequences (a) and (b) above, and possessing RNA interference induction potential.

[2] A polynucleotide comprising the element described in [1] above, wherein a nucleotide sequence comprising at least 15 continuous nucleotides present in the nucleotide sequence that encodes the transcript of a target gene, or a sequence complementary thereto, is connected so that RNA interference induction potential for the target gene can be exhibited.

[3] The polynucleotide described in [2] above, wherein the nucleotide sequence is connected to the 5' side of the element.

[4] The polynucleotide described in [2] above, which comprises plural copies of the element as connected in tandem.

[5] A vector harboring the element described in [1] above.

[6] The vector described in [5] above, which comprises plural copies of the element as connected in tandem.

[7] The vector described in [5] or [6] above, which further harbors a promoter joined to the element so that the expression of the element can be controlled.

[8] The vector described in [5] or [6] above, which further harbors at least one cloning site connected to the element so that RNA interference induction potential for a target gene can be exhibited when a nucleotide sequence comprising at least 15 continuous nucleotides present in the nucleotide sequence that encodes the transcript of the target gene or a sequence complementary thereto is inserted to the cloning site.

[9] The vector described in [8] above, wherein the cloning site is connected to the 5' side of the element.

[10] The vector described in [8] or [9] above, which further harbors a promoter joined to the element or the cloning site so that the expression of the element and the cloning site can be controlled.

[11] A vector harboring the polynucleotide described in any of [2] to [4] above.

[12] The vector described in [11] above, which further harbors a promoter joined to the polynucleotide so that the expression of the polynucleotide can be controlled.

[13] A cell incorporating the polynucleotide described in any of [2] to [4] above.

[14] A cell incorporating the vector described in any of [5] to [12] above.

[15] A method of producing a cell wherein the expression of a target gene is suppressed, which comprises a step for transferring the polynucleotide described in any of [2] to [4] above, or the vector described in [11] or [12] above, into cells, and a step for selecting a cell incorporating the polynucleotide or the vector.

[16] A method of suppressing the expression of a target gene, which comprises a step for transferring the polynucleotide described in any of [2] to [4] above, or the vector described in [11] or [12] above, into cells.

[17] A method of producing a siRNA for a target gene, which comprises a step for transferring the polynucleotide described in any of [2] to [4] above, or the vector described in [11] or [12] above, into cells, and a step for obtaining the siRNA for the target gene from the cells incorporating the polynucleotide or the vector.

[18] An RNA interference inducing agent comprising the polynucleotide described in any of [2] to [4] above, or the vector described in [11] or [12] above.

[19] A gene knockdown polynucleotide library comprising a plurality of polynucleotides, each of which comprises a nucleotide sequence comprising at least 15 continuous nucleotides present in the nucleotide sequence that encodes each of the transcripts of a plurality of genes or a sequence complementary thereto, wherein each nucleotide sequence is connected to the element described in [1] above so that RNA interference induction potential for the gene can be exhibited.

[20] The library described in [19] above, wherein the each polynucleotide is harbored in a vector.

[21] A cellular population incorporating the library described in [19] or [20] above.

[22] A method of screening for a functional gene, which comprises the steps (a) to (c) below:

(a) analyzing the phenotype of a cellular population incorporating the library described in [19] or [20] above;

(b) isolating cells with an altered phenotype from the cellular population; and (c) obtaining a functional gene based on a nucleotide sequence in the polynucleotide or the vector incorporated in the isolated cells.

[23] An RNA-dependent RNA synthesis reaction induction element comprising a nucleotide sequence selected from among the nucleotide sequences (a) to (c) below:

(a) a nucleotide sequence comprising SEQ ID NO:1 or a sequence complementary thereto;

(b) a nucleotide sequence comprising at least 15 continuous nucleotides present in the nucleotide sequence (a) above, and possessing RNA-dependent RNA synthesis reaction induction potential;

(c) a nucleotide sequence having a homology of at least 70% to any one of the nucleotide sequences (a) and (b) above, and possessing RNA-dependent RNA synthesis reaction induction potential.

[24] A template for an RNA-dependent RNA synthesis reaction comprising the element described in [23] above.

[25] A vector capable of expressing the template described in [24] above.

[26] A cell incorporating the vector described in [25] above.

[27] A method of synthesizing an RNA, which comprises the steps shown below:

(a) a step for providing a template for an RNA-dependent RNA synthesis reaction comprising the element of [23] above;

(b) a step for bringing the template of (a) in contact with RNA-dependent RNA polymerase to cause the RNA-dependent RNA synthesis reaction.

[28] A gene expression suppression element comprising a nucleotide sequence selected from among the nucleotide sequences (a) to (c) below:

(a) a nucleotide sequence comprising SEQ ID NO:1 or a sequence complementary thereto;

(b) a nucleotide sequence comprising at least 15 continuous nucleotides present in the nucleotide sequence (a) above, and possessing gene expression suppression potential;

(c) a nucleotide sequence having a homology of at least 70% to any one of the nucleotide sequences (a) and (b) above, and possessing gene expression suppression potential.

EFFECT OF THE INVENTION

Figure 1:
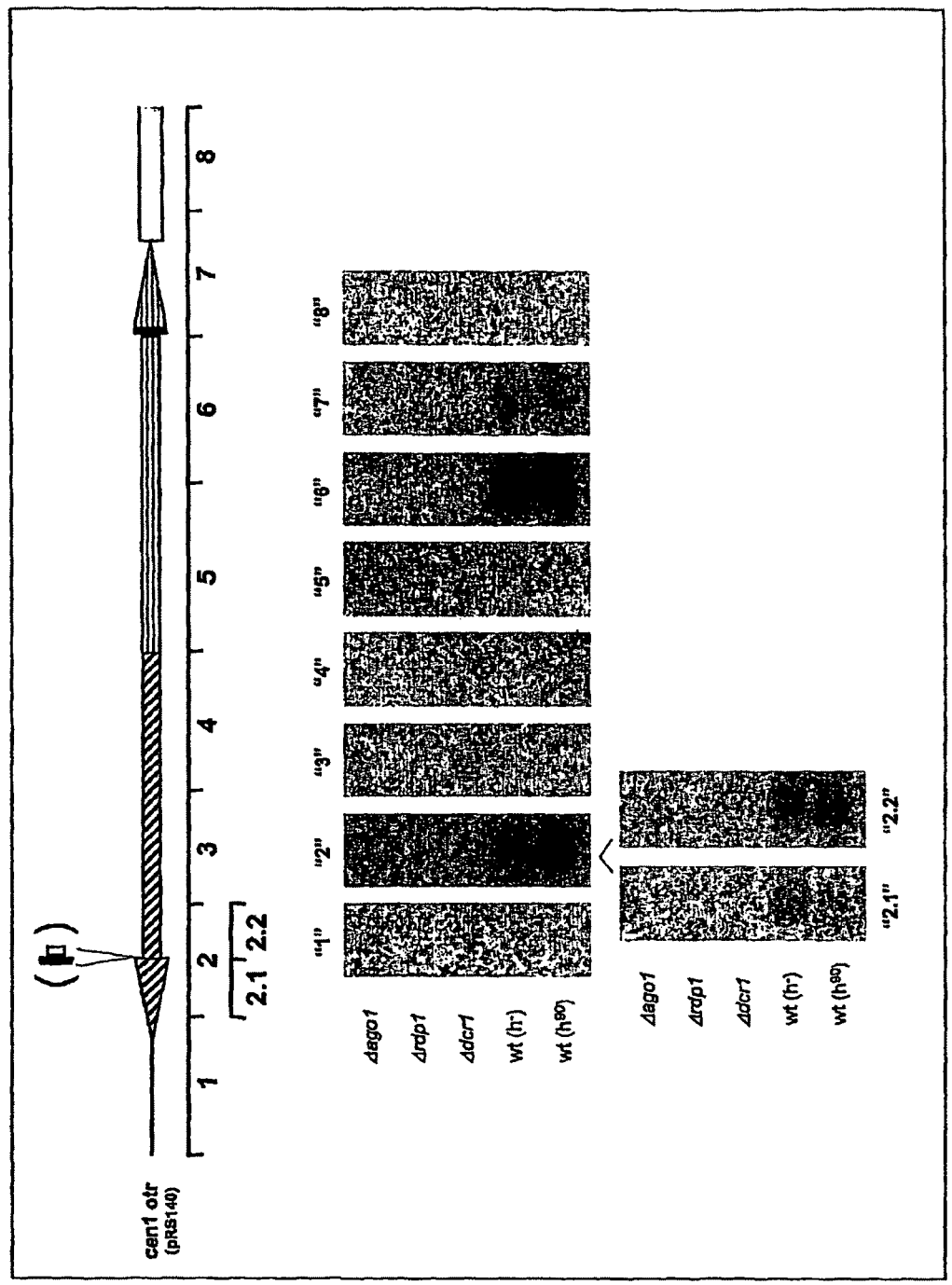
FIG. 1 shows the results of Northern blotting using Regions 1 to 8, obtained by dividing the otr repeat (pRS140) in the left arm of the first chromosome centromere of fission yeast into the eight portions, as the probes, to detect small-molecule RNAs in the fission yeast.

Using the RNA interference induction element of the present invention, it is easily possible to knock down a desired target gene and produce a siRNA for a desired target gene.

BEST MODE FOR EMBODYING THE INVENTION

The present invention is hereinafter described in detail. Throughout this description, a singular form can include the concept of the plural form thereof unless otherwise stated. Additionally, the terms as used herein are used to have ordinary meanings in the art unless otherwise stated.

Terms that frequently appear herein are defined below.

The term "polynucleotide" as used herein has the same meaning as "oligonucleotide", "nucleic acid", and "nucleic acid molecule", and refers to a nucleotide polymer of an optionally chosen length. Although the polynucleotide may be a DNA, an RNA, or a DNA/RNA chimera, it is preferably a DNA or an RNA. Additionally, the polynucleotide may be double-stranded or single-stranded. In the case of a double-stranded polynucleotide, it may be a double-stranded DNA, a double-stranded RNA, or a DNA:RNA hybrid. Furthermore, the polynucleotide may be an unmodified polynucleotide (or unmodified oligonucleotide); a polynucleotide with a known modification, for example, one with a label known in the art, one with a cap, one methylated, one with one or more naturally occurring nucleotides substituted by analogues; or a polynucleotide with an intramolecularly modified nucleotide for example, one with an uncharged bond (e.g., methyl phosphonate, phosphotriester, phosphoramidate, carbamate and the like), one with a charged bond or sulfur-containing bond (e.g., phosphorothioate, phosphorodithioate and the like), and one with a modified bond (e.g., α-anomeric nucleic acids and the like). Here, "nucleoside", "nucleotide" and "nucleic acid" may comprise not only the purine and pyrimidine bases, but also other modified heterocyclic bases. Such modified products may comprise methylated purine and pyrimidine, acylated purine and pyrimidine, or another heterocyclic ring. The modified nucleoside and modified nucleotide may have a modification in the sugar moiety thereof; for example, one or more hydroxyl groups may be substituted by halogens, aliphatic groups and the like, or may be converted into functional groups such as ethers and amines.

Nucleotide sequences are herein described as DNA sequences unless otherwise specified; however, when the polynucleotide is an RNA, thymine (T) should read as uracil (U) as appropriate.

The term "gene" as used herein refers to a factor that determines a genetic character. Genes are usually placed in chromosomes in a particular order. A gene that determines the primary structure of a protein is called a structural gene, and a gene that controls the expression thereof is called a regulator gene (e.g., promoter). Herein genes encompass both structural genes and regulator genes unless otherwise stated. The term "gene" as used herein may also refer to. "a polynucleotide", "an oligonucleotide" and "a nucleic acid" and/or "a protein", "a polypeptide", "an oligopeptide" and "a peptide". The term "gene product" as used herein encompasses "a polynucleotide", "an oligonucleotide" and "a nucleic acid" and/or "a protein", "a polypeptide", "an oligopeptide" and "a peptides" expressed by the genes. Those skilled in the art can understand what is the gene product according to the situation.

The term "homology" as used herein with respect to genes (e.g., nucleotide sequences, amino acid sequences and the like) refers to the extent of mutual identity of two or more gene sequences. Accordingly, as the homology of two particular genes increases, the extent of mutual identity or similarity of the sequences thereof increases. Whether or not two kinds of genes possess a homology can be determined by a direct comparison of the sequences, or, in the case of a polynucleotide, by the hybridization method under stringent conditions. Referring to a direct comparison of two gene sequences, these genes are judged to possess a homology when their nucleotide sequences are typically at least 50% identical, preferably at least 70% identical, and more preferably at least 80%, 90%, 95%, 96%, 97%, 98% or 99% identical, to each other. The term "similarity" of genes (e.g., nucleotide sequences, amino acid sequences and the like) as used herein refers to the extent of mutual identity of two or more gene sequences, provided that conservative substitutions are deemed positive (identical) in the above-described homology. Accordingly, if there is a conservative substitution, identity and similarity differ from each other depending on the presence of the conservative substitution. Additionally, if there is no conservative substitution, identity and similarity show the same numerical value.

Algorithms to determine gene homology include, for example, but are not limited to, the algorithm described in Karlin et al., Proc. Natl. Acad. Sci. USA, 90: 5873-5877 (1993) [the algorithm is incorporated in the NBLAST and XBLAST programs (version 2.0) (Altschul et al., Nucleic Acids Res., 25: 3389-3402 (1997))], the algorithm described in Needleman et al., J. Mol. Biol., 48: 444-453 (1970) [the algorithm is incorporated in the GAP program in the GCG software package], the algorithm described in Myers and Miller, CABIOS, 4: 11-17 (1988) [the algorithm is incorporated in the ALIGN program (version 2.0), which is part of the CGC sequence alignment software package], the algorithm described in Pearson et al., Proc. Natl. Acad. Sci. USA, 85: 2444-2448 (1988) [the algorithm is incorporated in the FASTA program in the GCG software package] and the like. Gene homology can be calculated as appropriate with the above-described program using default parameters thereof. For example, nucleotide sequence homology can be calculated using the homology calculation algorithm NCBI BLAST (National Center for Biotechnology Information Basic Local Alignment Search Tool) under the following conditions (expectancy=10; gap allowed; filtering=ON; match score=1; mismatch score=−3).

Although the length of a polynucleotide can herein be shown by the number of nucleotide units, the number is not unconditional; the number as the upper or lower limit is intended to include several units (or, for example, 10% above and below) straddling the number, as long as the same function is retained. To express this intent, the number may herein be preceded by the adjective "about". It should be understood, however, that the presence or absence of "about" herein does not influence the interpretation of the numerical value.

The term "transcript" as used herein refers to an RNA produced by gene transcription (mRNA and the like). Transcripts include initial transcripts (immature mRNA), mature transcripts resulting from post-transcriptional processing (splicing) (mature mRNA), and splicing variants thereof.

The term "expression" of a gene or a gene product such as a polynucleotide or a polypeptide as used herein refers to a-phenomenon in which the gene and the like undergoes a particular action in vivo (intracellularly) to turn into another form. Preferably, "expression" refers to a phenomenon in which a gene, a polynucleotide, and the like undergoes transcription and translation to turn into the form of a polypeptide; transcription to produce a transcript (mRNA and the like) can also be a form of expression.

Accordingly, the term "suppression" of the "expression" of a gene, a polynucleotide, a polypeptide, and the like as used herein refers to a significant reduction in the amount expressed when a particular factor is allowed to act compared to the amount expressed without the action. Preferably, suppression of the expression includes a reduction in the amount of polypeptide expressed. The term "induction" of the "expression" of a gene as used herein refers to increasing the amount of the gene expressed by allowing a particular factor to act on a cell. Therefore, induction of the expression encompasses allowing the gene to be expressed in cases where no expression of the gene has been observed, and increasing the expression of the gene in cases where the expression of the gene has been observed.

The term "detection" or "quantitation" of gene expression (e.g., mRNA expression, polypeptide expression) can, for example, be accomplished using an appropriate method, including mRNA assay and immunological assay methods. Examples of molecular biological assay methods include Northern blotting; dot blotting, PCR and the like. Examples of immunological assay methods include ELISA using microtiter plates, RIA, fluorescent antibody method, Western blotting, immunohistological staining and the like. Additionally, examples of methods of quantitation include ELISA, RIA and the like. The detection or quantitation can also be performed by genetic analyses using arrays (e.g., DNA arrays, protein arrays). An extensive overview of DNA arrays is given in "DNA Microar-rays and Current PCR Techniques", extra issue, Saibo Kogaku (Cell Engineering), published by Shujunsha. Protein arrays are described in detail in Nat Genet. 2002 December; 32 Suppl: 526-32. In addition to these methods, methods of gene expression analysis include, but are not limited to, RT-PCR, RACE, SSCP, immunoprecipitation, two-hybrid system, in vitro translation and the like. Such analytical methods are described in, for example, Genomu Kaiseki Jikkenhou—Yusuke Nakamura's Lab Manual, edited by Yusuke Nakamura, Yodosha (2002) and elsewhere.

The term "RNA interference (also referred to as RNAi)" as used herein refers to a phenomenon in which homologous-mRNA is specifically degraded and the expression (synthesis) of a gene product is suppressed by transferring a factor that causes RNA interference, such as double-stranded RNA (also called dsRNA) or siRNA, to cells, and a technology used therefor.

The term "siRNA" as used herein is an abbreviation for short interfering RNA, referring to a short, double-stranded RNA of 10 base pairs or more, that has been synthesized artificially, chemically, biochemically or intracellularly, or that has resulted from intracellular degradation of a double-stranded RNA of about 40 bases or more; a siRNA normally has the 5'-phosphoric acid and 3'-OH structure, with about two bases protruding at the 3' end. The length of siRNA is normally about 2.0 bases (e.g., typically about 21 to 23 bases) or less, and is not subject to limitation, as long as RNA interference can be induced.

While not being restrained theoretically, a likely mechanism for RNA interference is such that when a molecule that induces RNA interference, like dsRNA, is transferred into a cell, an RNase III-like nuclease with a helicase domain, known as a dicer, cleaves the molecule by about every 20 base pairs from the 3' end thereof in the presence of ATP, to produce a short dsRNA (siRNA), in the case of a relatively long (e.g., 40 base pairs or more) RNA. A specific protein binds to this siRNA to form an RNA-induced-silencing-complex (RISC). This complex recognizes and binds to an mRNA having the same sequence as siRNA, and cleaves the mRNA at the center of the siRNA by RNase III-like enzyme activity. Regarding the relationship between the sequence of the siRNA and the sequence of the mRNA cleaved as the target, a 100% identity is preferred. However, regarding mutations in bases at positions off the center of the siRNA (the mutations can be in the range of homology of at least 70%, preferably 80%, more preferably 90%, and most preferably 95% or more), the cleavage activity by RNAi is not completely lost, but the activity can remain partially. On the other hand, mutations in bases at the center of the siRNA have a major influence; the mRNA cleavage activity by RNAi may decline extremely.

Additionally, while not being restrained theoretically, another pathway for siRNA has been proposed. The antisense strand of siRNA binds to mRNA and acts as a primer for RNA-dependent RNA polymerase (RdRP) to synthesize a dsRNA. This dsRNA again serves as a dicer substrate to produce a new siRNA and enhance the action.

The term "cell" as used herein is defined as of the broadest sense used in the art, referring to an organism wrapped by a membranous structure isolating it from the outer world, capable of self-regeneration therein, and having genetic information and a mechanism for its expression, as the individual unit of a single-cell organism or the structural unit of a tissue of a multicellular organism. The cell used in the present invention may be a naturally occurring cell, or an artificially altered cell (e.g., fusion cell, genetically altered cell). The source of the cell can, for example, be a single cell culture, or includes, but is not limited to, embryos, blood, or somatic tissue of a normally grown wild type or transgenic animal, or a cell mixture like cells derived from a normally grown cell line.

The term "isolated" as used herein refers to a condition wherein substances that naturally accompany the object product in ordinary environments have been at least reduced, preferably substantially no such substances are contained in the object product. Accordingly, an isolated cell refers to a cell substantially free from other substances that naturally accompany the cells of interest in ordinary environment (e.g., other cells, proteins, nucleic acids and the like). The term "isolated" as used with respect to a polynucleotide or polypeptide refers to a polynucleotide or polypeptide substantially free from cellular substances and culture media when prepared by recombinant DNA technology, or a polynucleotide or polypeptide substantially free from precursor chemical substances or other chemical substances when chemically synthesized. The isolated polynucleotide is preferably free from sequences naturally flanking to the polynucleotide (i.e., sequences located at the 5' and 3' ends of the nucleic acid) in the organism from which the nucleotide is derived.

The term "purified" biological factor (e.g., a polynucleotide or polypeptide and the like) as used herein refers to a biological factor deprived of at least a portion of the factors naturally accompanying the biological factor. Therefore, the purity of a biological factor in a purified biological factor is normally higher than that of the biological factor in ordinary state (i.e., the biological factor has been concentrated).

The terms "purified" and "isolated" as used herein mean that preferably at least 75% by weight, more preferably at least 85% by weight, still more preferably at least 95% by weight, and most preferably at least 98% by weight, of the same type of biological factor is present.

Preferred modes of embodiment of the present invention are hereinafter described. The following modes of embodiment are understood to be given for the purpose of better understanding of the present invention, and not to be construed as limiting the scope of the invention. Accordingly, it is evident that those skilled in the art can alter these modes as appropriate within the scope of the present invention, in view of the description herein.

1. RNA Interference Induction Element

In one aspect, the present invention provides an RNA interference induction element comprising a nucleotide sequence selected from among the nucleotide sequences (a) to (c) below:

(a) a nucleotide sequence comprising SEQ ID NO:1 or a sequence complementary thereto;

(b) a nucleotide sequence comprising at least 15 continuous nucleotides present in the nucleotide sequence (a) above, and possessing RNA interference induction potential;

(c) a nucleotide sequence having a homology of at least 70% to any one of the nucleotide sequences (a) and (b) above, and possessing RNA interference induction potential.

The term "element" as used herein refers to a nucleotide sequence (or polynucleotide) having a particular function, or a region thereof.

The term "RNA interference induction potential" as used herein refers to the potential for inducing RNA interference for a functionally connected target gene. More specifically, "RNA interference induction potential" refers to the potential of a nucleotide sequence (or polynucleotide) for inducing RNA interference for an optionally chosen target gene; inducing siRNA for the target gene, or suppressing the expression of the target gene when transferred to cells, while being connected to a nucleotide sequence (target nucleotide sequence) comprising at least 15 continuous nucleotides present in the nucleotide sequence that encodes the transcript (mRNA) of the target gene, or a sequence complementary thereto. Accordingly, the terms "siRNA induction potential" and "gene expression suppression potential" can be used herein interchangeably with "RNA interference induction potential".

Accordingly, the term "RNA interference induction element" as used herein refers to a nucleotide sequence (or polynucleotide) having the above-described RNA interference induction potential, or a region thereof. The terms "siRNA induction element" and "gene expression suppression element" can be used herein interchangeably with "RNA interference induction element" as described above.

Additionally, when a single-stranded RNA comprising the RNA interference induction element of the present invention is transferred to cells, transcription of an RNA complementary to the RNA transferred is induced in the vicinity of the element (5' or 3' side); as a result, a double-stranded RNA comprising the RNA transferred and the RNA complementary thereto can be produced. In an embodiment, the RNA-dependent RNA synthesis (extension) reaction can proceed in the direction from the element of the present invention as the initiation site to the 3' side (this direction is the direction in the strand complementary to the RNA transferred). Accordingly, the RNA interference induction element of the present invention can be an "initiation site (element)" for the RNA-dependent RNA synthesis (extension) reaction, a "site (element) with priming function", or an "RNA-dependent RNA synthesis (extension) reaction induction element".

In a preferred mode of embodiment, the nucleotide sequence (b) above is preferably a nucleotide sequence comprising at least 15, for example, 50 or more, 100 or more, 150 or more, 200 or more, 250 or more, 300 or more, 310 or more, 320 or more, 330 or more, 340 or more, 350 or more, 360 or more, or 370 or more continuous nucleotides present in SEQ ID NO:1 or a sequence complementary thereto, and possessing RNA interference induction potential. Although a longer nucleotide sequence is preferred, the nucleotide sequence may be short, as long as it possesses RNA interference induction potential.

In another preferred mode of embodiment, the nucleotide sequence (c) above is preferably a nucleotide sequence having a homology of at least 70%, for example, 80% or more, 85% or more, 90% or more, 95% or more, 96% or more, 97% or more, 98% or more, or 99% or more, to any one of the nucleotide sequences (a) and (b) above, and possessing RNA interference induction potential. Although a higher homology is preferred, the nucleotide sequence may be of low homology, as long as it possesses RNA interference induction potential.

In (b) and (c) above, the potency of RNA interference induction potential is preferably equivalent (e.g., about 0.01 to 100 times, preferably about 0.1 to 10 times, more preferably about 0.5 to 2 times) to that of an RNA interference induction element comprising SEQ ID NO:1 or a sequence complementary thereto.

Because the nucleotide sequence of SEQ ID NO:1 is a sequence derived from the centromeric region of the chromosome DNA of fission yeast, a polynucleotide comprising the RNA interference induction element of the present invention can be obtained by a commonly known PCR method with the fission yeast chromosome DNA as the template using a synthetic DNA primer comprising a portion of the nucleotide sequence of SEQ ID NO:1. Alternatively, the same can also be obtained from a fission yeast chromosome DNA library by a hybridization method. This hybridization can be performed according to, for example, the method described in Molecular Cloning 2nd (J. Sambrook et al., Cold Spring Harbor Lab. Press, 1989) and the like. Alternatively, the same can also be obtained by chemical synthesis using a commercially available nucleic acid synthesizer. Additionally, these methods may be used in combination with a site-directed mutagenesis method known per se (ODA-LA PCR method, gapped duplex method, Kunkel method and the like) or a method based thereon.

The presence/absence or potency of RNA interference induction potential in the polynucleotide obtained can be confirmed by connecting the polynucleotide to a nucleotide sequence (target nucleotide sequence) comprising at least 15 continuous nucleotides present in the nucleotide sequence that encodes the transcript (mRNA) of an optionally chosen target gene or a sequence complementary thereto to obtain the polynucleotide of the present invention described below, transferring this polynucleotide to a cell, and detecting or quantifying the presence/absence or potency of the induction of RNA interference for the target gene, induction of siRNA for the target gene, or suppression of the expression of the target gene.

Using the RNA interference induction element of the present invention, it is possible to induce RNA interference for a desired gene, to induce siRNA, and to suppress the expression.

2. A Polynucleotide Comprising an RNA Interference Induction Element

In one aspect, the present invention provides a polynucleotide comprising the above-described RNA interference induction element of the present invention, wherein a nucleotide sequence (also referred to as the target nucleotide sequence) comprising at least 15 continuous nucleotides present in the nucleotide sequence that encodes the transcript of a target gene or a sequence complementary thereto is connected so that RNA interference induction potential for the target gene can be exhibited.

The term "target gene" as used herein refers to a gene intended to have the expression thereof suppressed by RNA interference, and the target gene can be selected optionally. As such, the target gene selected is preferably a gene of known sequence whose function is to be clarified, a gene whose expression is considered to be a cause of disease, or the like. The target gene selected may be a gene whose full-length genome sequence or full-length mRNA sequence remains unknown, provided that a portion, at least 15 bases or more, of the nucleotide sequence of the transcript (mRNA and the like) thereof is known. Therefore, a gene whose mRNA has been partially known but whose full-length remains unknown, such as expressed sequence tag (EST), can also be selected as a target gene in the present invention.

Although the transcript used may be any of an initial transcript, a mature transcript, and a splicing variant thereof, a mature transcript is preferably used.

Although the length of the target nucleotide sequence is not subject to limitation, as long as the polynucleotide of the present invention is capable of inducing RNA interference for the target gene when transferred to cells, the target nucleotide sequence is preferably a nucleotide sequence comprising at least 15, for example, 20 or more, 21 or more, 23 or more, 40 or more, 60 or more, or 100 or more continuous nucleotides present in the nucleotide sequence that encodes the transcript of a target gene or a sequence complementary thereto, considering that the length of siRNA is about 20 bases (e.g., typically about 21 to 23 bases). From the viewpoint of more potently inducing RNA interference for a target gene, the length of the target nucleotide sequence is preferably longer; examples of preferable target nucleotide sequences include, but are not limited to, the full-length of the nucleotide sequence that encodes the transcript of a target gene or a sequence complementary thereto, the full-length of the ORF region of the nucleotide sequence of the transcript of a target gene or a sequence complementary thereto and the like.

Additionally, the target nucleotide sequence may be connected adjacently to the RNA interference induction element of the present invention (not via a spacer region), or may be connected via a spacer region, as long as RNA interference induction potential for the target gene can be exhibited. Although the length of the spacer region is not subject to limitation, as long as the individual constituents, from the target nucleotide sequence to the RNA interference induction element of the present invention, can be stably present without interruption in one polynucleotide chain, and RNA interference induction potential for the target gene can be exhibited, it is preferably at most 10 Kbp, for example, 5 Kbp or less, 3 Kbp or less, 1 Kbp or less, 500 bp or less, 200 bp or less, 100 bp or less, 50 bp or less, or 25 bp or less. The nucleotide sequence that constitutes the spacer region is not subject to limitation, and may be an optionally chosen sequence.

Although the target nucleotide sequence may be connected to any of the 5' and 3' sides of the RNA interference induction element of the present invention, as long as RNA interference induction potential for the target gene can be exhibited, it is preferably connected to the 5' side.

Here, for the sake of convenience for the designation of the RNA interference induction element of the present invention, an element comprising:

(a') a nucleotide sequence comprising SEQ ID NO:1, (b') a nucleotide sequence comprising at least 15 continuous nucleotides present in the nucleotide sequence (a') above, and possessing RNA interference induction potential, or (c') a nucleotide sequence having a homology of at least 70% to any one of the nucleotide sequences (a') and (b') above, and possessing RNA interference induction potential, is referred to as "a sense element", and an element comprising (a") a nucleotide sequence comprising a sequence complementary to SEQ ID NO:1, (b") a nucleotide sequence comprising at least 15 continuous nucleotides present in the nucleotide sequence (a") above, and possessing RNA interference induction potential, or (c") a nucleotide sequence having a homology of at least 70% to any one of the nucleotide sequences (a") and (b") above, and possessing RNA interference induction potential, is referred to as "an antisense element".

Additionally, with respect to the polynucleotide of the present invention, "a nucleotide sequence comprising at least 15 continuous nucleotides present in the nucleotide sequence that encodes the transcript of a target gene" is referred to as "a sense target nucleotide sequence", and "a nucleotide sequence comprising at least 15 continuous nucleotides present in a sequence complementary to the nucleotide sequence that encodes the transcript of a target gene" is referred to as "an antisense target nucleotide sequence".

Provided that the target nucleotide sequence is connected to the 5' side of the RNA interference induction element of the present invention, the following four forms (A) to (D) are available:

(A) 5'-sense target nucleotide sequence-sense element-3'

(B) 5'-antisense target nucleotide sequence-sense element-3'

(C) 5'-sense target nucleotide sequence-antisense element-3'

(D) 5'-antisense target nucleotide sequence-antisense element-3'

Provided that the target nucleotide sequence is connected to the 3' side of the RNA interference induction element of the present invention, the following four forms (A') to (D') are available:

(A') 5'-sense element-sense target nucleotide sequence-3'

(B') 5'-sense element-antisense target nucleotide sequence-3'

(C') 5'-antisense element-sense target nucleotide sequence-3'

(D') 5'-antisense element-antisense target nucleotide sequence-3'

The polynucleotide of the present invention may be in a form in which the RNA interference induction element of the present invention is inserted in the midst of the target nucleotide sequence. In this case, it is preferable that at least one of the nucleotide sequence on the 5' side of the RNA interference induction element insertion site in the target nucleotide sequence, and the nucleotide sequence on the 3' side of the insertion site, have the same length as the above-described "length of the target nucleotide sequence".

Additionally, as long as RNA interference induction potential for the target gene can be exhibited, the RNA interference induction element inserted may be connected adjacently to the target nucleotide sequence (not via a spacer region), or may be joined via a spacer region, on the 5' and/or 3' side thereof. The length/sequence of the spacer region are the same as those described above.

When the polynucleotide of the present invention, which is a single-stranded RNA, is transferred to a cell, transcription of an RNA complementary to the target nucleotide sequence is induced in the vicinity (5' or 3' side) of the element; as a result, a double-stranded RNA having the target nucleotide sequence can be synthesized. In an embodiment, this RNA-dependent RNA synthesis (extension) reaction can proceed in the direction from the element of the present invention as the initiation site to the 3' side (this direction is the direction in the strand complementary to the RNA transferred). The double-stranded RNA undergoes various modifications, including cleavage, via intracellular siRNA synthesis mechanisms (Dicer (dcr1) and the like), so that siRNA for the target gene can be produced, and RNA interference for the target gene can be induced.

Accordingly, the term RNA-dependent RNA synthesis (extension) reaction initiation function, RNA-dependent RNA synthesis (extension) reaction priming function or RNA-dependent RNA synthesis (extension) reaction induction potential can be used herein interchangeably with "RNA interference induction potential".

Additionally, with respect to the polynucleotide of the present invention, the number of copies of the RNA interference induction element of the present invention present in one polynucleotide chain is not subject to limitation; only one copy of the RNA interference induction element may be present in one polynucleotide chain, or plural copies of the RNA interference induction element may be present in one polynucleotide chain as connected in tandem. Using plural copies of the RNA interference induction element as connected in tandem, more potent RNA interference induction potential can be obtained. When plural copies of the RNA interference induction element are used as connected in tandem, the number of copies of the RNA interference induction element connected is not subject to limitation, as long as RNA interference induction potential for the target gene can be obtained; the number of copies is, for example, 2 to 50 copies, preferably 2 to 20 copies, and more preferably 2 to 10 copies. In view of the ease of polynucleotide connecting procedures and other factors, the number of copies is preferably about 2 to 5 copies.

When plural copies of RNA interference induction element are used as connected in tandem, the nucleotide sequences of the individual units of the RNA interference induction element may be identical or not. The units of the RNA interference induction element may be connected adjacently (not via a spacer region), or may be connected via a spacer region. Although the length of the spacer region is not subject to limitation, as long as the individual constituents, from the target nucleotide sequence to the plural copies of the RNA interference induction element connected, can be stably present without interruption in one polynucleotide chain, and RNA interference induction potential for the target gene can be exhibited, it is preferably at most 10 Kbp, for example, 5 Kbp or less, 3 Kbp or less, 1 Kbp or less, 500 bp or less, 200 bp or less, 100 bp or less, 50 bp or less, or 25 bp or less. The nucleotide sequence that constitutes the spacer region is not subject to limitation, and may be an optionally chosen sequence.

3. Vector Harboring RNA Interference Induction Element (I)

In one aspect, the present invention provides a vector harboring the above-described RNA interference induction element of the present invention (the vector of the present invention (I)). Using the vector, it is easily possible to induce RNA interference and produce a siRNA for a desired target gene.

The term "vector" as used herein refers to a nucleic acid construct capable of transferring a target polynucleotide sequence to a target cell. Examples of such vectors include those capable of self-replication in host cells such as prokaryotic cells, yeast, animal cells, plant cells, insect cells, animal individuals, and plant individuals, or those capable of being incorporated in chromosome.

The kind of vector is not subject to limitation, and an appropriate vector can be optionally selected according to the intended use, the kind of target cells and the like. Useful vectors include, but are not limited to, plasmid vectors (*Escherichia coli*-derived plasmids (e.g., pBR322, pBR325, pUC12, pUC13), *Bacillus subtilis*-derived plasmids (e.g., pUB110, pTP5, pC194), yeast-derived plasmids (e.g., pSH19, pSH15, pAU001) and the like), bacteriophages such as lambda phage, viral vectors (animal viruses such as retrovirus, vaccinia virus, and baculovirus, and the like) and the like.

With respect to the vector of the present invention (I), the number of copies of the RNA interference induction element of the present invention present in one vector, like the above-described polynucleotide of the present invention, is not subject to limitation; only one copy of the RNA interference induction element may be present in one vector, or plural copies of the RNA interference induction element may be present in one vector as connected in tandem. When plural copies of the RNA interference induction element are used as connected in tandem, the range of the copy number of the RNA interference induction element connected is the same as the above-described polynucleotide of the present invention. When plural copies of the RNA interference induction element are used as connected in tandem, the nucleotide sequences of the individual units of the RNA interference induction element may be identical or not. The units of the RNA interference induction element may be connected adjacently (not via a spacer region), or may be connected via a spacer region. The range of the length of the spacer region, and the nucleotide sequence that constitutes the spacer region are the same as the above-described polynucleotide of the present invention.

In a preferred mode, the vector of the present invention (I) further comprises a promoter, which promoter is preferably connected to the RNA interference induction element of the present invention so that the expression of the element can be controlled. Hence, the promoter can be connected to the element and placed in the vector so that the RNA interference induction element of the present invention can be contained in the transcript (RNA) that can be produced by the function of the promoter.

The term "promoter" as used herein refers to a region in DNA that determines the initiation site for gene transcription and directly regulates the frequency thereof, and is usually a nucleotide sequence to which RNA polymerase binds to initiate the transcription.

Although the promoter may be placed at any position in the vector, as long as the expression of the RNA interference induction element of the present invention can be controlled, the promoter is preferably bound to the 5' side of the RNA interference induction element of the present invention because the promoter is usually located about 20 to 30 bp upstream (5' side) of the transcription initiation point. Additionally, the RNA interference induction element of the present invention is preferably located downstream (3' side) of the transcription initiation point defined by the promoter.

The kind of promoter is not subject to limitation, and an appropriate promoter can be optionally selected according to the intended use, the kind of target cells and the like. Useful promoters include pol I promoters, pol II promoters, pol III promoters and the like. When used in animal cells, the SRα promoter, the SV40 promoter, the LTR promoter, the CMV promoter, the HSV-TK promoter and the like can be used. When used in *Escherichia coli*, the trp promoter, the lac promoter, the recA promoter, the λPL promoter, the lpp promoter, the T7 promoter and the like can be used. When used in yeast, the PHO5 promoter, the PGK promoter, the GAP promoter, the ADH promoter, the NMT1 promoter and the like can be used. When used in insect cells, the polyhedrin promoter, the P10 promoter and the like can be used. Additionally, when in vitro transcription is performed, the SP6, T3, and T7 promoters and the like can be used.

In another preferred mode, the vector of the present invention (I) can further comprise at least one cloning site, which cloning site can be connected to the element so that RNA interference induction potential for a target gene can be exhibited when a nucleotide sequence (target nucleotide sequence) comprising at least 15 continuous nucleotides present in the nucleotide sequence that encodes the transcript of the target gene or a sequence complementary thereto is inserted to the site. By inserting a desired target gene and the like to the cloning site, it is easily possible to induce RNA interference and produce a siRNA for the desired target gene.

A cloning site generally means a continuous nucleotide sequence comprising one kind or more of restriction enzyme recognition sequence for incorporating an exogenous gene. The cloning site preferably comprises one kind or more of restriction enzyme recognition sequence that forms a cohesive end upon cleavage with restriction enzyme. The aforementioned restriction enzyme recognition sequence present in the cloning site is preferably a unique restriction enzyme sequence that presents in the vector only at one position. The cloning site is preferably a multiple-cloning site comprising plural restriction enzyme recognition sequences.

Additionally, the cloning site may be connected adjacently to the RNA interference induction element of the present invention (not via a spacer region), or may be connected via a spacer region, as long as RNA interference induction potential for the target gene can be exhibited when the target nucleotide sequence is inserted to the site. Although the length of the spacer region is not subject to limitation, as long as the individual constituents, from the target nucleotide sequence to the RNA interference induction element, can be stably present without interruption in one vector (or transcript), and RNA interference induction potential for the target gene can be exhibited, when the target nucleotide sequence is inserted to the cloning site, it is preferably at most 10 Kbp, for example, 5 Kbp or less, 3 Kbp or less, 1 Kbp or less, 500 bp or less, 200 bp or less, 100 bp or less, 50 bp or less, or 25 bp or less. The nucleotide sequence that constitutes the spacer region is not subject to limitation, and may be an optionally chosen sequence.

Although the cloning site may be connected to any of the 5' and 3' sides of the RNA interference induction element of the present invention, as long as RNA interference induction potential for the target gene can be exhibited when the target nucleotide sequence is inserted in the site, it is preferably connected to the 5' side.

Additionally, the vector in this mode can further harbor a promoter, in addition to the cloning site, which promoter can be joined to the element or the cloning site so that the expression of the RNA interference induction element of the present invention and cloning site can be controlled. Accordingly, the promoter that can be harbored in the vector can be connected to the element or the cloning site and placed in the vector so that the RNA interference induction element of the present invention and the cloning site can be present in the transcript (RNA) that can be produced by the function of the promoter. Hence, in the transcript that can be produced by the function of the promoter, the cloning site is joined to the RNA interference induction element of the present invention so that RNA interference induction potential for the target gene can be exhibited when the target nucleotide sequence is inserted to the site.

Although the promoter may be placed at any position in the vector, as long as the expression of the RNA interference induction element of the present invention and the cloning site can be controlled, the promoter is preferably bound to the 5' side of the RNA interference induction element of the present invention and the cloning site because the promoter is usually located about 20 to 30 bp upstream (5' side) of the transcription initiation point. Additionally, the RNA interference induction element of the present invention and the cloning site are preferably located downstream (3' side) of the transcription initiation point defined by the promoter. Because the cloning site is preferably connected to the 5' side of the RNA interference induction element of the present invention, it is more preferable that the promoter, the cloning site, and the RNA interference induction element be placed in the order of 5'-promoter-cloning site-RNA interference induction element-3'.

The promoter used may be the same as that described above.

The vector of the present invention (I) may further harbor a terminator, an enhancer, a selection marker (genes that confer resistance to drugs such as tetracycline, ampicillin, kanamycin, hygromycin, and phosphinothricin, genes that compensate for auxotrophic mutations, genes that encode fluorescent proteins, and the like) and the like.

The term "terminator" as used herein refers to a sequence located downstream of the region that encodes a transcribable gene (nucleotide sequence), and involved in transcription termination and polyA sequence addition in DNA transcription to mRNA. Terminators are known to participate in the stability of mRNA and influence the amount of gene expressed. The term "enhancer" as used herein refers to a nucleotide sequence used to increase the expression efficiency for an objective gene. Such enhancers are well known to those skilled in the art. Although plural enhancers can be used, a single enhancer may be used, or no enhancers may be used.

4. Vector Harboring RNA Interference Induction Element (II)

In another aspect, the present invention provides a vector harboring the above-described polynucleotide of the present invention (the vector of the present invention (II)). Using the vector, it is easily possible to induce RNA interference and produce a siRNA for a target gene.

Applicable modes of vector are the same as the vector of the present invention (I) described above.

In a preferred mode, the vector of the present invention further harbors a promoter, which promoter is preferably joined to the polynucleotide of the present invention so that the expression of the polynucleotide can be controlled. Accordingly, the above-described polynucleotide of the present invention, which is a single-stranded RNA, can be produced as the transcript (RNA) by the action of the promoter that can be present in the vector.

Although the promoter may be placed at any position in the vector, as long as the expression of the polynucleotide of the present invention can be controlled, the above-described promoter is preferably bound to the 5' side of the polynucleotide of the present invention because promoters are usually located about 20 to 30 bp upstream (5' side) of the transcription initiation point. Additionally, the polynucleotide of the present invention is preferably located downstream (3' side) of the transcription initiation point defined by the promoter. Because the target nucleotide sequence is preferably connected to the 5' side of the RNA interference induction element in the polynucleotide of the present invention, it is more preferable that the promoter, the target nucleotide sequence, and the RNA interference induction element be placed in the order of 5'-promoter-target nucleotide sequence-RNA interference induction element-3'.

The kind of promoter used may be the same as that of the vector of the present invention (I) described above. Additionally, the vector in this mode can also further harbor a terminator, an enhancer, a selection marker and the like as described above.

5. Cell Incorporating the Polynucleotide or the Vector of the Present Invention

In one aspect, the present invention provides a cell incorporating the above-described polynucleotide or the vector of the present invention (the cell of the present invention (I)).

The cell used in the present invention may be derived from any organism (prokaryotic organisms, eukaryotic organisms and the like). Prokaryotic organisms include bacteria such as *Escherichia coli* and *Salmonella* and the like. Eukaryotic organisms include fungi (molds, mushrooms, yeasts (fission yeast, budding yeast and the like) and the like), plants (monocotyledons, dicotyledons and the like), animals (invertebrates, vertebrates and the like) and the like. Invertebrates include nematodes, crustaceans (insects and the like) and the like. Vertebrates include hagfishes, lampreys, chondrichthians, osteichthians, amphibians, reptiles, birds, mammals and the like. Examples of mammals include monotremes, marsupials, edentates, dermapterans, chiropters, carnivores, insectivores, proboscideans, perissodactyles, artiodactyles, tubulidentata, squamatas, sirenians, cetaceans, primates, rodents, lagomorphs and the like. Rodents include mice, rats and the like. Examples of primates include chimpanzees, Japanese macaques, humans and the like.

Polynucleotide transfer into the cell may be achieved by any technique; examples include transformation, transduction, transfection and the like. These techniques for transferring nucleic acid molecules are well known and in common use in the art, and are described in, for example, Ausubel F. A. et al. eds. (1988), Current Protocols in Molecular Biology, Wiley, New York, N.Y.; Sambrook J. et al. (1987), Molecular Cloning: A Laboratory Manual, 2nd Ed. and 3rd edition, Cold Spring Harbor Laboratory Press, Cold Spring Harbor, N.Y., Bessatsu Jikken Igaku, Experimental Methods in Gene Transfer & Expression Analysis, Yodosha Co., Ltd., 1997 and elsewhere. Polypeptide transfer can be confirmed using the methods described herein, such as Northern blotting and Western blot analysis, or other known techniques in common use.

Additionally, any method of vector transfer can be used, as long as it comprises transferring a polynucleotide to a cell as described above; examples include transfection, transduction, transformation and the like (e.g., calcium phosphate method, liposome method, DEAE-dextran method, electroporation method, method using particle gun (gene gun) and the like).

To obtain a stable transformant cell incorporating a polynucleotide or a vector, for example, a polynucleotide or a vector incorporating a selection marker may be used, and the cell may be cultured by a method suitable for the selection marker. For example, when the selection marker is a gene that confers drug resistance to a selection drug lethal to the host cell, the cell incorporating the polynucleotide or the vector may be cultured using a medium supplemented with the drug. Examples of useful combinations of a drug resistance gene and a selection drug include a combination of an ampicillin resistance gene and ampicillin, a combination of a neomycin resistance gene and neomycin, a combination of a hygromycin resistance gene and hygromycin, a combination of a blasticidin resistance gene and blasticidin S, and the like. When the selection marker is a gene that encodes a fluorescent protein (GFP, YFP and the like), a cell of high fluorescence intensity may be selected from among the cells incorporating the polynucleotide or the vector using a cell sorter and the like.

6. Method of Producing Cell Wherein the Expression of Target Gene is Suppressed

In one aspect, the present invention provides a method of producing a cell wherein the expression of a target gene is suppressed, which comprises a step for transferring the above-described polynucleotide of the present invention, or a vector harboring the polynucleotide, into cells, and a step for selecting a cell incorporating the polynucleotide or the vector. The present invention also provides a method of suppressing the expression of a target gene, which comprises a step for transferring the above-described polynucleotide of the present invention, or a vector harboring the polynucleotide, into a cell. By transferring the above-described polynucleotide of the present invention or a vector harboring the polynucleotide into a cell, a siRNA for the target gene is produced, RNA interference for the target gene is induced, and the expression of the target gene is suppressed.

The cell used here may be the above-described cell with a described target gene expressed therein. The polynucleotide or the vector transfer to the cell can be achieved using the same methods as those described above.

In a preferred mode, the polynucleotide of the present invention, which is a single-stranded RNA wherein the target nucleotide sequence is connected to the 5' side of the RNA interference induction element, is transferred into a cell. As a result, a siRNA for the target gene is produced, RNA interference for the target gene is induced, and the expression of the target gene is suppressed.

In another preferred mode, the above-described vector of the present invention harboring a promoter, by which promoter the polynucleotide of the present invention, which is a single-stranded RNA wherein the target nucleotide sequence is connected to the 5' side of the RNA interference induction element, can be produced as the transcript, is transferred into a cell. A promoter that can act in the objective cell is selected as appropriate. When the vector is transferred into a cell, the polynucleotide of the present invention, which is a single-stranded RNA wherein the target nucleotide sequence is connected to the 5' side of the RNA interference induction element, is produced as the transcript. As a result, a siRNA for the target gene is produced, RNA interference for the target gene is induced, and the expression of the target gene is suppressed.

Selection of cells incorporating the polynucleotide of the present invention or a vector harboring the polynucleotide can be achieved by a commonly known method, such as hybridization or PCR with a nucleotide sequence specific for the polynucleotide of the present invention or a vector harboring the polynucleotide as the probe or primer; when a polynucleotide or vector provided with a selection marker is used, selection can be performed using the phenotype by the selection marker as the index.

Additionally, it may be confirmed whether or not the expression of a target gene is suppressed in the cell incorporating the polynucleotide of the present invention or a vector harboring the polynucleotide. This confirmation can be achieved by, for example, comparing the expression of the target gene in the cells incorporating the polynucleotide of the present invention or a vector harboring the polynucleotide with the expression of the target gene in a control cell not incorporating the polynucleotide of the present invention or a vector harboring the polynucleotide. Although any method can be used for this confirmation, a commonly known method such as hybridization or PCR is available. Alternatively, a phenotype difference in cells between the presence and absence of the expression of the target gene may also be examined. The presence or absence of siRNA for the target gene may also be examined by hybridization and the like.

A cell incorporating the polynucleotide of the present invention or a vector harboring the polynucleotide as described above is a cell having the expression of the target gene suppressed (knockdown cells). Such "knockdown cell" include both a cell wherein the expression of the target gene has been completely suppressed and a cell wherein the expression of the target gene has been reduced, though not completely been suppressed. Conventionally, such cell has been generated by deleting or modifying the target gene or the control region thereof; it is possible to produce a cell wherein the expression of the target gene is suppressed, by a simple method comprising transferring the polynucleotide of the present invention or a vector harboring the polynucleotide into cells, and selecting the cell incorporating the same, without modifying the target gene in a chromosome, using the present invention. The knockdown cell thus generated can be used as a research material for functional analysis of the target gene; additionally, a cell wherein the expression of a causal gene for a disease as the target gene is suppressed can be used as a disease model cell and the like. Additionally, by transferring the polynucleotide of the present invention or a vector harboring the polynucleotide to a germ cell or multipotent stem cell, and allowing the target gene knockdown germ cell or the target gene knockdown multipotent stem cell to develop into an individual organism or tissue, it is also possible to generate a target gene knockdown animal, a disease model animal, a target gene knockdown tissue and the like. The present invention also includes the above-described knockdown cell produced by the present invention; furthermore, individual organisms retaining the above-described polynucleotide of the present invention or the vector (e.g., a target gene knockdown non-human animal and the like), a tissue (a target gene knockdown tissue) and the like are also included in the present invention. As examples of the above-described organism in the present invention, mice, rats, rabbits, cattle, horses, swine, sheep, monkeys, or chimpanzees and the like can be mentioned.

Additionally, by obtaining (isolating, purifying, or the like) a siRNA from the cell incorporating the polynucleotide of the present invention or a vector harboring the polynucleotide, a siRNA for a target gene can be produced. Accordingly, the present invention provides a method of producing a siRNA for a target gene, which comprises a step for transferring the polynucleotide of the present invention or a vector harboring the polynucleotide into a cell, and a step for obtaining a siRNA for the target gene from the cell incorporating the aforementioned polynucleotide or the vector. siRNA isolation and purification from a cell can be performed by a method known per se such as RNA purification or gel filtration column chromatography.

7. RNA Interference Inducing Agent

Using the polynucleotide of the present invention or a vector harboring the polynucleotide as described above, it is possible to induce RNA interference for a desired target gene and suppress the expression of the gene. Accordingly, the present invention provides an RNA interference inducing agent comprising the above-described polynucleotide of the present invention or a vector harboring the polynucleotide.

The agent of the present invention can comprise an optionally chosen carrier, for example, a physiologically acceptable carrier, in addition to an effective amount of the above-described polynucleotide of the present invention or a vector harboring the polynucleotide.

Examples of the physiologically acceptable carrier include, but are not limited to, excipients such as sucrose, starch, mannitol, sorbitol, lactose, glucose, cellulose, talc, calcium phosphate and calcium carbonate; binders such as cellulose, methylcellulose, hydroxypropylcellulose, polypropylpyrrolidone, gelatin, acacia, polyethylene glycol, sucrose and starch; disintegrants such as starch, carboxymethylcellulose, hydroxypropyl starch, sodium-glycol-starch, sodium hydrogen carbonate, calcium phosphate and calcium citrate; lubricants such as magnesium stearate, aerosil, talc and sodium lauryl sulfate; flavoring agents such as citric acid, menthol, glycyrrhizin ammonium salt, glycine and orange flour; preservatives such as sodium benzoate; sodium hydrogen sulfite, methyl paraben and propyl paraben; stabilizers such as citric acid, sodium citrate and acetic acid; suspending agents such as methylcellulose, polyvinylpyrrolidone and aluminum stearate; dispersing agents such as surfactants; diluents such as water, physiological saline and orange juice; base waxes such as cacao butter, polyethylene glycol and refined kerosene; and the like.

To promote the transfer of the polynucleotide and the vector into cells, the agent of the present invention can further comprise a nucleic acid transfer reagent. When the active ingredient is a viral vector, particularly a retroviral vector, retronectin, fibronectin, polybrene or the like can be used as the transfection reagent. When the active ingredient is a polynucleotide, a plasmid vector or the like, a cationic lipid such as lipofectin, lipfectamine, DOGS (transfectam; dioctadecylamidoglycylspermine), DOPE (1,2-dioleoyl-sn-glycero-3-phosphoethanolamine), DOTAP (1,2-dioleoyl-3-trimethylammoniumpropane), DDAB (dimethyldioctadecylammonium bromide), DHDEAB (N,N-di-n-hexadecyl-N,N-dihydroxyethylammonium bromide), HDEAB (N-n-hexadecyl-N,N-dihydroxyethylammonium bromide), polybrene, or poly(ethyleneimine) (PEI) can be used.

Because the expression of a desired target gene can be suppressed using the agent of the present invention, it is possible to treat or prevent a disease by, for example, administering the agent of the present invention to a patient to suppress the gene expression that causes the disease. Furthermore, the agent of the present invention is also useful as a reagent for investigating the function of a target gene.

8. Gene Knockdown Polynucleotide Library

In one aspect, the present invention provides a gene knockdown polynucleotide library comprising a plurality of polynucleotides each of which comprises a nucleotide sequence comprising at least 15 continuous nucleotides present in the nucleotide sequence that encodes each of the transcripts of a plurality of gene or a sequence complementary thereto, wherein each nucleotide sequence is connected to the RNA interference induction element of the present invention so that RNA interference induction potential for the gene can be exhibited. Each polynucleotide present in the library may be harbored in a vector. Each polynucleotide or vector present in the library of the present invention can be in the same mode as the above-described polynucleotide of the present invention or a vector harboring the polynucleotide. By transferring the library of the present invention to a cellular population, it is possible to search for a functional gene.

"A plurality of genes" can be selected as appropriate according to the intended purpose and the like; for example, an assembly of genes expressed in desired cells, tissues and the like (gene library) and the like can be used.

The library of the present invention can, for example, be prepared by synthesizing a cDNA library by an ordinary method, and functionally connecting the cDNA library to the RNA interference induction element of the present invention. A commonly used method of synthesizing a cDNA library comprises synthesizing a cDNA by a reverse transcriptase reaction using oligodT (oligodeoxythymidine) or a random hexamer as the primer with an mRNA purified from total RNA extracted from tissue and the like as the template, enzymatically treating the reaction product cDNA to render it a double-stranded DNA, and binding the DNA to a cloning vector (Molecular Cloning: A Laboratory Manual-Second Edition, 1989).

In this case, it is easily possible to prepare the library of the present invention by, for example, using the above-described vector of the present invention, wherein the individual constituents are placed in the order of 5'-promoter-cloning site-RNA interference induction element-3', and inserting a cDNA library to the cloning site. Additionally, when the library is transferred to a cellular population, and the insert is expressed by the action of the promoter in the vector, a single-stranded RNA wherein the RNA interference induction element is bound to the 3' side of the cDNA sequence of any one gene in the cDNA library or a sequence complementary thereto is expressed in each cell, and a siRNA for the gene is produced by the action of the element. Subsequently, this siRNA inhibits the expression of the gene to alter the cell function or phenotype.

The present invention provides a method of screening for a functional gene, which comprises a step for analyzing the phenotype of a cellular population incorporating the above-described gene knockdown nucleotide library, a step for isolating a cell with a change in the phenotype from the cellular population, and a step for obtaining a functional gene on the basis of the target nucleotide sequence in the polynucleotide or the vector transferred to the isolated cell.

In the above-described method, a cellular population incorporating a gene knockdown nucleotide library can be produced in the same manner as described above.

Subsequently, the phenotype of the cellular population is analyzed. This phenotype analysis can be performed by, for example, comparing the phenotype with that of a population of control cells not incorporating the gene knockdown nucleotide library. This phenotype includes not only those occurring on the cell surface, but also, for example, intracellular changes and the like. Subsequently, cells with a desired change in phenotype are isolated from the cellular population. Isolation of the cells can be performed using a means known per se such as a cell sorter.

It is highly likely that a polynucleotide (or vector) that produces a siRNA capable of suppressing the expression of a functional gene has been transferred to a cell with a change in phenotype. Hence, to screen for the functional gene, for example, a probe and primer are constructed on the basis of the target nucleotide sequence in the polynucleotide or the vector transferred in this isolated cell. Then, hybridization or PCR is performed using this probe or primer; cloning of the functional gene can thereby be performed. Additionally, on the basis of the target nucleotide sequence, a functional gene can also be searched for in a database.

Using the above-described method, the "forward genetic" approach with a step of isolating a cell with a mutated phenotype of interest from a cellular population having random knockdown mutated phenotypes, and cloning the causal gene, can be applied to the cells of higher organisms, so that the methodology of genetic analysis improves dramatically.

9. Template for the RNA-Dependent RNA Synthesis Reaction

As described above, when a single-stranded RNA comprising the RNA interference induction element of the present invention is transferred to cells, the RNA acts favorably as a template for an RNA-dependent RNA synthesis reaction, and transcription of an RNA complementary to the RNA transferred is induced in the vicinity of the element (5' or 3' side). Hence, the RNA interference induction element of the present invention is capable of functioning as an "RNA-dependent RNA synthesis reaction induction element."

Accordingly, in still another aspect, the present invention provides a template for an RNA-dependent RNA synthesis reaction comprising the RNA-dependent RNA synthesis reaction induction element of the present invention. The template is an RNA.

The template of the present invention further comprises "a target template sequence," in addition to the above-described RNA-dependent RNA synthesis reaction induction element. "A target template sequence" refers to a nucleotide sequence intended to cause a synthesis reaction of an RNA complementary thereto, and can be chosen optionally. The target template sequence is connected to the RNA-dependent RNA synthesis reaction induction element so that a synthesis reaction of an RNA complementary thereto is caused when an RNA-dependent RNA synthesis reaction is performed using the template of the present invention.

The length of the target template sequence is not subject to limitation, as long as a synthesis reaction of an RNA complementary to the sequence can be caused when an RNA-dependent RNA synthesis reaction is performed using the template of the present invention.

Additionally, the target template sequence may be connected adjacently to the RNA-dependent RNA synthesis reaction induction element of the present invention (not via a spacer region), or may be connected via a spacer region, as long as a synthesis reaction of an RNA complementary to the sequence can be caused when an RNA-dependent RNA synthesis reaction is performed using the template of the present invention. Although the length of the spacer region is not subject to limitation, as long as the individual constituents, from the target template sequence to the element, can be stably present without interruption in one polynucleotide chain, and as long as a synthesis reaction of an RNA complementary to the target template sequence can be caused, it is preferably at most 10 Kbp, for example, 5 Kbp or less, 3 Kbp or less, 1 Kbp or less, 500 bp or less, 200 bp or less, 100 bp or less, 50 bp or less, or 25 bp or less. The nucleotide sequence that constitutes the spacer region is not subject to limitation, and may be an optionally chosen sequence.

The target template sequence may be connected to any of the 5' and 3' sides of the RNA-dependent RNA synthesis reaction induction element of the present invention, as long as a synthesis reaction of an RNA complementary to the target template sequence can be caused. However, the target template sequence is preferably connected to the 5' side of the RNA-dependent RNA synthesis reaction induction element of the present invention, because an RNA-dependent RNA synthesis reaction is caused with dependence on RNA-dependent RNA polymerase from the vicinity of the element toward the 3' side (this is the direction in the strand complementary to the template) when the template of the present invention is used.

Additionally, with respect to the template of the present invention, the number of copies of the RNA-dependent RNA synthesis reaction induction element present in one template chain is not subject to limitation; only one copy of the element may be present in one template chain, or plural copies of the element may be present in one template chain as connected in tandem. Using plural copies of the element as connected in tandem, more potent RNA-dependent RNA synthesis reaction induction potential can be obtained. When plural copies of the element are used as connected in tandem, the number of copies of the element connected is not subject to limitation, as long as a synthesis reaction of an RNA complementary to the target template sequence can be caused; the number of copies is, for example, 2 to 50 copies, preferably 2 to 20 copies, and more preferably 2 to 10 copies. In view of the ease of polynucleotide connecting procedures and other factors, the number of copies is preferably about 2 to 5 copies.

When plural copies of RNA-dependent RNA synthesis reaction induction element are used as connected in tandem, the nucleotide sequences of the individual units of the element may be identical or not. The units of the element may be connected adjacently (not via a spacer region), or may be connected via a spacer region. Although the length of the spacer region is not subject to limitation, as long as the individual constituents, from the target template sequence to the plural copies of the RNA-dependent RNA synthesis reaction induction element connected, can be stably present without interruption in one polynucleotide chain, and as long as a synthesis reaction of an RNA complementary to the target template sequence can be caused, it is preferably at most 10 Kbp, for example, 5 Kbp or less, 3 Kbp or less, 1 Kbp or less, 500 bp or less, 200 bp or less, 100 bp or less, 50 bp or less, or 25 bp or less. The nucleotide sequence that constitutes the spacer region is not subject to limitation, and may be an optionally chosen sequence.

10. A Vector Capable of Expressing a Template for the RNA-Dependent RNA Synthesis Reaction In still another aspect, the present invention provides a vector capable of expressing the above-described template of the present invention (the vector of the present invention (III)). Using the vector, it is easily possible to produce a template of the present invention and induce an RNA-dependent RNA synthesis reaction in a cell.

Applicable modes of vector are the same as the vector of the present invention (I) or (II) described above.

In a preferred mode, the vector of the present invention (III) further harbors a promoter, which promoter is preferably joined to a region encoding the template of the present invention so that the expression of the template can be controlled. Accordingly, the template of the present invention can be produced as the transcript (RNA) by the action of the promoter that can be present in the vector.

Although the promoter may be placed at any position in the vector, as long as the expression of the template of the present invention can be controlled, the above-described promoter is preferably bound to the 5' side of the region encoding the template of the present invention because promoters are usually located about 20 to 30 bp upstream (5' side) of the transcription initiation point. Additionally, the region encoding the template of the present invention is preferably located downstream (3' side) of the transcription initiation point defined by the promoter. Because the target template sequence is preferably connected to the 5' side of the RNA-dependent RNA synthesis reaction induction element of the present invention in the template of the present invention, it is more preferable that the promoter, the target template sequence, and the RNA-dependent RNA synthesis reaction induction element be placed in the order of 5'-promoter-target template sequence-RNA-dependent RNA synthesis reaction induction element-3'.

The kind of promoter used may be the same as that of the vector of the present invention (I) or (II) described above. Additionally, the vector in this mode can also further harbor a terminator, an enhancer, a selection marker and the like as the vector of the present invention (I) or (II) described above.

11. Cell Incorporating the Vector Capable of Expressing the Template for the RNA-Dependent RNA Synthesis Reaction In still another aspect, the present invention provides a cell incorporating the above-described vector of the present invention (III) (the cell of the present invention (II)).

The kinds of cells useful in the present invention are the same as those mentioned with respect to the above-described cell of the present invention (I). Because the template of the present invention is expressed from the vector transferred in the cell, making it possible to cause an RNA-dependent RNA synthesis reaction based on the template, it is preferable to use a cell having RNA-dependent RNA polymerase.

The cell of the present invention (II) can be produced using the above-described method of vector transfer.

12. Method of Synthesizing an RNA

In still another aspect, the present invention provides a method of synthesizing an RNA comprising the steps shown below:

(a) a step for providing a template for an RNA-dependent RNA synthesis reaction comprising the RNA-dependent RNA synthesis reaction induction element of the present invention;

(b) a step for bringing the template of (a) in contact with RNA-dependent RNA polymerase to cause the RNA-dependent RNA synthesis reaction.

For example, when the RNA synthesis reaction is performed in vitro, the template of the present invention for an RNA-dependent RNA synthesis reaction is prepared using a nucleic acid synthesizer, in vitro transcription and the like (step (a)). The template obtained is brought into contact with RNA-dependent RNA polymerase under conditions allowing the RNA-dependent RNA synthesis reaction, to cause the RNA-dependent RNA synthesis reaction and an RNA complementary to the target template sequence is synthesized (step (b)). The RNA-dependent RNA synthesis reaction is preferably performed in an appropriate buffer solution supplemented with a substrate essential to the RNA-dependent RNA synthesis reaction (e.g., NTPs and the like).

A method of synthesizing an RNA in cells is also encompassed in the scope of the present invention. For example, the template of the present invention for an RNA-dependent RNA synthesis reaction is expressed by transferring the above-described vector of the present invention (III) into a cell having RNA-dependent RNA polymerase (step (a)). The resulting template comes into contact with the RNA-dependent RNA polymerase in the cell to cause the RNA-dependent RNA synthesis reaction and an RNA complementary to the target template sequence is synthesized (step (b)).

Using the method of the present invention, it is possible to produce an RNA complementary to a desired target template sequence from an RNA having the sequence. For example, when using the nucleotide sequence of the reverse transcript of a structural gene as the target template sequence in the template used in the step (a), an RNA-dependent RNA synthesis reaction occurs, resulting in the forward transcript (RNA) of the structural gene. Therefore, provided that the reaction has been performed in a cell, the translation product (protein) of the structural gene will be produced from the forward transcript of the structural gene.

The present invention is hereinafter described in more detail by means of the following Examples, which, however, are not to be construed as limiting the scope of the present invention.

EXAMPLES

Example 1

Fission Yeast Centromeric siRNA is Derived from the Vicinity of SIRE

The fission yeast wild type strains ($h^-$ and $h^{90}$) used were common laboratory strains 972 and 968. Mutants of the RNAi apparatus ($\Delta$ago1, $\Delta$rdp1, and $\Delta$dcr1) were prepared by replacing the SPCC736.11, SPAC6F12.09, and SPCC584.10c genes with the G418 resistance gene, respectively.

The otr repeats in the left arm of the first chromosome centromere of fission yeast were divided into eight portions (regions 1 to 8), and small-molecule RNAs in the fission yeast were detected by Northern blotting using regions 1 to 8 as the probes (FIG. 1).

The probe of region 1 corresponds to the base number 19814-21497 region of the cosmid SPAP7G5 (GenBank accession number: AL353014), the probe of region 2 corresponds to the EcoRI-HindIII fragment region of the centromeric plasmid pRS140, the probe of region 3 corresponds to the HindIII-AatII fragment region of the centromeric plasmid pRS140, the probe of region 4 corresponds to the AatII-BamHI fragment region of the centromeric plasmid pRS140, the probe of region 5 corresponds to the BamHI-SpeI fragment region of the centromeric plasmid pRS140, the probe of region 6 corresponds to the SpeI-KpnI fragment region of the centromeric plasmid pRS140, the probe of region 7 corresponds to the KpnI-HindIII fragment region of the centromeric plasmid pRS140, and the probe of region 8 corresponds to the HindIII-EcoRI fragment region of the centromeric plasmid pRS140.

As a result, when probes 2, 6 and 7 were used, siRNA accumulation was detected specifically in RNAs extracted from the wild type strains ($h^-$ and $h^{90}$). No such accumulation was observed in any RNA extracted from the mutants ($\Delta$ago1, $\Delta$rdp1, and $\Delta$dcr1) of the RNAi apparatus.

Although it is not present in pRS140, a sequence comprising the RNA interference induction element of the present invention (hereinafter referred to as SIRE) comprising SEQ ID NO:1 or a sequence homologous thereto is inserted in the probe 2 region of the ordinary dh repeat unit of the fission yeast (see FIG. 2). With this in mind, two probes surrounding the insertion site were prepared (probes 2.1 and 2.2), and Northern blotting was performed in the same way; a larger amount of siRNA was found with probe 2.2 (FIG. 1). This agrees with the difference in the amount detected between probes 6 and 7 relative to SIRE.

Figure 2:
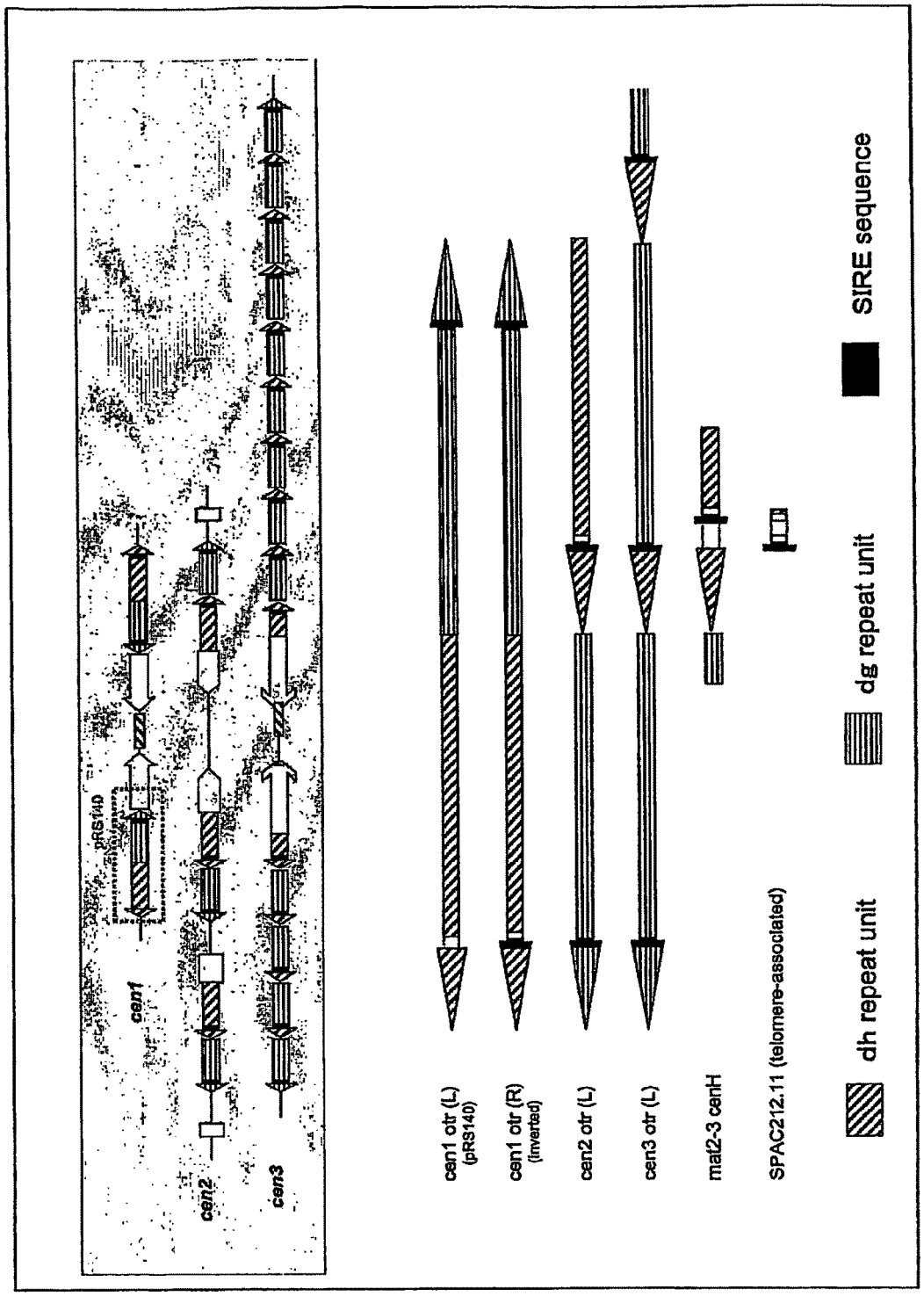
FIG. 2 shows the schematic structures of the centromere DNAs of the three chromosomes of fission yeast.

FIG. 2 shows the schematic structures of the centromere DNAs of the three chromosomes of fission yeast. The upper panel against the gray background illustrates the entire centromere, the lower panel shows the features of the otr repeat, which is a common unit shared by the three centromeres, and the homologous portions to sequences other than the centromeres. SIRE is present in dh units other than the dh unit contained in pRS140. In the third chromosome centromere otr, in particular, dg and dh often occur in mixture to form a single repeat unit with SIRE as the transition point. Additionally, a otr-like region containing SIRE is also found in the cenH and SPAC212.11 of mat2-3.

Example 2

Figure 3:
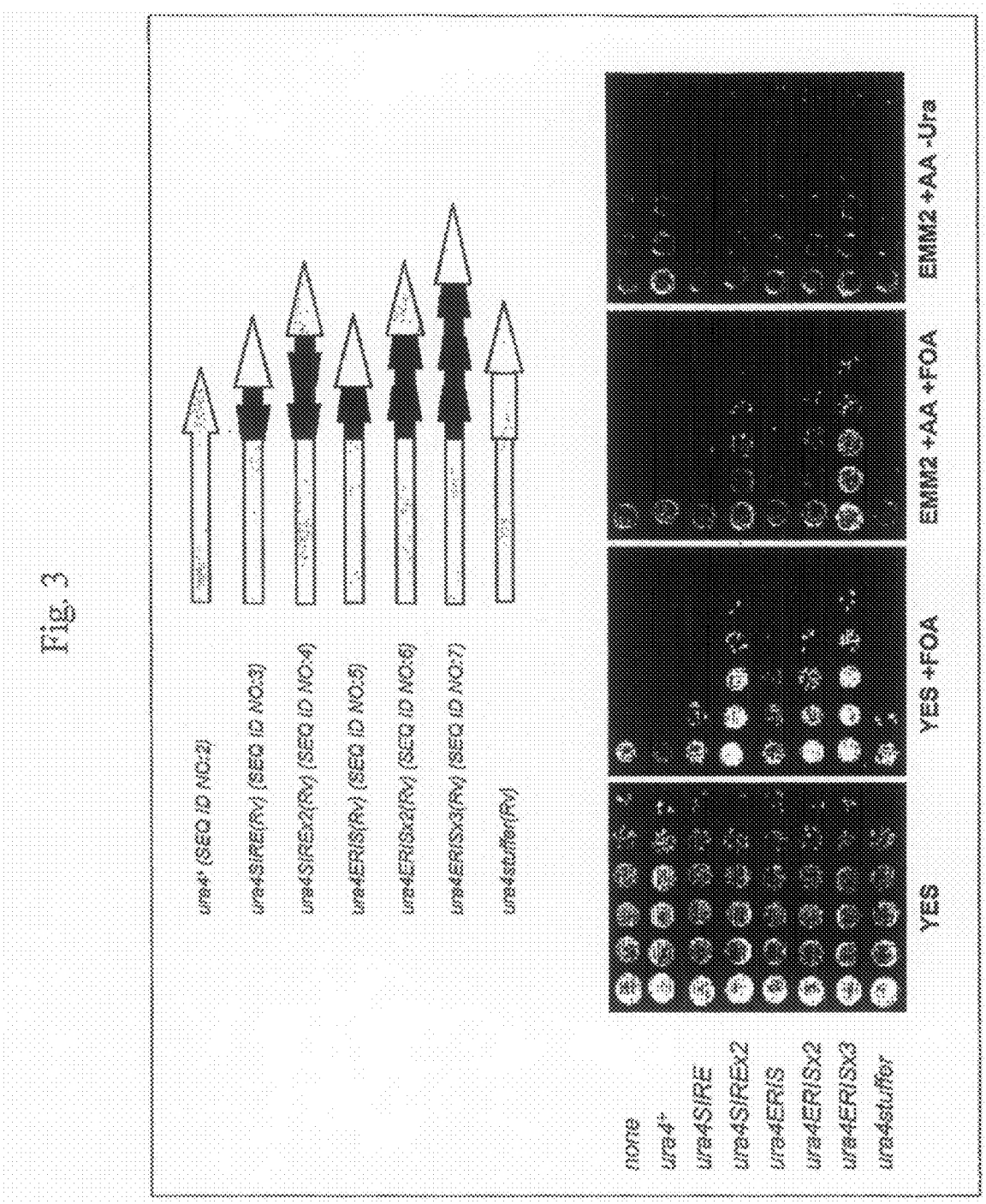
FIG. 3 shows the suppression of the expression of the endogenous ura4$^+$ gene by the expression of the SIRE-incorporating ura4 gene.

Expression of SIRE-Incorporating ura4 Gene Suppresses the Expression of Endogenous ura4$^+$ Gene One to three SIRE units comprising the sequence of SEQ ID NO:1 were inserted to the ura4$^+$ gene under the control of the nmt1 promoter in the pAU001 vector in two directions (differentially designated as SIRE for the insertion in the forward direction, and as ERIS for the insertion in the reverse direction), and expressed in a fission yeast wherein the endogenous ura4$^+$ gene is functioning normally, to examine the effect (FIG. 3). The ura4$^+$ gene used was the genome sequence (a region covering the initiation codon, the ORF full-length and the terminator sequence) of the ura4$^+$ gene (SEQ ID NO:2). In SEQ ID NO:2, the region of base numbers 1 to 795 corresponds to ORF. SIRE or ERIS was inserted to the EcoRV restriction site at the 679 position in SEQ ID NO:2. Nucleotide sequences functionally connected to the nmt1 promoter are shown by SEQ ID NO:2 to 7, respectively.

A liquid culture of each yeast strain expressing the insert was serially diluted 10 fold and spotted onto each medium at six dilution rates, and this was followed by incubation at 33° C. and examination for viability. Referring to FIG. 3, panel YES shows control results obtained by spotting to a complete medium; panel YES+FOA shows results obtained with a complete medium supplemented with 5-FOA, a drug that makes the strains expressing the ura4$^+$ gene to be incapable of growing; panel EMM2+AA+FOA shows results obtained with a synthetic medium supplemented with 5-FOA; in the latter two panels, the ratio of cells with suppressed expression of the ura4$^+$ gene is shown. EMM2+AA-Ura is a synthetic medium lacking uracil; in which only cells expressing the ura4$^+$ gene can grow.

In the control cases without expression (none) or with the expression (ura4$^+$) of the ura4$^+$ gene, the endogenous ura4$^+$ gene remained normally expressed, and no growth on the FOA medium was observed. When the SIRE-incorporating ura4 gene was expressed, cells that also grow on the FOA medium were identified (ura4SIRE(RV)). This demonstrates that the expression of endogenous ura4$^+$ gene was suppressed by the expression of the SIRE-incorporating ura4 gene. Additionally, the number of cells that grow on the FOA medium increased (ura4SIREx2(RV)) as the number of SIRE units inserted increased. This demonstrates that the expression of endogenous ura4$^+$ gene is more potently suppressed as the number of SIRE units inserted increases. Furthermore, even when the ura4 gene, incorporating ERIS, a sequence complementary to SIRE, was expressed, cells that also grow on the FOA medium were identified, demonstrating the suppression of the expression of the endogenous ura4$^+$ gene (ura4ERIS (RV)). Additionally, it was demonstrated that, as with SIRE, the number of cells that grow on the FOA medium increased, and the expression of the endogenous ura4$^+$ gene was more potently suppressed, as the number of ERIS units inserted increased (ura4ERISx2(RV) and ura4ERISx3(RV)). Such an effect was not observed when an irrelevant stuffer was inserted (ura4stuffer(RV)).

Example 3

A Ura4-Derived siRNA is Detected in the Strain Expressing ura4ERISx2

Figure 4:
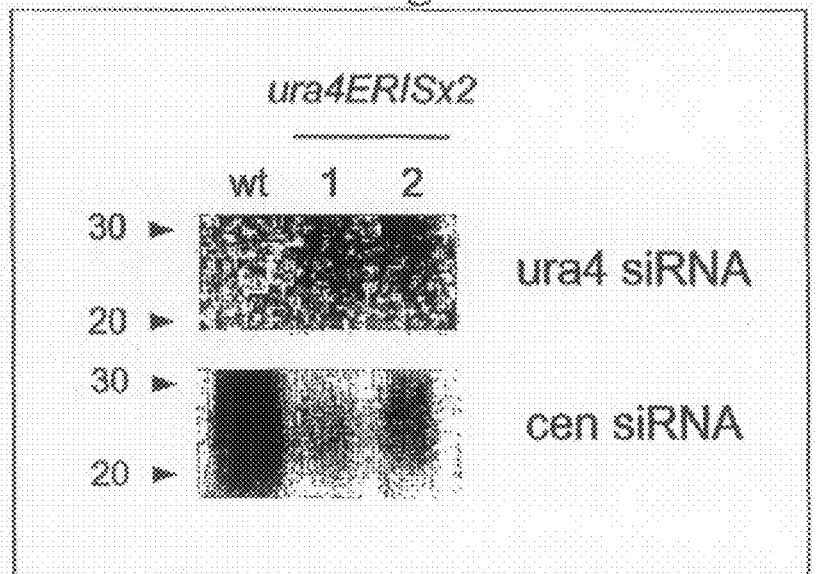
FIG. 4 shows the presence of a ura4-derived siRNA in the strain expressing the SIRE-incorporating ura4 gene.

RNA was extracted from a wild type strain wherein the endogenous ura4$^+$ gene was normally functioning, and a strain expressing ura4ERISx2 (a strain wherein the ura4$^+$ gene incorporating two ERIS units was expressed under the control of the nmt1 promoter), and analyzed for ura4-derived siRNA by Northern blotting to detect small-molecule RNA. The probe used was the ORF region of the ura4$^+$ gene. For the strain expressing ura4ERISx2, two cultures were used for RNA extraction: liquid culture (1) obtained with an ordinary complete medium, and liquid culture (2) under selection conditions of a complete medium supplemented with 5-FOA. The results are shown in FIG. 4.

A band not found in the wild type strain was detected in the two RNAs extracted from the strain expressing ura4ERISx2. This demonstrates the presence of an ura4-derived siRNA in the strain expressing ura4ERISx2. For control, the results with centromere-derived siRNA (probe 6 used) are shown in the lower panel. Although the amount detected was variable, centromere-derived siRNA was identified in all samples. From this finding, it can be understood that the detection of ura4-derived siRNA only in the strain expressing ura4ERISx2 and its non-detection in the wild strain is not due to the differences in the amount of total RNA used in the experiment.

Example 4

A ura4-Derived siRNA is Detected in the Strain Expressing ura4ERISx3

Figure 5:
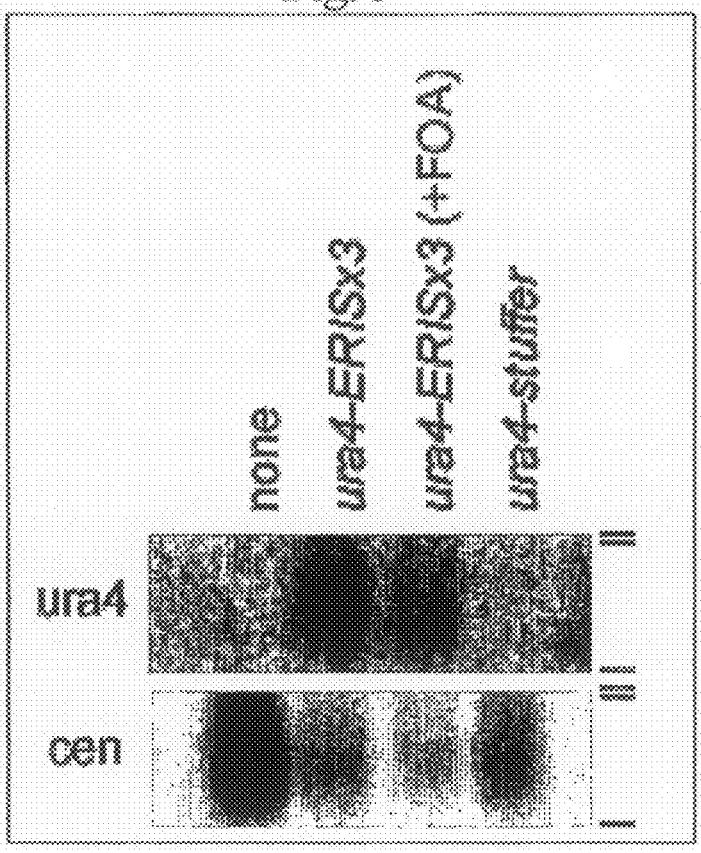
FIG. 5 shows the presence of a ura4-derived siRNA in the strain expressing the SIRE-incorporating ura4 gene.

RNA was extracted from a wild type strain wherein the endogenous ura4$^+$ gene was normally functioning, and a strain expressing ura4ERISx3 (a strain wherein the ura4$^+$ gene incorporating three ERIS units was expressed under the control of the nmt1 promoter), and analyzed for ura4-derived siRNA by Northern blotting to detect small-molecule RNA. The probe used was the ORF region of the ura4$^+$ gene. For the strain expressing ura4ERISx3, two cultures were used for RNA extraction: liquid culture obtained with an ordinary complete medium, and liquid culture (+FOA) under selection conditions of a complete medium supplemented with 5-FOA. The results are shown in FIG. 5.

A band not found in the wild strain was detected in the two RNAs extracted from the strain expressing ura4ERISx3. Such a band was not found in the RNA extracted from the ura4stuffer-expressing strain incorporating an irrelevant stuffer. This demonstrates the presence of an ura4-derived siRNA specifically in the strain expressing ura4ERISx3. For control, the results with centromere-derived siRNA (probe 6 used) are shown in the lower panel. Although the amount detected was variable, centromere-derived siRNA was identified in all samples. From this finding, it can be understood that the detection of ura4-derived siRNA only in the strain expressing ura4ERISx3 and its non-detection in the wild strain is not due to the differences in the amount of total RNA used in the experiment.

Example 5

Figures 6, 7:
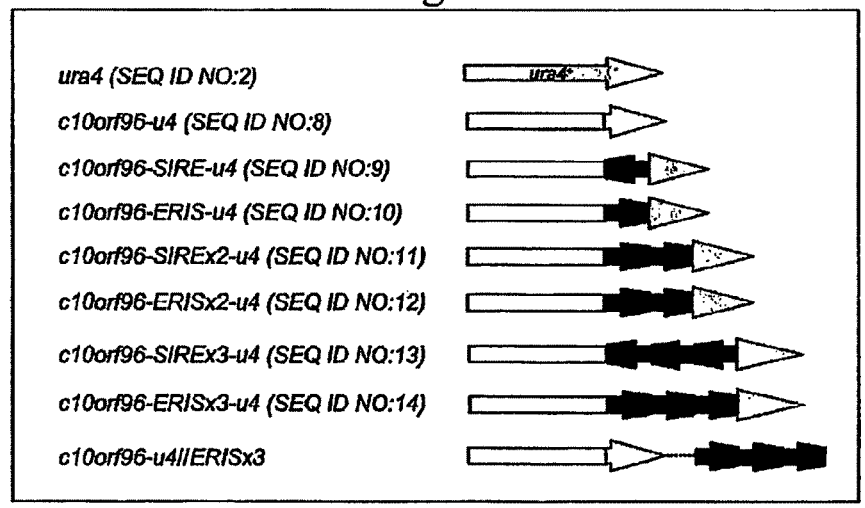
FIG. 6 shows the RNA interference mechanism dependency of the suppression of the expression of ura4$^+$ by SIRE.
FIG. 7 schematically shows the constructs used in Example 6.
Figure 8A:
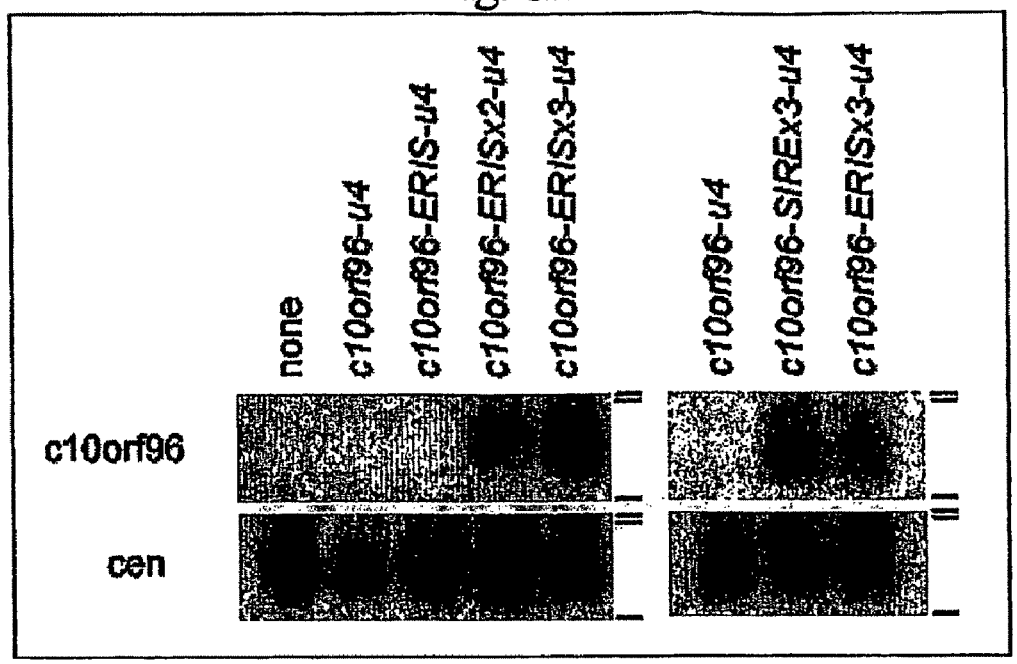
FIG. 8(A-D) shows the results of Northern blotting detection of a c10orf96- or ura4-derived siRNA in the strain expressing the c10orf96-ura4 fusion gene incorporating SIRE or ERIS. SIRE or ERIS induced a c10orf96-derived siRNA (A to D). A siRNA derived from c10orf96 connected to the 5' side of ERIS was preferentially induced (B). In Δeri1, an siRNA derived from the c10orf96 gene was observed even when the c10orf96-ura4 fusion gene incorporating one unit of SIRE or ERIS was expressed (C and D).
Figure 8B:
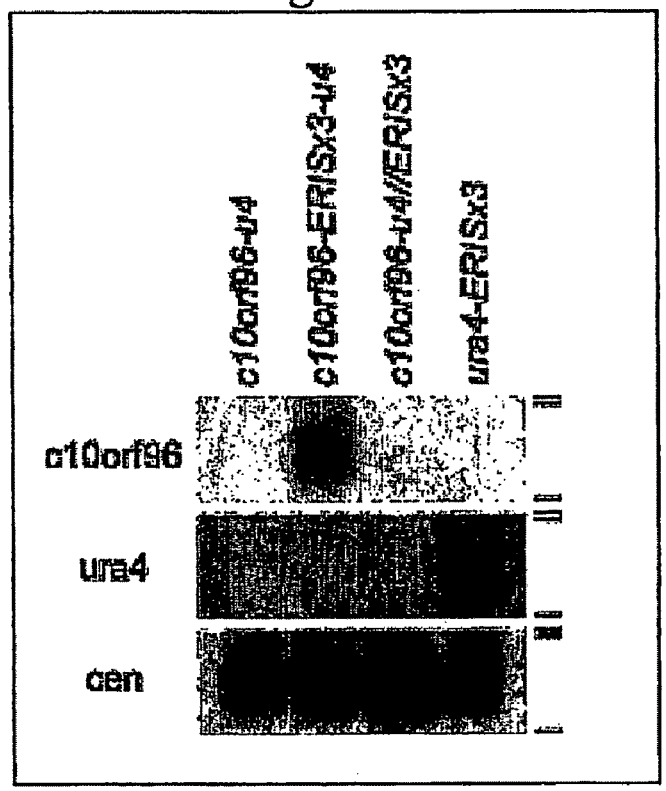
Figure 8C:
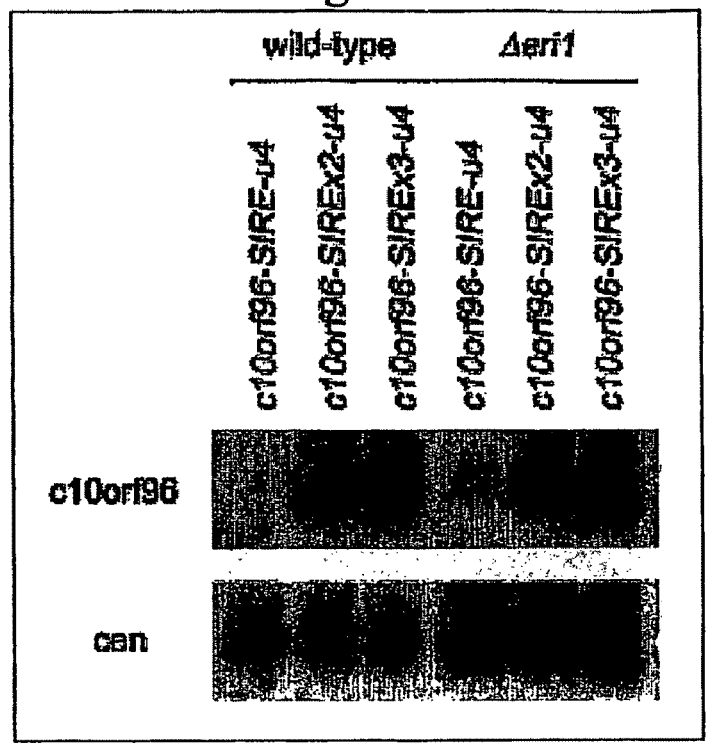
Figure 8D:
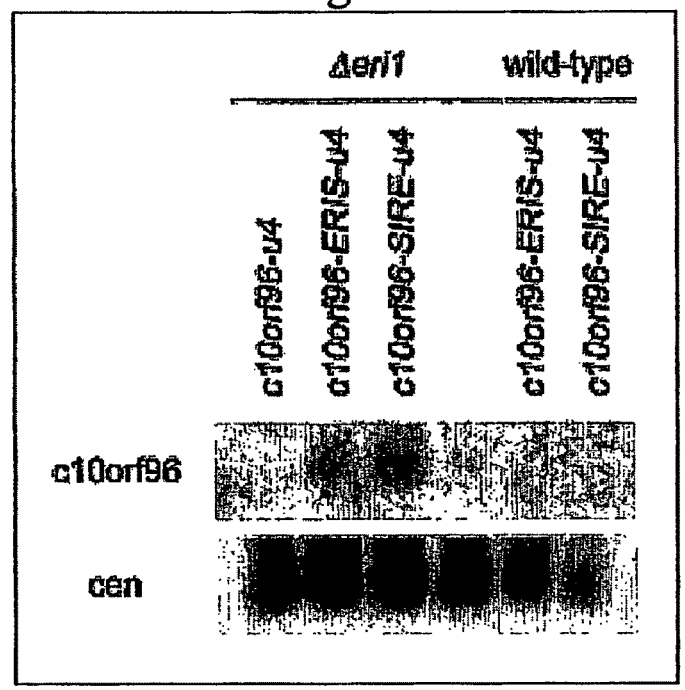

Suppression of Endogenous ura4$^+$ Gene by SIRE-Incorporating ura4 Depends on RNA Interference Mechanism As in Example 2, in a fission yeast wild type strain (wt) wherein the endogenous ura4$^+$ gene is normally functioning, and strains wherein incorporating mutations of the RNAi apparatus (Δdcr1, Δago1, and Δrdp1), the ura4$^+$ gene incorporating two ERIS units under the control of the nmt1 promoter was expressed, and their effects were examined. The results are shown in FIG. 6.

In the wild type strain (wt), because of the normal function of the ura4$^+$ gene, no growth was observed on the 5-FOA-containing medium. In the strain expressing ura4 incorporating two units of ERIS (wt ura4ERISx2), this endogenous ura4$^+$ gene underwent expression suppression; growth on the 5-FOA medium was observed. It was revealed, however, that the growth on the 5-FOA medium was inhibited in the strains incorporating the mutations of the RNAi apparatus (Δdcr1 ura4ERISx2, Δago1 ura4ERISx2, and Δrdp1 ura4ERISx2).

These findings demonstrate that the suppression of the expression of ura4$^+$ by SIRE (or ERIS) depends on RNA interference mechanism.

Example 6 siRNA Induction for Human Gene by SIRE and siRNA Induction Potential with One Copy of SIRE Detectable in a Strain Lacking siRNA-Decomposing Enzyme One to three units of SIRE or ERIS were inserted to the fusion site of the human-cDNA(c10orf96)-ura4$^+$ fusion gene under the control of the nmt1 promoter in the pREP1 vector (FIG. 7), and the gene was expressed in a wild type or eri1-deleted mutant (Δeri1) strain of fission yeast. The nucleotide sequences of the inserts in the individual constructs are shown by SEQ ID NO:8 to 14, respectively. Eri1 is a ribonuclease that decomposes siRNA, and Δeri1 was prepared by replacing and hence destroying the SPBC30B4.08 gene with the hygromycin resistance gene. RNA was extracted from the fission yeast incorporating each vector, and examined for c10orf96- or ura4-derived siRNA by Northern blotting to detect small-molecule RNA. The probe used was the ORF region in the cDNA of the c10orf96 gene or full length of ura4 gene (SEQ ID NO:2). The results are shown in FIG. 8.

When the c10orf96-ura4$^+$ fusion gene incorporating two or three units of SIRE or ERIS was expressed in the wild type strain, siRNA derived from the c10orf96 gene was detected (A). This result indicates that siRNA induction by SIRE is not limited to the genes of fission yeast. Northern blotting on the same cell-extracted RNA with the ura4 as the probe revealed that siRNA of the ura4 gene portion, which is placed on the 3' side from SIRE, was not detected (B). For control, the results of Northern blotting on the centromere-derived siRNA of each sample with the probe 6 are also shown. These results suggest that SIRE may preferentially induce siRNA from a sequence on the 5' side of SIRE in the template transcript.

Even when the c10orf96-ura4+ fusion gene incorporating one unit of SIRE or ERIS was expressed in the wild strain, siRNA derived from the c10orf96 gene was little detected (A, C, and D). In Δeri1, in contrast, siRNA derived from the c10orf96 gene was detected not only when a plurality of units of SIRE were inserted, but also when one unit of SIRE or ERIS was inserted (C and D). This is attributable to an increase in siRNA recovery efficiency as a result of deletion of the siRNA-decomposing enzyme from the host cell. These results suggest that even a single copy of SIRE and ERIS exhibits siRNA induction potential.

Example 7

SIRE Induces RNA Reverse Transcription with RNA Template

Figure 9:
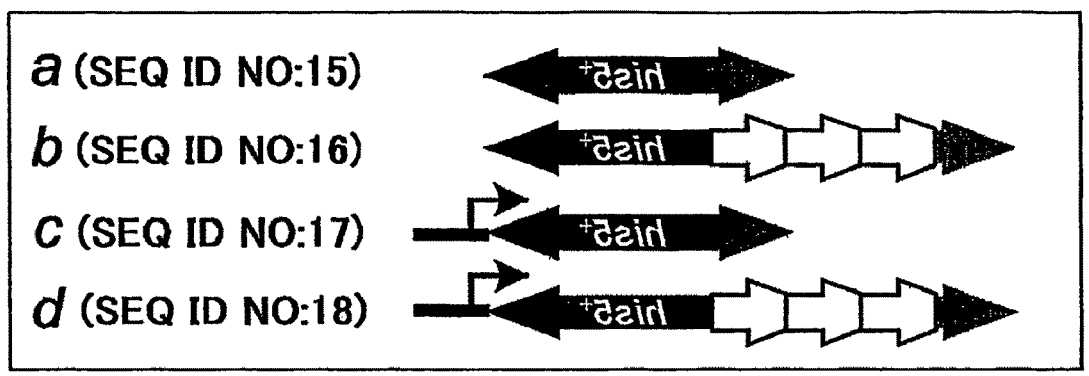
FIG. 9 schematically shows the constructs used in Example 7.

The his5+ gene was connected to the pAU001 vector in the reverse orientation under the control of the nmt1 promoter, and three units of SIRE were connected in tandem to the 3' side thereof (FIG. 9, d). The construct obtained (construct-d) was transferred to a wild type fission yeast, and its effect was examined. The his5+ gene is a histidine synthesis gene. The nucleotide sequences of the inserts of the constructs-a to -d are shown by SEQ ID NO:15 to 18, respectively.

A liquid culture of the fission yeast was serially diluted 10 fold, spotted onto each medium at six dilution rates and incubated at 33° C. to examine their viability. EMM2+aa is a complete medium and represents control values of the amount spotted. EMM2+aa-His is a histidine-free medium, in which only the strain expressing the his5+ gene is capable of growing.

Figure 10:
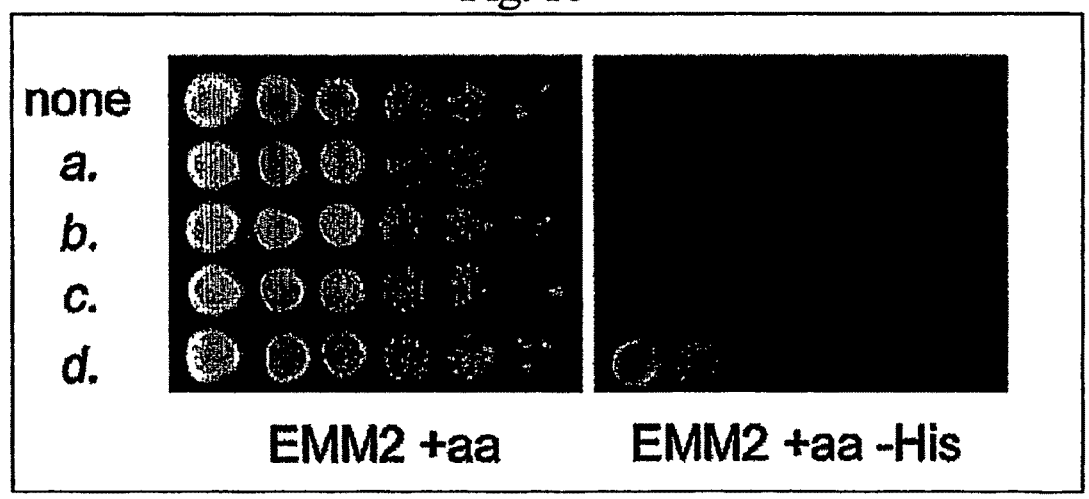
FIG. 10 shows the growth of the fission yeasts on complete medium (EMM2+aa) or histidine-free medium (EMM2+aa- His). In the figure, lanes a to d corresponds to the constructs of a to d in FIG. 9. The growth of the strain incorporating the construct-d is observed on the histidine-free medium.

As a result, the strain incorporating the construct-d exhibited infrequent but observable growth on the EMM2+aa-His medium (FIG. 10, d). In contrast, the strains incorporating a control construct without the nmt1 promoter (FIGS. 9, a and b) or a control construct without SIRE (FIGS. 9, a and c) were incapable of growing on the EMM2+aa-His medium like the non-incorporating strain (FIG. 10, a-c).

These results show that SIRE promoted the synthesis of the forward transcript of the his5+ gene from the reverse transcript of the his5+ gene, that his5+functional protein was produced from the forward transcript, and that the strain incorporating the construct-d acquired the ability to grow in histidine-free medium.

Figure 11:
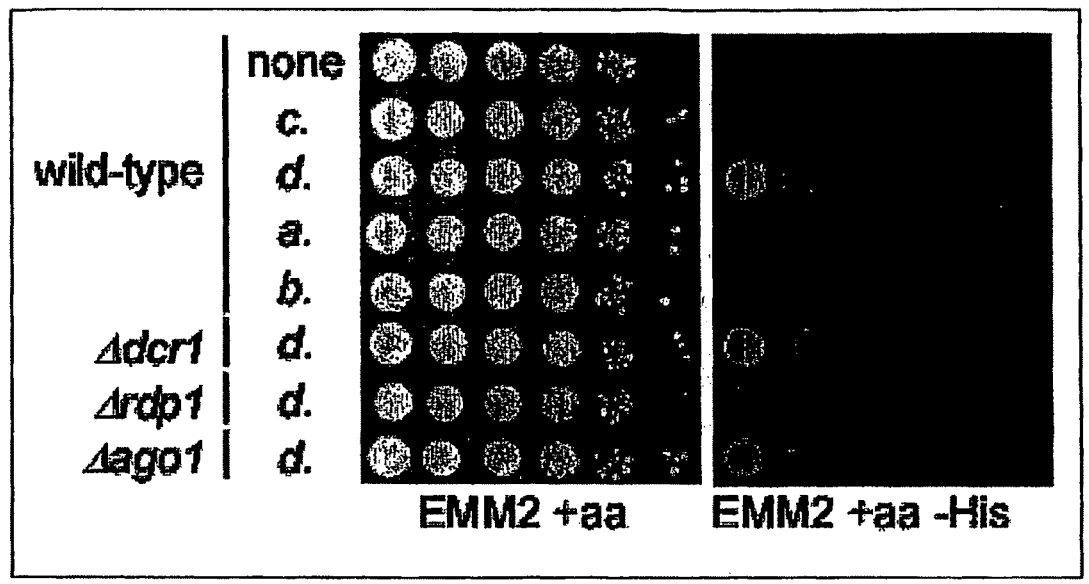
FIG. 11 shows the growth of the fission yeasts on complete medium (EMM2+aa) or histidine-free medium (EMM2+aa-His). In the figure, lanes a to d corresponds to the constructs of a to d in FIG. 9. Even when the construct-d was transferred to Δrdp1, no growth was observed on the histidine-free medium.

Furthermore, the construct-d was transferred to mutants with a mutation in the RNAi apparatus (Δdcr1, Δago1 and Δrdp1), and its effects were examined. As a result, when the construct-d was transferred to Δdcr1 or Δago1, growth on the EMM2+aa-His medium was observed as with the wild type strain. In contrast, when the construct-d was transferred to Δrdp1, i.e., a strain lacking RNA-dependent RNA polymerase (RdRP), remarkably decreased growth on the EMM2+aa-His medium was observed (FIG. 11, Δrdp1).

These results suggest that the SIRE-induced synthesis of the forward transcript from the reverse transcript of the his5+ gene is dependent on RNA-dependent RNA polymerase (RdRP).

Figure 12:
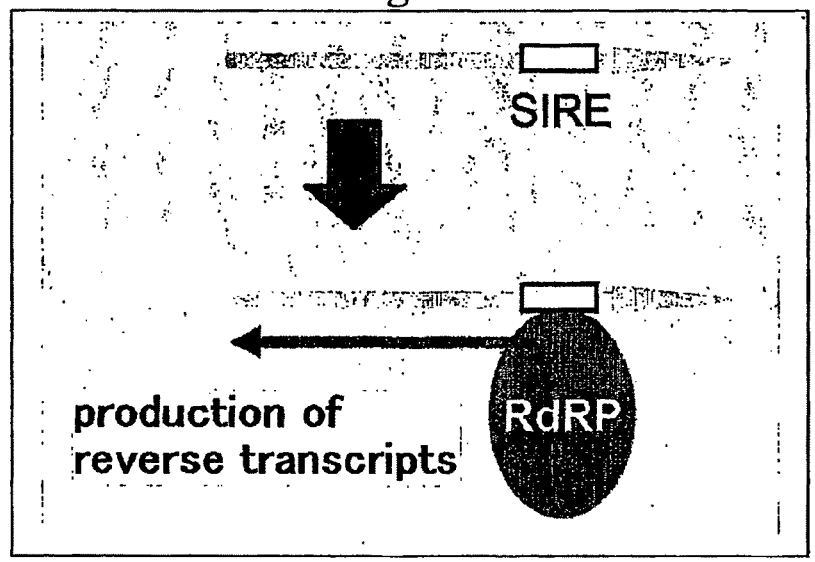
FIG. 12 schematically shows the RNA-dependent RNA reverse transcription reaction induced by SIRE.

Hence, it was demonstrated that the RNA interference induction element of the present invention possesses an activity to induce an RNA reverse transcription reaction with the RNA template, and that this activity is dependent on RdRP (FIG. 12).

Example 8

Gene-Suppressive Effect of SIRE in Human Cells

Hela cells and SVts8 cells that stably express the GFP-Cenp-A fusion protein were prepared by transferring pBabe-Hygro-EGFP-CENPA, an expression vector encoding the GFP-Cenp-A fusion protein. Cenp-A is a kind of centromere-localized protein.

Figure 13:
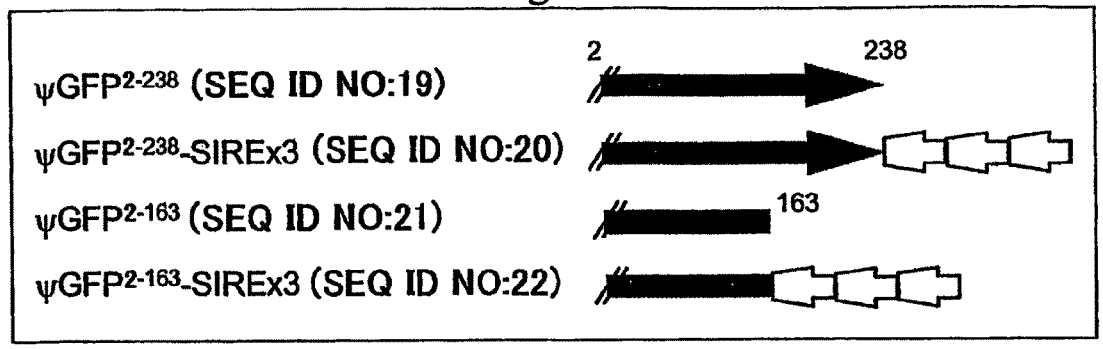
FIG. 13 schematically shows the constructs used in Example 8.

The full-length cDNA of the GFP gene mutated at the initiation codon ($\Psi GFP^{2-236}$) or a 3'-end-deleted DNA thereof ($\Psi GFP^{2-163}$) was connected to the pcDNA3 vector in the forward orientation under the control of the CMV promoter, and three units of SIRE were connected in tandem to the 3' side thereof (FIG. 13, $\Psi GFP^{2-23}$-SIREx3 and $\Psi GFP^{2-163}$-SIREx3). $\Psi GFP^{2-238}$ corresponds to the coding region for the 2-238 position amino acids of the GFP gene, and $\Psi GFP^{2-163}$ corresponds to the coding region for the 2-163 position amino acids of the GFP gene. Because all constructs undergo transcription but do not undergo translation into protein, the gene products never, by themselves, generate a fluorescent signal in the cells. Each construct obtained was transferred to the above-described GFP expressing transfectant using the calcium phosphate method and cultured for 72 hours, after which GFP fluorescence was examined under a fluorescence microscope. The nucleotide sequences of the inserts of the individual constructs are shown by SEQ ID NO:19 to 22, respectively.

Figure 14:
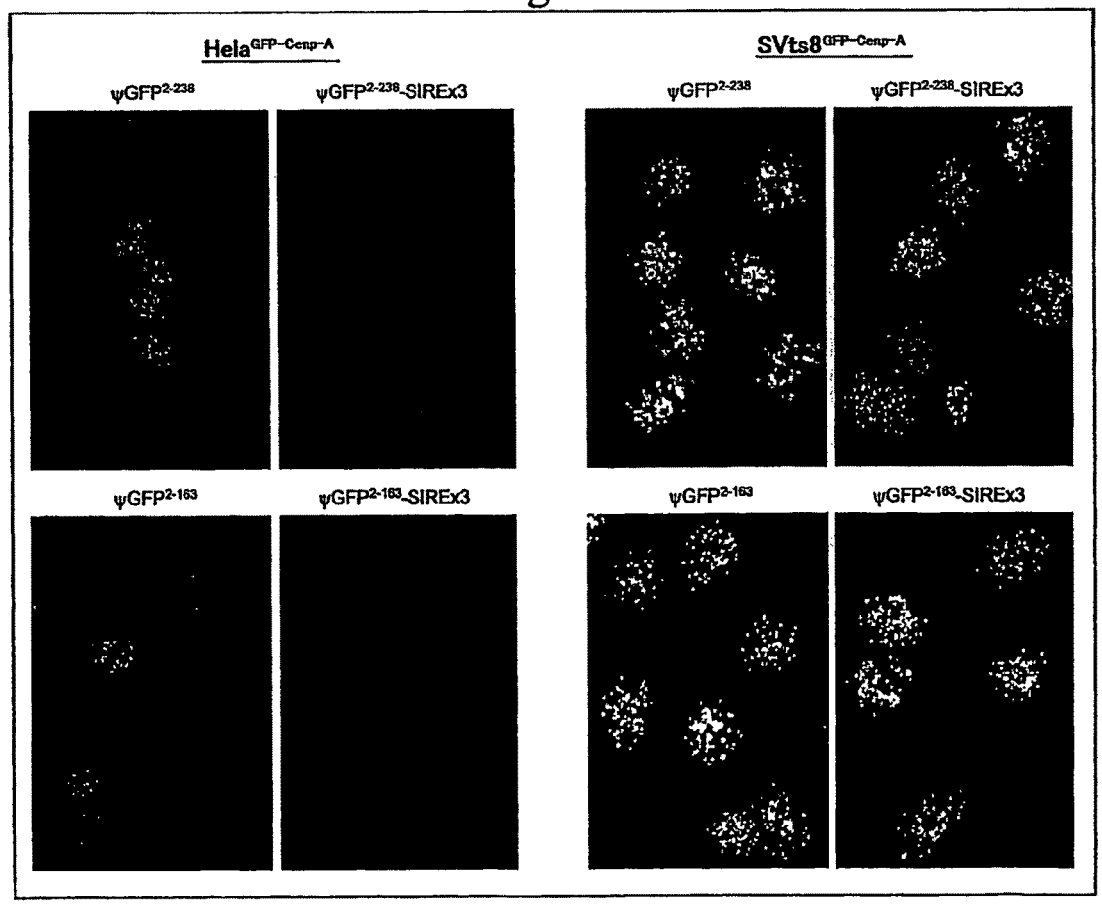
FIG. 14 shows the results of fluorescent microscopic examination of Hela cells and SVts8 cells that stably express GFP-Cenp-A. Transfer of $\Psi GFP^{2-238}$-SIREx3 or $\Psi GFP^{2-163}$-SIREx3 weakened GFP fluorescence.

As a result, when $\Psi GFP^{2-238}$-SIREx3 or $\Psi GFP^{2-163}$-SIREx3 was transferred to Hela cells or SVts8 cells expressing the GFP-Cenp-A protein, the GFP fluorescence weakened (FIG. 14). When SIRE-free control constructs (FIG. 13, $\Psi GFP^{2-238}$ or $\Psi GFP^{2-163}$) were used, no such effect was observed (FIG. 14). The bar measures 10 μm.

Figure 15:
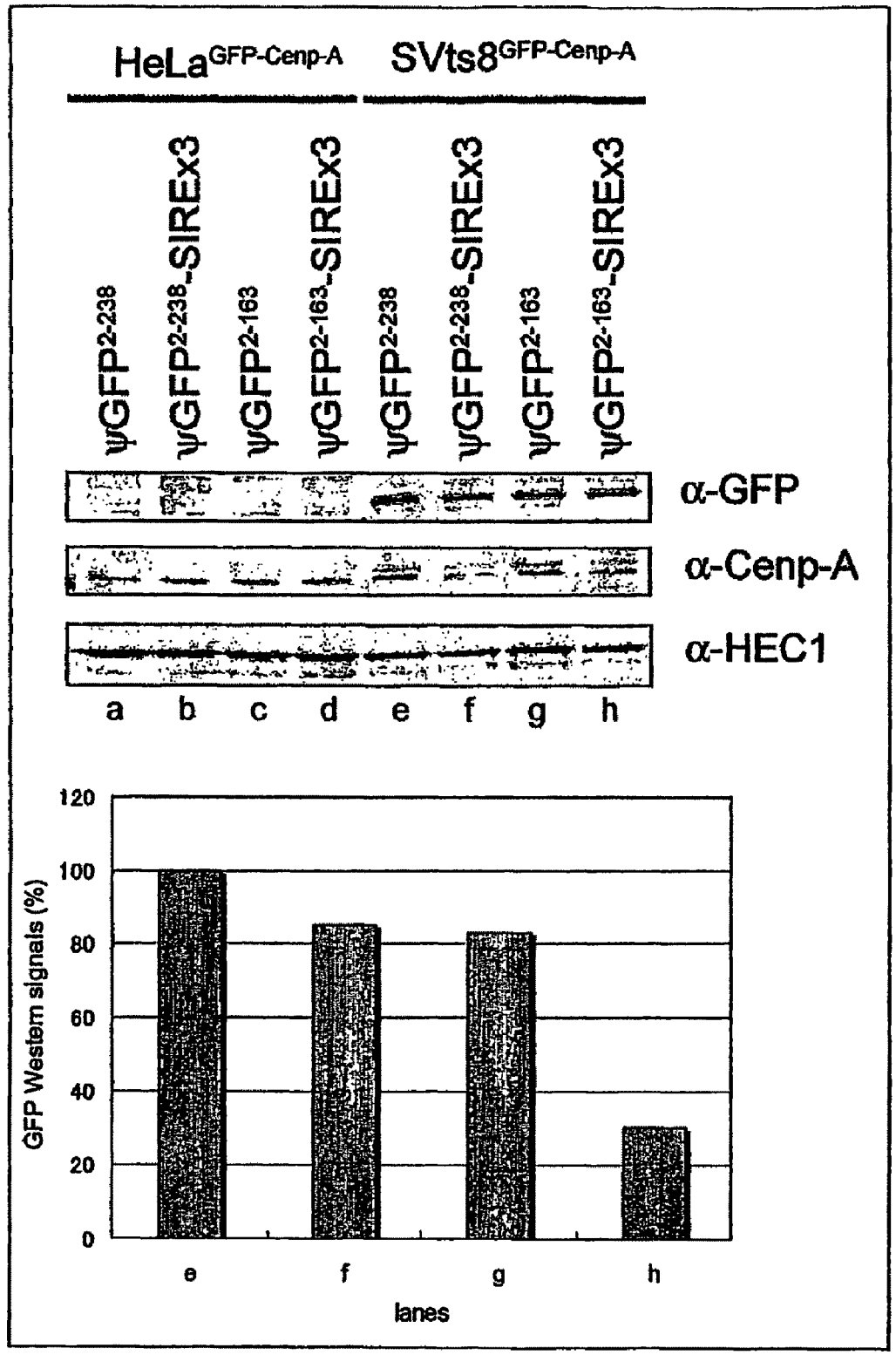
FIG. 15 shows the results of Western blotting analysis of the GFP-Cenp-A protein amount in Hela cells and SVts8 cells that stably express GFP-Cenp-A. The graph shows the relative signal intensity of GFP as standardized with HEC1. α-GFP: anti-GFP antibody, α-Cenp-A: anti-Cenp-A antibody, α-HEC1: anti-HEC1 antibody.

Lysates were prepared from these cells and the GFP-Cenp-A protein in the cells was quantified by Western blotting. The amount of GFP protein decreased with the transfer of $\Psi GFP^{2-238}$-SIREx3 or $\Psi GFP^{2-63}$-SIREx3, in agreement with the findings of the fluorescent microscopic examination (FIG. 15).

Hence, it was demonstrated that the RNA interference induction element of the present invention exhibits suppressive potential of gene expression also in mammalian cells such as human cells.

INDUSTRIAL APPLICABILITY

Using the RNA interference induction element of the present invention, it is easily possible to knock down a desired target gene, and to produce a siRNA for a desired target gene.

This application is based on a patent application No. 2005-145876 filed in Japan (filing date: May 18, 2005), the contents of which are incorporated in full herein by this reference.

The invention claimed is:

1. An isolated RNA interference induction element consisting of
   the nucleotide sequence of SEQ ID NO:1 or a sequence complementary to the full length nucleotide sequence of SEQ ID NO: 1 and with the identical length.

2. An isolated polynucleotide comprising
   i) the element of claim 1, and
   ii) a nucleotide sequence comprising at least 15 continuous nucleotides present in the nucleotide sequence that encodes the transcript of a target gene, or a sequence complementary thereto, wherein the nucleotide sequence of step ii) is connected to the element so that RNA interference induction potential for the target gene can be exhibited.

3. The isolated polynucleotide of claim 2, wherein the nucleotide sequence of step ii) is connected to the 5' side of the element.

4. The isolated polynucleotide of claim 2, which comprises plural copies of the element as connected in tandem.

5. A vector harboring plural copies of the element of claim 1 connected in tandem.

6. A vector harboring
   i) the element of claim 1, and
   ii) a promoter joined to the element so that the expression of the element can be controlled.

7. A vector harboring
   i) the element of claim 1, and
   ii) at least one cloning site connected to the element so that RNA interference induction potential for a target gene can be exhibited when a nucleotide sequence comprising at least 15 continuous nucleotides present in the nucleotide sequence that encodes the transcript of the target gene or a sequence complementary thereto is inserted to the cloning site.

8. The vector of claim 7, wherein the cloning site is connected to the 5' side of the element.

9. The vector of claim 7, which further harbors a promoter joined to the element or the cloning site so that the expression of the element and the cloning site can be controlled.

10. A vector harboring the polynucleotide of claim 2.

11. The vector of claim 10, which further harbors a promoter joined to the polynucleotide so that the expression of the polynucleotide can be controlled.

12. An isolated cell incorporating the polynucleotide of claim 2.

13. An isolated cell incorporating the vector of claim 5.

14. A method of producing a cell wherein the expression of a target gene is suppressed, which comprises a step for transferring the polynucleotide of claim 2 into cells, and a step for selecting a cell incorporating the polynucleotide.

15. A method of suppressing the expression of a target gene, which comprises a step for transferring the polynucleotide of claim 2 into cells.

16. A method of producing a siRNA for a target gene, which comprises a step for transferring the polynucleotide of claim 2 into cells, and a step for obtaining the siRNA for the target gene from the cells incorporating the polynucleotide or the vector.

17. An RNA interference inducing agent comprising the polynucleotide of claim 2.

18. A gene knockdown polynucleotide library comprising a plurality of polynucleotides, each of which comprises a nucleotide sequence comprising at least 15 continuous nucleotides present in the nucleotide sequence that encodes each of the transcripts of a plurality of genes or a sequence complementary thereto, wherein each nucleotide sequence is connected to the element of claim 1 so that RNA interference induction potential for the gene can be exhibited.

19. The library of claim 18, wherein the each polynucleotide is harbored in a vector.

20. A cellular population incorporating the library of claim 18.

21. A method of screening for a functional gene, which comprises the steps (a) to (c) below:
   (a) analyzing the phenotype of a cellular population incorporating the library of claim 18;
   (b) isolating cells with an altered phenotype from the cellular population; and
   (c) obtaining a functional gene based on a nucleotide sequence in the polynucleotide or the vector incorporated in the isolated cells.

22. An isolated RNA-dependent RNA synthesis reaction induction element consisting of the
   nucleotide sequence of SEQ ID NO:1 or a sequence complementary to the full length nucleotide sequence of SEQ ID NO:1.

23. A method of synthesizing an RNA, which comprises the steps shown below:
   (a) a step for providing a template for an RNA-dependent RNA synthesis reaction comprising the element of claim 22;
   (b) a step for bringing the template of (a) into contact with RNA-dependent RNA polymerase to cause the RNA-dependent RNA synthesis reaction.

24. An isolated gene expression suppression element consisting of the below
   nucleotide sequence of SEQ ID NO:1 or a sequence complementary to the full length nucleotide sequence of SEQ ID NO:1.

25. A method of producing a cell wherein the expression of a target gene is suppressed, which comprises a step for transferring the vector of claim 10 into cells, and a step for selecting a cell incorporating the polynucleotide or the vector.

26. A method of suppressing the expression of a target gene, which comprises a step for transferring the vector of claim 10 into cells.

27. A method of producing a siRNA for a target gene, which comprises a step for transferring the vector of claim 10 into cells, and a step for obtaining the siRNA for the target gene from the cells incorporating the polynucleotide or the vector.

28. An RNA interference inducing agent comprising the vector of claim 10.

29. An isolated cell incorporating the vector of claim 7.

30. A method of producing a cell wherein the expression of a target gene is suppressed, which comprises a step of transferring the vector of claim 7 into cells, and a step for selecting a cell incorporating the vector.

31. A method for producing siRNA for a target gene, which comprises a step for transferring the vector of claim 7 into cells, and a step for obtaining the siRNA for the target gene from the cells incorporating the vector.

32. A method of screening for a functional gene, which comprises the steps (a) to (c) below:
   (a) analyzing the phenotype of a cellular population incorporating the library of claim 20;
   (b) isolating cells with an altered phenotype from the cellular population; and
   (c) obtaining a functional gene based on a nucleotide sequence in the vector incorporated in the isolated cells.

* * * * *

SEQUENCE LISTING

<160> NUMBER OF SEQ ID NOS: 22

<210> SEQ ID NO 1
<211> LENGTH: 376
<212> TYPE: DNA
<213> ORGANISM: Artificial Sequence
<220> FEATURE:
<223> OTHER INFORMATION: Synthetic Construct; SIRE sequence

<400> SEQUENCE: 1

```
actctgaaga caacgatgtg ttttctcaag atgataacgg atctagcttc gccatcaata      60
agtatgagac aaaggagtcc atctttgatg aaacatccat ttgcctgttg tacattttg     120
caggacaacc agcctgagca caagagacat ggtgtactag actttgtgcg gaatgtctac    180
ttcaaaactt gcatctttat atctgatata tagagatata gagatataga gatatagaga    240
gaggctgatg atttataaac acaaacgata agacttgtaa catgaagttt gtcgaaaaag    300
tcaatctta aattcctttc tgaacctctc tgttatgtca gtgcttcggt attatgcttt    360
aatgcagtca cttgag                                                    376
```

<210> SEQ ID NO 2
<211> LENGTH: 1137
<212> TYPE: DNA
<213> ORGANISM: Schizosaccharomyces pombe

<400> SEQUENCE: 2

```
atggatgcta gagtatttca aagctattca gctagagctg aggggatgaa aaatcccatt      60
gccaaggaat tgttggcttt gatggaagaa aagcaaagca acttgtcagt cgcggtcgat    120
ttgacgaaga aatccgaaat cttagaattg gtagataaaa ttggacccta tgtctgtgtt    180
atcaagacac atattgacgt tgtcgaggat ttcgaccagg atatggtaga aaaactggtg    240
gccttaggta aaaagcatcg ttttcttatc tttgaggatc gcaaattcgc agacattgga    300
aataccgtca agctacaata tgcatctggt gtgtacaaaa ttgcttcttg ggctcatatc    360
acaaattgcc atacagtgcc aggcgagggt attatacaag gcctcaaaga agttggttta    420
cctttgggac gtggtctctt gcttttggct gaaatgtctt ccaaaggctc tttggctact    480
ggttcctaca cagagaaaac cttagaatgg tttgagaagc ataccgatt ttgctttggc    540
tttatagctg gtcgtcgatt tcctaaccttt caaagcgact acataactat gtcccctggt    600
atcggcttgg atgttaaagg agacgggctg ggacagcaat atcgtactcc tgaagaagtg    660
attgtaaact gcggtagcga tatcatcatt gttggtcgtg gagtctatgg agctggtcgt    720
aatcctgttg tcgaagccaa gagatataga gaagctggtg ggaaggcata tcagcaaaga    780
ctttctcagc attaaaaaaa gactaatgta aaatttttt ggttggttat tgaaaaagtc    840
gatgccttgt ttgcgtttgt tttcctaggc gttttatgtc agaaggcatt tagaattagt    900
atacaagtac tctttggtaa aattttatgt agcgactaaa atattaacta ttatagataa    960
acaccttggg aataaaaagt aatttgctat agtaatttat taaacatgct cctacaacat   1020
taccacaatc ttttctcttg gattgacatt gaataagaaa agagtgaatt tttttagact   1080
tgtaatgata actatgtaca aagccaatga aagatgtatg tagatgaatg taaaata     1137
```

<210> SEQ ID NO 3
<211> LENGTH: 1551
<212> TYPE: DNA
<213> ORGANISM: Artificial Sequence
<220> FEATURE:
<223> OTHER INFORMATION: Synthetic Construct; ura4SIRE

<400> SEQUENCE: 3

| | | |
|---|---|---|
| atggatgcta gagtatttca aagctattca gctagagctg aggggatgaa aaatcccatt | 60 |
| gccaaggaat tgttggcttt gatggaagaa aagcaaagca acttgtcagt cgcggtcgat | 120 |
| ttgacgaaga aatccgaaat cttagaattg gtagataaaa ttggacccta tgtctgtgtt | 180 |
| atcaagacac atattgacgt tgtcgaggat ttcgaccagg atatggtaga aaaactggtg | 240 |
| gccttaggta aaaagcatcg ttttcttatc tttgaggatc gcaaattcgc agacattgga | 300 |
| aataccgtca agctacaata tgcatctggt gtgtacaaaa ttgcttcttg ggctcatatc | 360 |
| acaaattgcc atacagtgcc aggcgagggt attatacaag ccctcaaaga agttggttta | 420 |
| cctttgggac gtggtctctt gcttttggct gaaatgtctt ccaaaggctc tttggctact | 480 |
| ggttcctaca cagagaaaac cttagaatgg tttgagaagc ataccgattt ttgctttggc | 540 |
| tttatagctg gtcgtcgatt tcctaacctt caaagcgact acataactat gtcccctggt | 600 |
| atcggcttgg atgttaaagg agacgggctg gacagcaat atcgtactcc tgaagaagtg | 660 |
| attgtaaact gcggtagcga tgggattaac tgcagactct gaagacaacg atgtgttttc | 720 |
| tcaagatgat aacggatcta gcttcgccat caataagtat gagacaaagg agtccatctt | 780 |
| tgatgaaaca tccatttgcc tgttgtacat ttttgcagga caaccagcct gagcacaaga | 840 |
| gacatggtgt actagacttt gtgcggaatg tctacttcaa aacttgcatc tttatatctg | 900 |
| atatatagag atatagagat atagagatat agagagaggc tgatgattta taaacacaaa | 960 |
| cgataagact tgtaacatga agtttgtcga aaagtcaat ctttaaattc ctttctgaac | 1020 |
| ctctctgtta tgtcagtgct tcggtattat gctttaatgc agtcacttga gctgcagtta | 1080 |
| atcactagtg cggccatcat cattgttggt cgtggagtct atggagctgg tcgtaatcct | 1140 |
| gttgtcgaag ccaagagata tagagaagct ggttggaagg catatcagca aagactttct | 1200 |
| cagcattaaa aaaagactaa tgtaaaattt ttttggttgg ttattgaaaa agtcgatgcc | 1260 |
| ttgtttgcgt ttgttttcct aggcgtttta tgtcagaagg catttagaat tagtatacaa | 1320 |
| gtactctttg gtaaaatttt atgtagcgac taaaatatta actattatag ataaacacct | 1380 |
| tgggaataaa aagtaatttg ctatagtaat ttattaaaca tgctcctaca acattaccac | 1440 |
| aatcttttct cttggattga cattgaataa gaaaagagtg aatttttta gacttgtaat | 1500 |
| gataactatg tacaaagcca atgaaagatg tatgtagatg aatgtaaaat a | 1551 |

<210> SEQ ID NO 4
<211> LENGTH: 1963
<212> TYPE: DNA
<213> ORGANISM: Artificial Sequence
<220> FEATURE:
<223> OTHER INFORMATION: Synthetic Construct; ura4SIREx2

<400> SEQUENCE: 4

| | | |
|---|---|---|
| atggatgcta gagtatttca aagctattca gctagagctg aggggatgaa aaatcccatt | 60 |
| gccaaggaat tgttggcttt gatggaagaa aagcaaagca acttgtcagt cgcggtcgat | 120 |
| ttgacgaaga aatccgaaat cttagaattg gtagataaaa ttggacccta tgtctgtgtt | 180 |
| atcaagacac atattgacgt tgtcgaggat ttcgaccagg atatggtaga aaaactggtg | 240 |
| gccttaggta aaaagcatcg ttttcttatc tttgaggatc gcaaattcgc agacattgga | 300 |
| aataccgtca agctacaata tgcatctggt gtgtacaaaa ttgcttcttg ggctcatatc | 360 |

-continued

```
acaaattgcc atacagtgcc aggcgagggt attatacaag gcctcaaaga agttggttta    420
cctttgggac gtggtctctt gcttttggct gaaatgtctt ccaaaggctc tttggctact    480
ggttcctaca cagagaaaac cttagaatgg tttgagaagc ataccgattt ttgctttggc    540
tttatagctg gtcgtcgatt tcctaacctt caaagcgact acataactat gtcccctggt    600
atcggcttgg atgttaaagg agacgggctg gacagcaat atcgtactcc tgaagaagtg     660
attgtaaact gcggtagcga tgggattaac tgcagactct gaagacaacg atgtgttttc    720
tcaagatgat aacggatcta gcttcgccat caataagtat gagacaaagg agtccatctt    780
tgatgaaaca tccatttgcc tgttgtacat ttttgcagga caaccagcct gagcacaaga    840
gacatggtgt actagacttt gtgcggaatg tctacttcaa aacttgcatc tttatatctg    900
atatatagag atatagagat atagagatat agagagaggc tgatgattta aaacacaaa     960 cgataagact tgtaacatga agtttgtcga aaaagtcaat ctttaaattc ctttctgaac   1020
ctctctgtta tgtcagtgct tcggtattat gctttaatgc agtcacttga gctgcagtta   1080
atcactagac cgcgggatta actgcagact ctgaagacaa cgatgtgttt tctcaagatg   1140
ataacggatc tagcttcgcc atcaataagt atgagacaaa ggagtccatc tttgatgaaa   1200
catccatttg cctgttgtac atttttgcag acaaccagc ctgagcacaa gagacatggt    1260
gtactagact ttgtgcggaa tgtctacttc aaaacttgca tctttatatc tgatatatag   1320
agatatagag atatagagat atagagagag ctgatgatt tataaacaca aacgataaga    1380
cttgtaacat gaagtttgtc gaaaaagtca atctttaaat tcctttctga acctctctgt   1440
tatgtcagtg cttcggtatt atgctttaat gcagtcactt gagctgcagt taatcactag   1500
tgcggccatc atcattgttg gtcgtggagt ctatggagct ggtcgtaatc ctgttgtcga   1560
agccaagaga tatagagaag ctggttggaa ggcatatcag caaagacttt ctcagcatta   1620
aaaaaagact aatgtaaaat ttttttggtt ggttattgaa aaagtcgatg ccttgtttgc   1680
gtttgttttc ctaggcgttt tatgtcagaa ggcatttaga attagtatac aagtactctt   1740
tggtaaaatt ttatgtagcg actaaaatat taactattat agataaacac cttgggaata   1800
aaaagtaatt tgctatagta atttattaaa catgctccta caacattacc acaatctttt   1860
ctcttggatt gacattgaat aagaaaagag tgaatttttt tagacttgta atgataacta   1920
tgtacaaagc caatgaaaga tgtatgtaga tgaatgtaaa ata                     1963
```

<210> SEQ ID NO 5
<211> LENGTH: 1551
<212> TYPE: DNA
<213> ORGANISM: Artificial Sequence
<220> FEATURE:
<223> OTHER INFORMATION: Synthetic Construct; ura4ERIS

<400> SEQUENCE: 5

```
atggatgcta gagtatttca aagctattca gctagagctg aggggatgaa aaatcccatt     60
gccaaggaat tgttggcttt gatggaagaa aagcaaagca acttgtcagt cgcggtcgat   120
ttgacgaaga aatccgaaat cttagaattg gtagataaaa ttggacccta tgtctgtgtt   180
atcaagacac atattgacgt tgtcgaggat ttcgaccagg atatggtaga aaaactggtg   240
gccttaggta aaaagcatcg ttttcttatc tttgaggatc gcaaattcgc agacattgga   300
aataccgtca agctacaata tgcatctggt gtgtacaaaa ttgcttcttg ggctcatatc   360
acaaattgcc atacagtgcc aggcgagggt attatacaag gcctcaaaga agttggttta   420
cctttgggac gtggtctctt gcttttggct gaaatgtctt ccaaaggctc tttggctact   480
```

-continued

```
ggttcctaca cagagaaaac cttagaatgg tttgagaagc ataccgattt ttgctttggc      540
tttatagctg gtcgtcgatt tcctaacctt caaagcgact acataactat gtcccctggt      600
atcggcttgg atgttaaagg agacgggctg ggacagcaat atcgtactcc tgaagaagtg      660
attgtaaact gcggtagcga tggccgcact agtgattaac tgcagctcaa gtgactgcat      720
taaagcataa taccgaagca ctgacataac agagaggttc agaaaggaat ttaaagattg      780 acttttcga caaacttcat gttacaagtc ttatcgtttg tgtttataaa tcatcagcct      840
ctctctatat ctctatatct ctatatctct atatatcaga tataaagatg caagttttga      900
agtagacatt ccgcacaaag tctagtacac catgtctctt gtgctcaggc tggttgtcct      960
gcaaaaatgt acaacaggca aatggatgtt tcatcaaaga tggactcctt tgtctcatac     1020
ttattgatgg cgaagctaga tccgttatca tcttgagaaa acacatcgtt gtcttcagag     1080
tctgcagtta atcccatcat cattgttggt cgtggagtct atggagctgg tcgtaatcct     1140
gttgtcgaag ccaagagata tagagaagct ggttggaagg catatcagca aagactttct     1200
cagcattaaa aaaagactaa tgtaaaattt ttttggttgg ttattgaaaa agtcgatgcc     1260
ttgtttgcgt ttgttttcct aggcgtttta tgtcagaagg catttagaat tagtatacaa     1320
gtactctttg gtaaaatttt atgtagcgac taaaatatta actattatag ataaacacct     1380
tgggaataaa aagtaatttg ctatagtaat ttattaaaca tgctcctaca acattaccac     1440
aatcttttct cttggattga cattgaataa gaaaagagtg aatttttttta gacttgtaat     1500 gataactatg tacaaagcca atgaaagatg tatgtagatg aatgtaaaat a              1551
```

<210> SEQ ID NO 6
<211> LENGTH: 1963
<212> TYPE: DNA
<213> ORGANISM: Artificial Sequence
<220> FEATURE:
<223> OTHER INFORMATION: Synthetic Construct; ura4ERISx2

<400> SEQUENCE: 6

```
atggatgcta gagtatttca aagctattca gctagagctg aggggatgaa aaatcccatt       60
gccaaggaat tgttggcttt gatggaagaa aagcaaagca acttgtcagt cgcggtcgat      120
ttgacgaaga aatccgaaat cttagaattg gtagataaaa ttggacccta tgtctgtgtt      180
atcaagacac atattgacgt tgtcgaggat ttcgaccagg atatggtaga aaaactggtg      240
gccttaggta aaaagcatcg ttttcttatc tttgaggatc gcaaattcgc agacattgga      300
aataccgtca agctacaata tgcatctggt gtgtacaaaa ttgcttcttg ggctcatatc      360
acaaattgcc atacagtgcc aggcgagggt attatacaag gcctcaaaga agttggttta      420
cctttgggac gtggtctctt gcttttggct gaaatgtctt ccaaaggctc tttggctact      480
ggttcctaca cagagaaaac cttagaatgg tttgagaagc ataccgattt ttgctttggc      540
tttatagctg gtcgtcgatt tcctaacctt caaagcgact acataactat gtcccctggt      600
atcggcttgg atgttaaagg agacgggctg ggacagcaat atcgtactcc tgaagaagtg      660
attgtaaact gcggtagcga tggccgcact agtgattaac tgcagctcaa gtgactgcat      720
taaagcataa taccgaagca ctgacataac agagaggttc agaaaggaat ttaaagattg      780 acttttcga caaacttcat gttacaagtc ttatcgtttg tgtttataaa tcatcagcct      840
ctctctatat ctctatatct ctatatctct atatatcaga tataaagatg caagttttga      900
agtagacatt ccgcacaaag tctagtacac catgtctctt gtgctcaggc tggttgtcct      960
gcaaaaatgt acaacaggca aatggatgtt tcatcaaaga tggactcctt tgtctcatac     1020
```

-continued

```
ttattgatgg cgaagctaga tccgttatca tcttgagaaa acacatcgtt gtcttcagag    1080
tctgcagtta atcccgcggt ctagtgatta actgcagctc aagtgactgc attaaagcat    1140
aataccgaag cactgacata acagagaggt tcagaaagga atttaaagat tgactttttc    1200
gacaaacttc atgttacaag tcttatcgtt tgtgtttata aatcatcagc ctctctctat    1260
atctctatat ctctatatct ctatatatca gatataaaga tgcaagtttt gaagtagaca    1320
ttccgcacaa agtctagtac accatgtctc ttgtgctcag gctggttgtc ctgcaaaaat    1380
gtacaacagg caaatggatg tttcatcaaa gatggactcc tttgtctcat acttattgat    1440
ggcgaagcta gatccgttat catcttgaga aaacacatcg ttgtcttcag agtctgcagt    1500
taatcccatc atcattgttg gtcgtggagt ctatggagct ggtcgtaatc ctgttgtcga    1560
agccaagaga tatagagaag ctggttggaa ggcatatcag caaagacttt ctcagcatta    1620
aaaaaagact aatgtaaaat ttttttggtt ggttattgaa aaagtcgatg ccttgtttgc    1680
gtttgttttc ctaggcgttt tatgtcagaa ggcatttaga attagtatac aagtactctt    1740
tggtaaaatt ttatgtagcg actaaaatat taactattat agataaacac cttgggaata    1800
aaaagtaatt tgctatagta atttattaaa catgctccta caacattacc acaatctttt    1860
ctcttggatt gacattgaat aagaaaagag tgaattttt tagacttgta atgataacta    1920
tgtacaaagc caatgaaaga tgtatgtaga tgaatgtaaa ata                       1963
```

<210> SEQ ID NO 7
<211> LENGTH: 2375
<212> TYPE: DNA
<213> ORGANISM: Artificial Sequence
<220> FEATURE:
<223> OTHER INFORMATION: Synthetic Construct; ura4ERISx3

<400> SEQUENCE: 7

```
atggatgcta gagtatttca aagctattca gctagagctg aggggatgaa aaatcccatt      60
gccaaggaat tgttggcttt gatggaagaa agcaaagca acttgtcagt cgcggtcgat     120
ttgacgaaga aatccgaaat cttagaattg gtagataaaa ttggacccta tgtctgtgtt    180
atcaagacac atattgacgt tgtcgaggat ttcgaccagg atatggtaga aaaactggtg    240
gccttaggta aaaagcatcg ttttcttatc tttgaggatc gcaaattcgc agacattgga    300
aataccgtca gctacaata tgcatctggt gtgtacaaaa ttgcttcttg ggctcatatc    360
acaaattgcc atacagtgcc aggcgagggt attatacaag gcctcaaaga agttggttta    420
cctttgggac gtggtctctt gcttttggct gaaatgtctt ccaaaggctc tttggctact    480
ggttcctaca cagagaaaac cttagaatgg tttgagaagc ataccgattt ttgctttggc    540
tttatagctg gtcgtcgatt tcctaacctt caaagcgact acataactat gtcccctggt    600
atcggcttgg atgttaaagg agacgggctg ggacagcaat atcgtactcc tgaagaagtg    660
attgtaaact gcggtagcga tggccgcact agtgattaac tgcagctcaa gtgactgcat    720
taaagcataa taccgaagca ctgacataac agagaggttc agaaaggaat ttaaagattg    780 acttttcga caaacttcat gttacaagtc ttatcgtttg tgtttataaa tcatcagcct    840
ctctctatat ctctatatct ctatatcaga tataaagatg caagttttga                900
agtagacatt ccgcacaaag tctagtacac catgtctctt gtgctcaggc tggttgtcct    960
gcaaaaatgt acaacaggca aatggatgtt tcatcaagaa tggactcctt tgtctcatac   1020
ttattgatgg cgaagctaga tccgttatca tcttgagaaa acacatcgtt gtcttcagag    1080
tctgcagtta atcccgcggt ctagtgatta actgcagctc aagtgactgc attaaagcat    1140
```

```
aataccgaag cactgacata acagagaggt tcagaaagga atttaaagat tgactttttc    1200
gacaaacttc atgttacaag tcttatcgtt tgtgtttata aatcatcagc ctctctctat    1260
atctctatat ctctatatct ctatatatca gatataaaga tgcaagtttt gaagtagaca    1320
ttccgcacaa agtctagtac accatgtctc ttgtgctcag gctggttgtc ctgcaaaaat    1380
gtacaacagg caaatggatg tttcatcaaa gatggactcc tttgtctcat acttattgat    1440
ggcgaagcta gatccgttat catcttgaga aaacacatcg ttgtcttcag agtctgcagt    1500
taatcccgcg gtctagtgat taactgcagc tcaagtgact gcattaaagc ataataccga    1560
agcactgaca taacagagag gttcagaaag gaatttaaag attgactttt tcgacaaact    1620
tcatgttaca agtcttatcg tttgtgttta taaatcatca gcctctctct atatctctat    1680
atctctatat ctctatatat cagatataaa gatgcaagtt ttgaagtaga cattccgcac    1740
aaagtctagt acaccatgtc tcttgtgctc aggctggttg tcctgcaaaa atgtacaaca    1800
ggcaaatgga tgtttcatca agatggact ccttttgtctc atacttattg atggcgaagc    1860
tagatccgtt atcatcttga gaaaacacat cgttgtcttc agagtctgca gttaatccca    1920
tcatcattgt tggtcgtgga gtctatggag ctggtcgtaa tcctgttgtc gaagccaaga    1980
gatatagaga agctggttgg aaggcatatc agcaaagact ttctcagcat taaaaaaga    2040 ctaatgtaaa atttttttgg ttggttattg aaaaagtcga tgccttgttt gcgtttgttt    2100
tcctaggcgt tttatgtcag aaggcattta gaattagtat acaagtactc tttggtaaaa    2160 tttatgtag cgactaaaat attaactatt atagataaac accttgggaa taaaaagtaa    2220
tttgctatag taatttatta aacatgctcc tacaacatta ccacaatctt ttctcttgga    2280
ttgacattga ataagaaaag agtgaatttt tttagacttg taatgataac tatgtacaaa    2340
gccaatgaaa gatgtatgta gatgaatgta aaata                              2375
```

<210> SEQ ID NO 8
<211> LENGTH: 1075
<212> TYPE: DNA
<213> ORGANISM: Artificial Sequence
<220> FEATURE:
<223> OTHER INFORMATION: Synthetic Construct; c10orf96-u4

<400> SEQUENCE: 8

```
atgagcttgg agtccctgtt tcagcacatc atcttcaccg agcatcaggc ggaggagagt      60
cgccgtttga tgcgagaagt aaggtcggaa ataaccagat gtcgtgaaaa aattaagaaa     120
gcaacggagg agctgaatga agagaaaatc aagctggaat ctaaggttca acagtttttt     180
gaaaaatcct tcttcttaca gcttttgaaa gctcatgaaa atgctttaga aaaacagtac     240
agtgaaatta caaccatag aatatgctt cttcaaacct tgaggctat aaagaaacaa        300 atgatagagg aggaagacaa atttattaag gaaattacag actttaataa tgattatgaa     360
ataacaaaga aaagagagct tttgatgaaa gaaaatgtca agattgaaat atctgactta     420
gaaaaccaag caaacatgtt gaaagtgaa atgaagtcaa tggaacatga tagtagccag      480
ttaaatgaac ttcaaaaaca aaagagtgaa ttgatacaag aattatttac tctccaaaga     540
aaacttaaag ttttttgaaga tgaagagaat gaatccattt gtactaccaa atatctagtg    600
attaactgca gttaatccca tcatcattgt tggtcgtgga gtctatggag ctggtcgtaa     660
tcctgttgtc gaagccaaga gatatagaga agctggttgg aaggcatatc agcaaagact    720
ttctcagcat taaaaaaga ctaatgtaaa atttttttgg ttggttattg aaaaagtcga      780
tgccttgttt gcgtttgttt tcctaggcgt tttatgtcag aaggcattta gaattagtat     840
```

```
acaagtactc tttggtaaaa tttatgtag cgactaaaat attaactatt atagataaac      900
accttgggaa taaaaagtaa tttgctatag taatttatta aacatgctcc tacaacatta      960
ccacaatctt ttctcttgga ttgacattga ataagaaaag agtgaatttt tttagacttg     1020
taatgataac tatgtacaaa gccaatgaaa gatgtatgta gatgaatgta aaata          1075
```

<210> SEQ ID NO 9
<211> LENGTH: 1487
<212> TYPE: DNA
<213> ORGANISM: Artificial Sequence
<220> FEATURE:
<223> OTHER INFORMATION: Synthetic Construct; c10orf96-SIRE-u4

<400> SEQUENCE: 9

```
atgagcttgg agtccctgtt tcagcacatc atcttcaccg agcatcaggc ggaggagagt       60
cgccgtttga tgcgagaagt aaggtcggaa ataaccagat gtcgtgaaaa aattaagaaa      120
gcaacggagg agctgaatga agagaaaatc aagctggaat ctaaggttca acagttttt       180 gaaaaatcct tcttcttaca gcttttgaaa gctcatgaaa atgctttaga aaaacagtac      240
agtgaaatta caaaccatag gaatatgctt cttcaaacct tgaggctat aaagaaacaa      300 atgatagagg aggaagacaa atttattaag gaaattacag actttaataa tgattatgaa      360
ataacaaaga aaagagagct tttgatgaaa gaaaatgtca agattgaaat atctgactta      420
gaaaaccaag caaacatgtt gaaaagtgaa atgaagtcaa tggaacatga tagtagccag      480
ttaaatgaac ttcaaaaaca aaagagtgaa ttgatacaag aattatttac tctccaaaga      540
aaacttaaag tttttgaaga tgaagagaat gaatccattt gtactaccaa atatctagac      600
cgcgggatta actgcagact ctgaagacaa cgatgtgttt tctcaagatg ataacggatc      660
tagcttcgcc atcaataagt atgagacaaa ggagtccatc tttgatgaaa catccatttg      720
cctgttgtac atttttgcag gacaaccagc ctgagcacaa gagacatggt gtactagact      780
ttgtgcggaa tgtctacttc aaaacttgca tctttatatc tgatatatag agatatagag      840
atatagagat atagagagag gctgatgatt tataaacaca aacgataaga cttgtaacat      900
gaagtttgtc gaaaaagtca atctttaaat tcctttctga acctctctgt tatgtcagtg      960
cttcggtatt atgctttaat gcagtcactt gagctgcagt taatcactag tgattaactg     1020
cagttaatcc catcatcatt gttggtcgtg gagtctatgg agctggtcgt aatcctgttg     1080
tcgaagccaa gagatataga gaagctggtt ggaaggcata tcagcaaaga ctttctcagc     1140
attaaaaaaa gactaatgta aaatttttt ggttggttat tgaaaaagtc gatgccttgt      1200
ttgcgtttgt tttcctaggc gttttatgtc agaaggcatt tagaattagt atacaagtac     1260
tctttggtaa aatttatgt agcgactaaa atattaacta ttatagataa acaccttggg     1320
aataaaaagt aatttgctat agtaatttat taaacatgct cctacaacat taccacaatc     1380
ttttctcttg gattgacatt gaataagaaa agagtgaatt ttttttagact tgtaatgata     1440 actatgtaca aagccaatga agatgtatg tagatgaatg taaaata                    1487
```

<210> SEQ ID NO 10
<211> LENGTH: 1457
<212> TYPE: DNA
<213> ORGANISM: Artificial Sequence
<220> FEATURE:
<223> OTHER INFORMATION: Synthetic Construct; c10orf96-ERIS-u4

```
<400> SEQUENCE: 10
atgagcttgg agtccctgtt tcagcacatc atcttcaccg agcatcaggc ggaggagagt      60
cgccgtttga tgcgagaagt aaggtcggaa ataaccagat gtcgtgaaaa aattaagaaa     120
gcaacggagg agctgaatga agagaaaatc aagctggaat ctaaggttca acagtttttt     180
gaaaaatcct tcttcttaca gcttttgaaa gctcatgaaa atgctttaga aaaacagtac     240
agtgaaatta caaccatag gaatatgctt cttcaaacct tgaggctat aaagaaacaa      300 atgatagagg aggaagacaa atttattaag gaaattacag actttaataa tgattatgaa     360
ataacaaaga aaagagagct tttgatgaaa gaaaatgtca agattgaaat atctgactta     420
gaaaaccaag caaacatgtt gaaaagtgaa atgaagtcaa tggaacatga tagtagccag     480
ttaaatgaac ttcaaaaaca aaagagtgaa ttgatacaag aattatttac tctccaaaga     540
aaacttaaag tttttgaaga tgaagagaat gaatccattt gtactaccaa atatctagtg     600
attaactgca gctcaagtga ctgcattaaa gcataatacc gaagcactga cataacagag     660
aggttcagaa aggaatttaa agattgactt tttcgacaaa cttcatgtta caagtcttat     720
cgtttgtgtt tataaatcat cagcctctct ctatatctct atatctctat atctctatat     780
atcagatata aagatgcaag ttttgaagta gacattccgc acaaagtcta gtacaccatg     840
tctcttgtgc tcaggctggt tgtcctgcaa aaatgtacaa caggcaaatg gatgtttcat     900
caaagatgga ctcctttgtc tcatacttat tgatggcgaa gctagatccg ttatcatctt     960
gagaaaacac atcgttgtct tcagagtctg cagttaatcc catcatcatt gttggtcgtg    1020
gagtctatgg agctggtcgt aatcctgttg tcgaagccaa gagatataga gaagctggtt    1080
ggaaggcata tcagcaaaga cttttctcagc attaaaaaaa gactaatgta aaattttttt    1140
ggttggttat tgaaaaagtc gatgccttgt ttgcgtttgt tttcctaggc gttttatgtc    1200
agaaggcatt tagaattagt atacaagtac tcttttggtaa aatttatgt agcgactaaa    1260 atattaacta ttatagataa acaccttggg aataaaaagt aatttgctat agtaatttat    1320
taaacatgct cctacaacat taccacaatc ttttctcttg gattgacatt gaataagaaa    1380
agagtgaatt tttttagact tgtaatgata actatgtaca aagccaatga aagatgtatg    1440
tagatgaatg taaaata                                                    1457

<210> SEQ ID NO 11
<211> LENGTH: 1899
<212> TYPE: DNA
<213> ORGANISM: Artificial Sequence
<220> FEATURE:
<223> OTHER INFORMATION: Synthetic Construct; c10orf96-SIREx2-u4

<400> SEQUENCE: 11
atgagcttgg agtccctgtt tcagcacatc atcttcaccg agcatcaggc ggaggagagt      60
cgccgtttga tgcgagaagt aaggtcggaa ataaccagat gtcgtgaaaa aattaagaaa     120
gcaacggagg agctgaatga agagaaaatc aagctggaat ctaaggttca acagtttttt     180
gaaaaatcct tcttcttaca gcttttgaaa gctcatgaaa atgctttaga aaaacagtac     240
agtgaaatta caaccatag gaatatgctt cttcaaacct tgaggctat aaagaaacaa      300 atgatagagg aggaagacaa atttattaag gaaattacag actttaataa tgattatgaa     360
ataacaaaga aaagagagct tttgatgaaa gaaaatgtca agattgaaat atctgactta     420
gaaaaccaag caaacatgtt gaaaagtgaa atgaagtcaa tggaacatga tagtagccag     480
ttaaatgaac ttcaaaaaca aaagagtgaa ttgatacaag aattatttac tctccaaaga     540
```

-continued

```
aaacttaaag tttttgaaga tgaagagaat gaatccattt gtactaccaa atatctagac      600
cgcgggatta actgcagact ctgaagacaa cgatgtgttt tctcaagatg ataacggatc      660
tagcttcgcc atcaataagt atgagacaaa ggagtccatc tttgatgaaa catccatttg      720
cctgttgtac atttttgcag acaaccagc ctgagcaca gagacatggt gtactagact       780
ttgtgcggaa tgtctacttc aaaacttgca tctttatatc tgatatatag agatatagag      840
atatagagat atagagagag gctgatgatt tataaacaca aacgataaga cttgtaacat      900
gaagtttgtc gaaaaagtca atctttaaat tcctttctga acctctctgt tatgtcagtg      960
cttcggtatt atgctttaat gcagtcactt gagctgcagt taatcactag accgcgggat     1020
taactgcaga ctctgaagac aacgatgtgt tttctcaaga tgataacgga tctagcttcg     1080
ccatcaataa gtatgagaca aaggagtcca tctttgatga acatccatt tgcctgttgt     1140 acatttttgc aggacaacca gcctgagcac aagagacatg gtgtactaga ctttgtgcgg     1200
aatgtctact tcaaaacttg catctttata tctgatatat agagatatag agatatagag     1260
atatagagag aggctgatga tttataaaca caaacgataa gacttgtaac atgaagtttg     1320
tcgaaaaagt caatctttaa attcctttct gaacctctct gttatgtcag tgcttcggta     1380
ttatgcttta atgcagtcac ttgagctgca gttaatcact agtgattaac tgcagttaat     1440
cccatcatca ttgttggtcg tggagtctat ggagctggtc gtaatcctgt tgtcgaagcc     1500
aagagatata gagaagctgg ttggaaggca tatcagcaaa gactttctca gcattaaaaa     1560
aagactaatg taaaatttt ttggttggtt attgaaaaag tcgatgcctt gtttgcgttt     1620
gttttcctag gcgttttatg tcagaaggca tttagaatta gtatacaagt actctttggt     1680
aaaattttat gtagcgacta aaatattaac tattatagat aaacaccttg ggaataaaaa     1740
gtaatttgct atagtaattt attaaacatg ctcctacaac attaccacaa tcttttctct     1800
tggattgaca ttgaataaga aaagagtgaa ttttttttaga cttgtaatga taactatgta     1860
caaagccaat gaaagatgta tgtagatgaa tgtaaaata                             1899
```

<210> SEQ ID NO 12  
<211> LENGTH: 1869  
<212> TYPE: DNA  
<213> ORGANISM: Artificial Sequence  
<220> FEATURE:  
<223> OTHER INFORMATION: Synthetic Construct; c10orf96-ERISx2-u4

<400> SEQUENCE: 12

```
atgagcttgg agtccctgtt tcagcacatc atcttcaccg agcatcaggc ggaggagagt       60
cgccgtttga tgcgagaagt aaggtcggaa ataaccagat gtcgtgaaaa aattaagaaa      120
gcaacggagg agctgaatga agagaaaatc aagctggaat ctaaggttca acagtttttt      180
gaaaaatcct tcttcttaca gcttttgaaa gctcatgaaa atgctttaga aaaacagtac      240
agtgaaatta caaccatag gaatatgctt ctcaaacct tgaggctat aaagaaacaa        300 atgatagagg aggaagacaa atttattaag gaaattacag actttaataa tgattatgaa      360
ataacaaaga aaagagagct tttgatgaaa gaaaatgtca agattgaaat atctgactta      420
gaaaaccaag caaacatgtt gaaaagtgaa atgaagtcaa tggaacatga tagtagccag      480
ttaaatgaac ttcaaaaaca aaagagtgaa ttgatacaag aattatttac tctccaaaga      540
aaacttaaag tttttgaaga tgaagagaat gaatccattt gtactaccaa atatctagtg      600
attaactgca gctcaagtga ctgcattaaa gcataatacc gaagcactga cataacagag      660
aggttcagaa aggaatttaa agattgactt tttcgacaaa cttcatgtta caagtcttat      720
```

-continued

| | |
|---|---|
| cgtttgtgtt tataaatcat cagcctctct ctatatctct atatctctat atctctatat | 780 |
| atcagatata aagatgcaag ttttgaagta gacattccgc acaaagtcta gtacaccatg | 840 |
| tctcttgtgc tcaggctggt tgtcctgcaa aaatgtacaa caggcaaatg gatgtttcat | 900 |
| caaagatgga ctcctttgtc tcatacttat tgatggcgaa gctagatccg ttatcatctt | 960 |
| gagaaaacac atcgttgtct tcagagtctg cagttaatcc cgcggtctag tgattaactg | 1020 |
| cagctcaagt gactgcatta agcataata ccgaagcact gacataacag agaggttcag | 1080 |
| aaaggaattt aaagattgac ttttcgaca aacttcatgt acaagtctt atcgtttgtg | 1140 |
| tttataaatc atcagcctct ctctatatct ctatatctct atatcagata | 1200 |
| taaagatgca agttttgaag tagacattcc gcacaaagtc tagtacacca tgtctcttgt | 1260 |
| gctcaggctg ttgtcctgc aaaaatgtac aacaggcaaa tggatgtttc atcaaagatg | 1320 |
| gactcctttg tctcatactt attgatggcg aagctagatc cgttatcatc ttgagaaaac | 1380 |
| acatcgttgt cttcagagtc tgcagttaat cccatcatca ttgttggtcg tggagtctat | 1440 |
| ggagctggtc gtaatcctgt tgtcgaagcc aagagatata gagaagctgg ttggaaggca | 1500 |
| tatcagcaaa gactttctca gcattaaaaa aagactaatg taaaatttt ttggttggtt | 1560 |
| attgaaaaag tcgatgcctt gtttgcgttt gttttcctag gcgttttatg tcagaaggca | 1620 |
| tttagaatta gtatacaagt actctttggt aaaattttat gtagcgacta aaatattaac | 1680 |
| tattatagat aaacaccttg ggaataaaaa gtaatttgct atagtaattt attaaacatg | 1740 |
| ctcctacaac attaccacaa tcttttctct tggattgaca ttgaataaga aaagagtgaa | 1800 |
| tttttttaga cttgtaatga taactatgta caaagccaat gaaagatgta tgtagatgaa | 1860 |
| tgtaaaata | 1869 |

<210> SEQ ID NO 13
<211> LENGTH: 2311
<212> TYPE: DNA
<213> ORGANISM: Artificial Sequence
<220> FEATURE:
<223> OTHER INFORMATION: Synthetic Construct; c10orf96-SIREx3-u4

<400> SEQUENCE: 13

| | |
|---|---|
| atgagcttgg agtccctgtt tcagcacatc atcttcaccg agcatcaggc ggaggagagt | 60 |
| cgccgtttga tgcgagaagt aaggtcggaa ataaccagat gtcgtgaaaa aattaagaaa | 120 |
| gcaacggagg agctgaatga agagaaaatc aagctggaat ctaaggttca acagtttttt | 180 |
| gaaaaatcct tcttcttaca gcttttgaaa gctcatgaaa atgctttaga aaacagtac | 240 |
| agtgaaatta caaaccatag gaatatgctt cttcaaacct ttgaggctat aagaaacaa | 300 |
| atgatagagg aggaagacaa atttattaag gaaattacag actttaataa tgattatgaa | 360 |
| ataacaaaga aaagagagct tttgatgaaa gaaaatgtca agattgaaat atctgactta | 420 |
| gaaaaccaag caaacatgtt gaaaagtgaa atgaagtcaa tggaacatga tagtagccag | 480 |
| ttaaatgaac ttcaaaaaca aaagagtgaa ttgatacaag aattatttac tctccaaaga | 540 |
| aaacttaaag ttttttgaaga tgaagagaat gaatccattt gtactaccaa atatctagac | 600 |
| cgcgggatta actgcagact ctgaagacaa cgatgtgttt tctcaagatg ataacggatc | 660 |
| tagcttcgcc atcaataagt atgagacaaa ggagtccatc tttgatgaaa catccatttg | 720 |
| cctgttgtac attttgcag acaaccagc ctgagcacaa gagacatggt gtactagact | 780 |
| ttgtgcggaa tgtctacttc aaaacttgca tctttatatc tgatatatag agatatagag | 840 |
| atatagagat atagagagag gctgatgatt tataaacaca aacgataaga cttgtaacat | 900 |

-continued

| | |
|---|---|
| gaagtttgtc gaaaaagtca atctttaaat tcctttctga acctctctgt tatgtcagtg | 960 |
| cttcggtatt atgctttaat gcagtcactt gagctgcagt taatcactag accgcgggat | 1020 |
| taactgcaga ctctgaagac aacgatgtgt tttctcaaga tgataacgga tctagcttcg | 1080 |
| ccatcaataa gtatgagaca aaggagtcca tctttgatga acatccatt tgcctgttgt | 1140 |
| acatttttgc aggacaacca gcctgagcac aagagacatg gtgtactaga ctttgtgcgg | 1200 |
| aatgtctact tcaaaacttg catctttata tctgatatat agagatatag agatatagag | 1260 |
| atatagagag aggctgatga tttataaaca caaacgataa gacttgtaac atgaagtttg | 1320 |
| tcgaaaaagt caatctttaa attcctttct gaacctctct gttatgtcag tgcttcggta | 1380 |
| ttatgctttta atgcagtcac ttgagctgca gttaatcact agaccgcggg attaactgca | 1440 |
| gactctgaag acaacgatgt gttttctcaa gatgataacg gatctagctt cgccatcaat | 1500 |
| aagtatgaga caaaggagtc catctttgat gaaacatcca tttgcctgtt gtacattttt | 1560 |
| gcaggacaac cagcctgagc acaagagaca tggtgtacta gactttgtgc ggaatgtcta | 1620 |
| cttcaaaact tgcatcttta tatctgatat atagagatat agagatatag agatatagag | 1680 |
| agaggctgat gatttataaa cacaaacgat aagacttgta acatgaagtt tgtcgaaaaa | 1740 |
| gtcaatcttt aaattccttt ctgaacctct ctgttatgtc agtgcttcgg tattatgctt | 1800 |
| taatgcagtc acttgagctg cagttaatca ctagtgatta actgcagtta atcccatcat | 1860 |
| cattgttggt cgtggagtct atggagctgg tcgtaatcct gttgtcgaag ccaagagata | 1920 |
| tagaaagct ggttggaagg catatcagca aagactttct cagcattaaa aaagactaa | 1980 |
| tgtaaaattt ttttggttgg ttattgaaaa agtcgatgcc ttgtttgcgt ttgttttcct | 2040 |
| aggcgtttta tgtcagaagg catttagaat tagtatacaa gtactctttg gtaaaattt | 2100 |
| atgtagcgac taaaatatta actattatag ataaacacct tgggaataaa aagtaatttg | 2160 |
| ctatagtaat ttattaaaca tgctcctaca acattaccac aatctttctc cttggattga | 2220 |
| cattgaataa gaaaagagtg aattttttta gacttgtaat gataactatg tacaaagcca | 2280 |
| atgaaagatg tatgtagatg aatgtaaaat a | 2311 |

<210> SEQ ID NO 14
<211> LENGTH: 2281
<212> TYPE: DNA
<213> ORGANISM: Artificial Sequence
<220> FEATURE:
<223> OTHER INFORMATION: Synthetic Construct; c10orf96-ERISx3-u4

<400> SEQUENCE: 14

| | |
|---|---|
| atgagcttgg agtccctgtt tcagcacatc atcttcaccg agcatcaggc ggaggagagt | 60 |
| cgccgtttga tgcgagaagt aaggtcggaa ataaccagat gtcgtgaaaa aattaagaaa | 120 |
| gcaacggagg agctgaatga agagaaaatc aagctggaat ctaaggttca acagtttttt | 180 |
| gaaaaatcct tcttcttaca gcttttgaaa gctcatgaaa atgctttaga aaaacagtac | 240 |
| agtgaaatta caaaccatag gaatatgctt cttcaaacct tgaggctat aaagaaacaa | 300 |
| atgatagagg aggaagacaa atttattaag gaaattcag actttaataa tgattatgaa | 360 |
| ataacaaaga aaagagagct tttgatgaaa gaaaatgtca agattgaaat atctgactta | 420 |
| gaaaaccaag caaacatgtt gaaaagtgaa atgaagtcaa tggaacatga tagtagccag | 480 |
| ttaaatgaac ttcaaaaaca aaagagtgaa ttgatacaag aattatttac tctccaaaga | 540 |
| aaacttaaag tttttgaaga tgaagagaat gaatccattt gtactaccaa atatctagtg | 600 |
| attaactgca gctcaagtga ctgcattaaa gcataatacc gaagcactga cataacagag | 660 |

```
aggttcagaa aggaatttaa agattgactt tttcgacaaa cttcatgtta caagtcttat    720
cgtttgtgtt tataaatcat cagcctctct ctatatctct atatctctat atctctatat    780
atcagatata aagatgcaag ttttgaagta gacattccgc acaaagtcta gtacaccatg    840
tctcttgtgc tcaggctggt tgtcctgcaa aaatgtacaa caggcaaatg gatgtttcat    900
caaagatgga ctcctttgtc tcatacttat tgatggcgaa gctagatccg ttatcatctt    960
gagaaaacac atcgttgtct tcagagtctg cagttaatcc cgcggtctag tgattaactg   1020
cagctcaagt gactgcatta aagcataata ccgaagcact gacataacag agaggttcag   1080
aaaggaattt aaagattgac ttttcgaca aacttcatgt tacaagtctt atcgtttgtg   1140
tttataaatc atcagcctct ctctatatct ctatatctct atatctctat atatcagata   1200
taaagatgca agttttgaag tagacattcc gcacaaagtc tagtacacca tgtctcttgt   1260
gctcaggctg gttgtcctgc aaaaatgtac aacaggcaaa tggatgtttc atcaaagatg   1320
gactcctttg tctcatactt attgatggcg aagctagatc cgttatcatc ttgagaaaac   1380
acatcgttgt cttcagagtc tgcagttaat cccgcggtct agtgattaac tgcagctcaa   1440
gtgactgcat taaagcataa taccgaagca ctgacataac agagaggttc agaaaggaat   1500
ttaaagattg acttttcga caacttcat gttacaagtc ttatcgtttg tgtttataaa   1560
tcatcagcct ctctatatct ctatatctct atatctctat atatcagata taaagatg   1620 caagttttga agtagacatt ccgcacaaag tctagtacac catgtctctt gtgctcaggc   1680
tggttgtcct gcaaaaatgt acaacaggca aatggatgtt tcatcaaaga tggactcctt   1740
tgtctcatac ttattgatgg cgaagctaga tccgttatca tcttgagaaa acacatcgtt   1800
gtcttcagag tctgcagtta atcccatcat cattgttggt cgtggagtct atggagctgg   1860
tcgtaatcct gttgtcgaag ccaagagata tagagaagct ggttggaagg catatcagca   1920
aagactttct cagcattaaa aaaagactaa tgtaaaattt ttttggttgg ttattgaaaa   1980
agtcgatgcc ttgtttgcgt tgttttcct aggcgtttta tgtcagaagg catttagaat   2040
tagtatacaa gtactctttg gtaaaatttt atgtagcgac taaaatatta actattatag   2100
ataaacacct tgggaataaa aagtaatttg ctatagtaat ttattaaaca tgctcctaca   2160
acattaccac aatcttttct cttggattga cattgaataa gaaagagtg aattttttta   2220 gacttgtaat gataactatg tacaaagcca atgaaagatg tatgtagatg aatgtaaaat   2280
a                                                                   2281
```

<210> SEQ ID NO 15
<211> LENGTH: 1233
<212> TYPE: DNA
<213> ORGANISM: Artificial Sequence
<220> FEATURE:
<223> OTHER INFORMATION: Synthetic Construct; RD-his5-u4

<400> SEQUENCE: 15

```
tatgaattta gacaatttgg atgcaaaatt gtcgttcttt tcctgacata atccaattca     60
tctttacaac actcccttcg tgcttgggac ttcagaactt ccagtaagac tagtagccgc    120
gcgcatggca acagccagag atttaaaagc gctttcagca cgatgatggt cattactacc    180
atataagcag gtaacatgca aagtaattcc agctgctacc gaaaggaat atagtaagtg    240 agggatcatt tcacaggaca attccccaac cttttcacgc tttaatccca aatcgataac    300
agcatagggc cgtcccgaca agtcaactac gcttctagaa agagcttcgt caagtggaca    360
ataagcatgt ccaaatcttt taacgccggc aaagttaccc atagcctgct tgaatgcaat    420
```

-continued

```
accaagtgca atagcagtat cttctgcagt gtgatgatca tcgatgatta aatcacctct    480
tgagtaaagt cgtaagctcc agcctgcatg tttagccagt gcatgataca tgtgatccaa    540
gaatccaatt cccgtgtcta cttggattac ttgttctccc ttttggtttg catgcttgga    600
agttataagt tcatcaataa aattcgactc ttcaggtaag ggagctttgt ccaaagcgat    660
ggcaacgctg attttcgttt cgttcgtatt tctttctaca aaagccctcc tcatcgtgat    720
gcaaaactac tcttttcaat tagatcaacc gagaattaca ggaagctagt gcggccatca    780
tcattgttgg tcgtggagtc tatggagctg gtcgtaatcc tgttgtcgaa gccaagagat    840
atagagaagc tggttggaag gcatatcagc aaagactttc tcagcattaa aaaagacta     900 atgtaaaatt tttttggttg gttattgaaa aagtcgatgc cttgtttgcg tttgttttcc    960
taggcgtttt atgtcagaag gcatttagaa ttagtataca agtactcttt ggtaaaattt   1020
tatgtagcga ctaaaatatt aactattata gataaacacc ttgggaataa aaagtaattt   1080
gctatagtaa tttattaaac atgctcctac aacattacca caatcttttc tcttggattg   1140
acattgaata agaaaagagt gattttttt agacttgtaa tgataactat gtacaaagcc    1200
aatgaaagat gtatgtagat gaatgtaaaa tac                               1233
```

<210> SEQ ID NO 16
<211> LENGTH: 2451
<212> TYPE: DNA
<213> ORGANISM: Artificial Sequence
<220> FEATURE:
<223> OTHER INFORMATION: Synthetic Construct; RD-his5-ERISx3-u4

<400> SEQUENCE: 16

```
tatgaattta gacaatttgg atgcaaaatt gtcgttcttt tcctgacata atccaattca     60
tctttacaac actcccttcg tgcttgggac ttcagaactt ccagtaagac tagtagccgc    120
gcgcatggca acagccagag atttaaaagc gctttcagca cgatgatggt cattactacc    180
atataagcag gtaacatgca agtaattcc agctgctacc gaaaaggaat atagtaagtg    240
agggatcatt tcacaggaca attccccaac cttttcacgc tttaatccca aatcgataac    300
agcatagggc cgtcccgaca agtcaactac gcttctagaa agagcttcgt caagtggaca    360
ataagcatgt ccaaatcttt taacgccggc aaagttaccc atagcctgct tgaatgcaat    420
accaagtgca atagcagtat cttctgcagt gtgatgatca tcgatgatta aatcacctct    480
tgagtaaagt cgtaagctcc agcctgcatg tttagccagt gcatgataca tgtgatccaa    540
gaatccaatt cccgtgtcta cttggattac ttgttctccc ttttggtttg catgcttgga    600
agttataagt tcatcaataa aattcgactc ttcaggtaag ggagctttgt ccaaagcgat    660
ggcaacgctg attttcgttt cgttcgtatt tctttctaca aaagccctcc tcatcgtgat    720
gcaaaactac tcttttcaat tagatcaacc gagaattaca ggaagctagt gattaactgc    780
agctcaagtg actgcattaa agcataatac cgaagcactg acataacaga gaggttcaga    840
aaggaattta agattgact ttttcgacaa acttcatgtt acaagtctta tcgtttgtgt     900
ttataaatca tcagcctctc tctatatctc tatatctcta tatcagatat                960
aaagatgcaa gttttgaagt agacattccg cacaaagtct agtacaccat gtctcttgtg   1020
ctcaggctgg ttgtcctgca aaaatgtaca acaggcaaat ggatgtttca tcaaagatgg   1080
actcctttgt ctcatactta ttgatggcga agctagatcc gttatcatct tgagaaaaca   1140
catcgttgtc ttcagagtct gcagttaatc ccgcggtcta gtgattaact gcagctcaag   1200
tgactgcatt aaagcataat accgaagcac tgacataaca gagaggttca gaaaggaatt   1260
```

-continued

```
taaagattga cttttttcgac aaacttcatg ttacaagtct tatcgtttgt gtttataaat      1320
catcagcctc tctctatatc tctatatctc tatatctcta tatatcagat ataaagatgc      1380 aagtttgaa  gtagacattc cgcacaaagt ctagtacacc atgtctcttg tgctcaggct      1440
ggttgtcctg caaaaatgta aacaggcaa  atggatgttt catcaaagat ggactccttt      1500
gtctcatact tattgatggc gaagctagat ccgttatcat cttgagaaaa cacatcgttg      1560
tcttcagagt ctgcagttaa tcccgcggtc tagtgattaa ctgcagctca agtgactgca      1620
ttaaagcata ataccgaagc actgacataa cagagaggtt cagaaaggaa tttaaagatt      1680
gactttttcg acaaacttca tgttacaagt cttatcgttt gtgtttataa atcatcagcc      1740
tctctctata tctctatatc tctatatctc tatatcag   ataaagat gcaagttttg      1800 aagtagacat tccgcacaaa gtctagtaca ccatgtctct tgtgctcagg ctggttgtcc      1860
tgcaaaaatg tacaacaggc aaatggatgt tcatcaaag atggactcct tgtctcata      1920 cttattgatg gcgaagctag atccgttatc atcttgagaa acacatcgt tgtcttcaga      1980 gtctgcagtt aatcccatca tcattgttgg tcgtggagtc tatggagctg tcgtaatcc      2040 tgttgtcgaa gccaagagat atagagaagc tggttggaag gcatatcagc aaagactttc      2100
tcagcattaa aaaagacta atgtaaaatt ttttttggttg gttattgaaa aagtcgatgc      2160
cttgtttgcg tttgttttcc taggcgtttt atgtcagaag gcatttagaa ttagtataca      2220
agtactcttt ggtaaaattt tatgtagcga ctaaaatatt aactattata gataaacacc      2280
ttgggaataa aaagtaattt gctatagtaa tttattaaac atgctcctac aacattacca      2340 caatctttc  tcttggattg acattgaata agaaaagagt gaattttttt agacttgtaa      2400
tgataactat gtacaaagcc aatgaaagat gtatgtagat gaatgtaaaa t              2451
```

<210> SEQ ID NO 17
<211> LENGTH: 2421
<212> TYPE: DNA
<213> ORGANISM: Artificial Sequence
<220> FEATURE:
<223> OTHER INFORMATION: Synthetic Construct; promoter-RD-his5-u4

<400> SEQUENCE: 17

```
cgactctaga ggatcagaaa attatcgcca taaaagacag aataagtcat cagcggttgt       60
ttcatttcct atatttttt  ttatttttt  tattttttaa taagggaaaa tttaacgtct      120
aaggatacag aagattgtta gcacattaaa gtaataaagg cttaagtagt aagtgcctta      180
gcatgttatt gtatttcaaa ggacataatc taaaataata acaatatcat ttctcacaag      240
ttattcaatt ttctttttt  tttctaataa tatcaagaat gtattatttg tttgacataa      300
gtcaactaat ttatttaata tgctggatta atcttgcaga catgtaaatt aacaagtttt      360
agtcaaataa cgttgaagtt tcaatgaact caaataattt ctcttttttt ttatataacc      420
ataagtctaa tctgatttat attttccgca gggatcaact gaagttatga catttggatt      480
ggatcactta taaccttggt cgccaaataa tacaaaaatc agcgttataa acaaagaag       540 gttttttgtta agaaattaat cctctttctt gataagaaag ttgaaccgaa attgcagata      600
ctgatatatg aaaataatac ccacaatttt gggaatagcg caagcctcaa tttaaacaat      660
aggtgaggac acatgataat gacctcaatg attgttagaa gaaagagcc  tcattacaaa      720 atcgaaaaat gaatggttgg gtacaagttt ccaaaacatg gtaaagtgga ctttgcgtat      780
gagacgtaaa tagaaaaaaa cacttgttat atgttttcta gaattattgt tgtctcttta      840
tggttggatg atgcaaaata gtaatttcgg ttagttgctg taaaacacca cgagacaaat      900
```

```
agatatggat atttattaaa tcaggaaaaa cgtaactctc ggctactgga tggttcagtc    960
acccaacgat tactggggag agaaaacagg gcaaaagcaa agcttaaagg aatccgattg   1020
tcattcggca atgtgcagcg aaactaaaaa ccggataatg gacctgttaa tcgaaacatt   1080
gaagatatat aaaggaagag gaatcctggc atatcatcaa ttgaataagt tgaattaatt   1140
atttcaatct cattctcact ttctgactta tagtcgcttt gttaaatcat atgaatttag   1200
acaatttgga tgcaaaattg tcgttctttt cctgacataa tccaattcat ctttacaaca   1260
ctcccttcgt gcttgggact tcagaacttc cagtaagact agtagccgcg cgcatggcaa   1320
cagccagaga tttaaaagcg cttcagcac gatgatggtc attactacca tataagcagg    1380
taacatgcaa agtaattcca gctgctaccg aaaggaata tagtaagtga gggatcattt     1440
cacaggacaa ttccccaacc ttttcacgct taatcccaa atcgataaca gcatagggcc     1500
gtcccgacaa gtcaactacg cttctagaaa gagcttcgtc aagtggacaa taagcatgtc   1560
caaatctttt aacgccggca agttaccca tagcctgctt gaatgcaata ccaagtgcaa     1620
tagcagtatc ttctgcagtg tgatgatcat cgatgattaa atcacctctt gagtaaagtc   1680
gtaagctcca gcctgcatgt ttagccagtg catgatacat gtgatccaag aatccaattc   1740
ccgtgtctac ttggattact tgttctccct tttggtttgc atgcttggaa gttataagtt   1800
catcaataaa attcgactct tcaggtaagg gagcttgtc caaagcgatg caacgctga     1860 ttttcgtttc gttcgtattt cttttctacaa agccctcct catcgtgatg caaaactact   1920
cttttcaatt agatcaaccg agaattacag gaagctagtg cggccatcat cattgttggt   1980
cgtggagtct atggagctgg tcgtaatcct gttgtcgaag ccaagagata tagagaagct   2040
ggttggaagg catatcagca agactttct cagcattaaa aaaagactaa tgtaaaattt     2100
ttttggttgg ttattgaaaa agtcgatgcc ttgtttgcgt ttgttttcct aggcgtttta   2160
tgtcagaagg catttagaat tagtatacaa gtactctttg gtaaaatttt atgtagcgac   2220
taaaatatta actattatag ataaacacct tgggaataaa aagtaatttg ctatagtaat   2280
ttattaaaca tgctcctaca acattaccac aatcttttct cttggattga cattgaataa   2340
gaaaagagtg aatttttta gacttgtaat gataactatg tacaaagcca atgaaagatg     2400
tatgtagatg aatgtaaaat a                                             2421
```

<210> SEQ ID NO 18
<211> LENGTH: 3641
<212> TYPE: DNA
<213> ORGANISM: Artificial Sequence
<220> FEATURE:
<223> OTHER INFORMATION: Synthetic Construct; promoter-RD-his5-ERISx3-u4

<400> SEQUENCE: 18

```
cgactctaga ggatcagaaa attatcgcca taaaagacag aataagtcat cagcggttgt     60
ttcatttcct atattttttt tttatttttt tattttttaa taagggaaaa tttaacgtct    120
aaggatacag aagattgtta gcacattaaa gtaataaagg cttaagtagt aagtgcctta    180
gcatgttatt gtatttcaaa ggacataatc taaaataata acaatatcat ttctcacaag    240
ttattcaatt ttcttttttt tttctaataa tatcaagaat gtattatttg tttgacataa    300
gtcaactaat ttatttaata tgctggatta atccttgcaga catgtaaatt aacaagtttt    360
agtcaaataa cgttgaagtt tcaatgaact caaataattt ctcttttttt ttatataacc   420
ataagtctaa tctgatttat attttccgca gggatcaact gaagttatga catttggatt    480
ggatcactta taaccttggt cgccaaataa tacaaaaatc agcgttataa aacaaagaag    540
```

```
gttttttgtta agaaattaat cctctttctt gataagaaag ttgaaccgaa attgcagata    600
ctgatatatg aaaataatac ccacaatttt gggaatagcg caagcctcaa tttaaacaat    660
aggtgaggac acatgataat gacctcaatg attgttagaa gaaaagagcc tcattacaaa    720
atcgaaaaat gaatggttgg gtacaagttt ccaaaacatg gtaaagtgga ctttgcgtat    780
gagacgtaaa tagaaaaaaa cacttgttat atgttttcta gaattattgt tgtctcttta    840
tggttggatg atgcaaaata gtaatttcgg ttagttgctg taaaacacca cgagacaaat    900
agatatggat atttattaaa tcaggaaaaa cgtaactctc ggctactgga tggttcagtc    960
acccaacgat tactggggag agaaaacagg gcaaagcaa agcttaaagg aatccgattg   1020
tcattcggca atgtgcagcg aaactaaaaa ccggataatg gacctgttaa tcgaaacatt   1080
gaagatatat aaaggaagag gaatcctggc atatcatcaa ttgaataagt tgaattaatt   1140
atttcaatct cattctcact ttctgactta tagtcgcttt gttaaatcat atgaatttag   1200
acaatttgga tgcaaaattg tcgttctttt cctgacataa tccaattcat ctttacaaca   1260
ctcccttcgt gcttgggact tcagaacttc cagtaagact agtagccgcg cgcatggcaa   1320
cagccagaga tttaaaagcg ctttcagcac gatgatggtc attactacca tataagcagg   1380
taacatgcaa agtaattcca gctgctaccg aaaaggaata tagtaagtga gggatcattt   1440
cacaggacaa ttccccaacc ttttcacgct ttaatcccaa atcgataaca gcatagggcc   1500
gtcccgacaa gtcaactacg cttctagaaa gagcttcgtc aagtggacaa taagcatgtc   1560
caaatctttt aacgccggca aagttaccca tagcctgctt gaatgcaata ccaagtgcaa   1620
tagcagtatc ttctgcagtg tgatgatcat cgatgattaa atcacctctt gagtaaagtc   1680
gtaagctcca gcctgcatgt ttagccagtg catgatacat gtgatccaag aatccaattc   1740
ccgtgtctac ttggattact tgttctccct tttggtttgc atgcttggaa gttataagtt   1800
catcaataaa attcgactct tcaggtaagg gagctttgtc caaagcgatg gcaacgctga   1860
ttttcgtttc gttcgtattt cttttctacaa aagccctcct catcgtgatg caaaactact   1920
cttttcaatt agatcaaccg agaattacag gaagctagtg attaactgca gctcaagtga   1980
ctgcattaaa gcataatacc gaagcactga cataacagag aggttcagaa aggaatttaa   2040
agattgactt tttcgacaaa cttcatgtta caagtcttat cgtttgtgtt tataaatcat   2100
cagcctctct ctatatctct atatctctat atctctatat atcagatata aagatgcaag   2160
ttttgaagta gacattccgc acaaagtcta gtacaccatg tctcttgtgc tcaggctggt   2220
tgtcctgcaa aaatgtacaa caggcaaatg gatgtttcat caaagatgga ctcctttgtc   2280
tcatacttat tgatggcgaa gctagatccg ttatcatctt gagaaaacac atcgttgtct   2340
tcagagtctg cagttaatcc cgcggtctag tgattaactg cagctcaagt gactgcatta   2400
aagcataata ccgaagcact gacataacag agaggttcag aaaggaattt aaagattgac   2460
tttttcgaca aacttcatgt tacaagtctt atcgtttgtg tttataaatc atcagcctct   2520
ctctatatct ctatctctct atatctctat atcagatata aagatgcaag ttttgaag    2580
tagacattcc gcacaaagtc tagtacacca tgtctcttgt gctcaggctg ttgtcctgc    2640
aaaaatgtac aacaggcaaa tggatgtttc atcaaagatg gactcctttg tctcatactt   2700
attgatggcg aagctagatc cgttatcatc ttgagaaaac acatcgttgt cttcagagtc   2760
tgcagttaat cccgcggtct agtgattaac tgcagctcaa gtgactgcat taaagcataa   2820
taccgaagca ctgacataac agagaggttc agaaaggaat ttaaagattg acttttcga    2880
caaacttcat gttacaagtc ttatcgtttg tgtttataaa tcatcagcct ctctctatat   2940
```

```
ctctatatct ctatatctct atatatcaga tataaagatg caagttttga agtagacatt    3000
ccgcacaaag tctagtacac catgtctctt gtgctcaggc tggttgtcct gcaaaaatgt    3060
acaacaggca aatggatgtt tcatcaaaga tggactcctt tgtctcatac ttattgatgg    3120
cgaagctaga tccgttatca tcttgagaaa acacatcgtt gtcttcagag tctgcagtta    3180
atcccatcat cattgttggt cgtggagtct atggagctgg tcgtaatcct gttgtcgaag    3240
ccaagagata tagagaagct ggttggaagg catatcagca aagactttct cagcattaaa    3300
aaaagactaa tgtaaaattt ttttggttgg ttattgaaaa agtcgatgcc ttgtttgcgt    3360
ttgttttcct aggcgtttta tgtcagaagg catttagaat tagtatacaa gtactctttg    3420
gtaaaatttt atgtagcgac taaaatatta actattatag ataaacacct tgggaataaa    3480
aagtaatttg ctatagtaat ttattaaaca tgctcctaca acattaccac aatcttttct    3540
cttggattga cattgaataa gaaaagagtg aattttttta gacttgtaat gataactatg    3600
tacaaagcca atgaaagatg tatgtagatg aatgtaaaat a                       3641
```

<210> SEQ ID NO 19
<211> LENGTH: 765
<212> TYPE: DNA
<213> ORGANISM: Artificial Sequence
<220> FEATURE:
<223> OTHER INFORMATION: Synthetic Construct; psi-GFP2-238

<400> SEQUENCE: 19

```
aagcttcgta cgctgcaggt cgacggatcc ccgggttaat taacagtaaa ggagaagaac     60
ttttcactgg agttgtccca attcttgttg aattagatgg tgatgttaat gggcacaaat    120
tttctgtcag tggagagggt gaaggtgatg caacatacgg aaaacttacc cttaaattta    180
tttgcactac tggaaaacta cctgttccat ggccaacact tgtcactact ttcacttatg    240
gtgttcaatg cttttcaaga tacccagatc atatgaaacg gcatgacttt ttcaagagtg    300
ccatgcccga aggttatgta caggaaagaa ctatattttt caaagatgac gggaactaca    360
agacacgtgc tgaagtcaag tttgaaggtg ataccctttgt taatagaatc gagttaaaag    420
gtattgattt taaagaagat ggaaacattc ttggacacaa attggaatac aactataact    480
cacacaatgt atacatcatg gcagacaaac aaaagaatgg aatcaaagtt aacttcaaaa    540
ttagacacaa cattgaagat ggaagcgttc aactagcaga ccattatcaa caaaatactc    600
caattggcga tggccctgtc cttttaccag acaaccatta cctgtccaca caatctgccc    660
tttcgaaaga tcccaacgaa aagagagacc acatggtcct tcttgagttt gtaacagctg    720
ctgggattac acatggcatg gatgaactat acaaataggg cgcgc                    765
```

<210> SEQ ID NO 20
<211> LENGTH: 2000
<212> TYPE: DNA
<213> ORGANISM: Artificial Sequence
<220> FEATURE:
<223> OTHER INFORMATION: Synthetic Construct; psi-GFP2-238-SIREx3

<400> SEQUENCE: 20

```
aagcttcgta cgctgcaggt cgacggatcc ccgggttaat taacagtaaa ggagaagaac     60
ttttcactgg agttgtccca attcttgttg aattagatgg tgatgttaat gggcacaaat    120
tttctgtcag tggagagggt gaaggtgatg caacatacgg aaaacttacc cttaaattta    180
tttgcactac tggaaaacta cctgttccat ggccaacact tgtcactact ttcacttatg    240
gtgttcaatg cttttcaaga tacccagatc atatgaaacg gcatgacttt ttcaagagtg    300
```

| | |
|---|---|
| ccatgcccga aggttatgta caggaaagaa ctatatttt caaagatgac gggaactaca | 360 |
| agacacgtgc tgaagtcaag tttgaaggtg ataccttgt aatagaatc gagttaaaag | 420 |
| gtattgattt taaagaagat ggaaacattc ttggacacaa attggaatac aactataact | 480 |
| cacacaatgt atacatcatg gcagacaaac aaaagaatgg aatcaaagtt aacttcaaaa | 540 |
| ttagacacaa cattgaagat ggaagcgttc aactagcaga ccattatcaa caaaatactc | 600 |
| caattggcga tggccctgtc cttttaccag acaaccatta cctgtccaca caatctgccc | 660 |
| tttcgaaaga tcccaacgaa aagagagacc acatggtcct tcttgagttt gtaacagctg | 720 |
| ctgggattac acatggcatg gatgaactat acaaataggg cgcgctagac cgcgggatta | 780 |
| actgcagact ctgaagacaa cgatgtgttt tctcaagatg ataacggatc tagcttcgcc | 840 |
| atcaataagt atgagacaaa ggagtccatc tttgatgaaa catccatttg cctgttgtac | 900 |
| attttttgcag acaaccagc tgagcacaa gagacatggt gtactagact ttgtgcggaa | 960 |
| tgtctacttc aaaacttgca tctttatatc tgatatatag agatatagag atatagagat | 1020 |
| atagagagag gctgatgatt tataaacaca acgataaga cttgtaacat gaagtttgtc | 1080 |
| gaaaaagtca atctttaaat tcctttctga acctctctgt tatgtcagtg cttcggtatt | 1140 |
| atgctttaat gcagtcactt gagctgcagt taatcactag accgcgggat taactgcaga | 1200 |
| ctctgaagac aacgatgtgt tttctcaaga tgataacgga tctagcttcg ccatcaataa | 1260 |
| gtatgagaca aaggagtcca tctttgatga acatccatt tgcctgttgt acattttgc | 1320 |
| aggacaacca gcctgagcac aagagacatg gtgtactaga ctttgtgcgg aatgtctact | 1380 |
| tcaaaacttg catctttata tctgatatat agagatatag agatatagag atatagagag | 1440 |
| aggctgatga tttataaaca caaacgataa gacttgtaac atgaagtttg tcgaaaaagt | 1500 |
| caatctttaa attcctttct gaacctctct gttatgtcag tgcttcggta ttatgcttta | 1560 |
| atgcagtcac ttgagctgca gttaatcact agaccgcggg attaactgca gactctgaag | 1620 |
| acaacgatgt gttttctcaa gatgataacg gatctagctt cgccatcaat aagtatgaga | 1680 |
| caaaggagtc catctttgat gaaacatcca tttgcctgtt gtacattttt gcaggacaac | 1740 |
| cagcctgagc acaagagaca tggtgtacta gactttgtgc ggaatgtcta cttcaaaact | 1800 |
| tgcatcttta tatctgatat atagagatat agagatatag agatatagag agaggctgat | 1860 |
| gatttataaa cacaaacgat aagacttgta acatgaagtt tgtcgaaaaa gtcaatcttt | 1920 |
| aaattccttt ctgaacctct ctgttatgtc agtgcttcgg tattatgctt taatgcagtc | 1980 |
| acttgagctg cagttaatca | 2000 |

<210> SEQ ID NO 21
<211> LENGTH: 530
<212> TYPE: DNA
<213> ORGANISM: Artificial Sequence
<220> FEATURE:
<223> OTHER INFORMATION: Synthetic Construct; psi-GFP2-163

<400> SEQUENCE: 21

| | |
|---|---|
| aagcttcgta cgctgcaggt cgacggatcc ccgggttaat taacagtaaa ggagaagaac | 60 |
| ttttcactgg agttgtccca attcttgttg aattagatgg tgatgttaat gggcacaaat | 120 |
| tttctgtcag tggagagggt gaaggtgatg caacatacgg aaaacttacc cttaaattta | 180 |
| tttgcactac tggaaaacta cctgttccat ggccaacact tgtcactact ttcacttatg | 240 |
| gtgttcaatg cttttcaaga tacccagatc atatgaaacg gcatgacttt ttcaagagtg | 300 |
| ccatgcccga aggttatgta caggaaagaa ctatatttt caaagatgac gggaactaca | 360 |

| | |
|---|---|
| agacacgtgc tgaagtcaag tttgaaggtg atacccttgt taatagaatc gagttaaaag | 420 |
| gtattgattt taaagaagat ggaaacattc ttggacacaa attggaatac aactataact | 480 |
| cacacaatgt atacatcatg gcagacaaac aaaagaatgg aatcaaagtt | 530 |

<210> SEQ ID NO 22
<211> LENGTH: 1766
<212> TYPE: DNA
<213> ORGANISM: Artificial Sequence
<220> FEATURE:
<223> OTHER INFORMATION: Synthetic Construct; psi-GFP2-163-SIREx3

<400> SEQUENCE: 22

| | |
|---|---|
| aagcttcgta cgctgcaggt cgacggatcc ccgggttaat taacagtaaa ggagaagaac | 60 |
| ttttcactgg agttgtccca attcttgttg aattagatgg tgatgttaat gggcacaaat | 120 |
| tttctgtcag tggagagggt gaaggtgatg caacatacgg aaaacttacc cttaaattta | 180 |
| tttgcactac tggaaaacta cctgttccat ggccaacact tgtcactact ttcacttatg | 240 |
| gtgttcaatg cttttcaaga tacccagatc atatgaaacg gcatgacttt tcaagagtg | 300 |
| ccatgcccga aggttatgta caggaaagaa ctatattttt caaagatgac gggaactaca | 360 |
| agacacgtgc tgaagtcaag tttgaaggtg atacccttgt taatagaatc gagttaaaag | 420 |
| gtattgattt taaagaagat ggaaacattc ttggacacaa attggaatac aactataact | 480 |
| cacacaatgt atacatcatg gcagacaaac aaaagaatgg aatcaaagtt ctagaccgcg | 540 |
| ggattaactg cagactctga agacaacgat gtgttttctc aagatgataa cggatctagc | 600 |
| ttcgccatca ataagtatga gacaaaggag tccatctttg atgaaacatc catttgcctg | 660 |
| ttgtacattt ttgcaggaca accagcctga gcacaagaga catggtgtac tagactttgt | 720 |
| gcggaatgtc tacttcaaaa cttgcatctt tatatctgat atatagagat atagagatat | 780 |
| agagatatag agagaggctg atgatttata aacacaaacg ataagacttg taacatgaag | 840 |
| tttgtcgaaa aagtcaatct ttaaattcct ttctgaacct ctctgttatg tcagtgcttc | 900 |
| ggtattatgc tttaatgcag tcacttgagc tgcagttaat cactagaccg cgggattaac | 960 |
| tgcagactct gaagacaacg atgtgttttc tcaagatgat aacggatcta gcttcgccat | 1020 |
| caataagtat gagacaaagg agtccatctt tgatgaaaca tccatttgcc tgttgtacat | 1080 |
| ttttgcagga caaccagcct gagcacaaga gacatggtgt actagacttt gtgcggaatg | 1140 |
| tctacttcaa aacttgcatc tttatatctg atatatagag atatagagat atagagatat | 1200 |
| agagagaggc tgatgattta aaacacaaa cgataagact tgtaacatga agtttgtcga | 1260 |
| aaaagtcaat ctttaaattc ctttctgaac ctctctgtta tgtcagtgct tcggtattat | 1320 |
| gctttaatgc agtcacttga gctgcagtta atcactagac cgcgggatta actgcagact | 1380 |
| ctgaagacaa cgatgtgttt tctcaagatg ataacggatc tagcttcgcc atcaataagt | 1440 |
| atgagacaaa ggagtccatc tttgatgaaa catccatttg cctgttgtac attttttgcag | 1500 |
| gacaaccagc ctgagcacaa gagacatggt gtactagact ttgtgcggaa tgtctacttc | 1560 |
| aaaacttgca tctttatatc tgatatatag agatatagag atatagagat atagagagag | 1620 |
| gctgatgatt tataaacaca acgataaga cttgtaacat gaagtttgtc gaaaaagtca | 1680 |
| atctttaaat tcctttctga acctctctgt tatgtcagtg cttcggtatt atgctttaat | 1740 |
| gcagtcactt gagctgcagt taatca | 1766 |